US006849612B2

(12) United States Patent
Bennett et al.

(10) Patent No.: US 6,849,612 B2
(45) Date of Patent: Feb. 1, 2005

(54) OLIGONUCLEOTIDE MODULATION OF CELL ADHESION

(75) Inventors: C. Frank Bennett, Carlsbad, CA (US); Christopher Mirabelli, Dover, MA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 63 days.

(21) Appl. No.: 09/982,262

(22) Filed: Oct. 18, 2001

(65) Prior Publication Data

US 2003/0077565 A1 Apr. 24, 2003

Related U.S. Application Data

(63) Continuation-in-part of application No. 09/659,288, filed on Sep. 12, 2000, now abandoned, which is a continuation of application No. 09/128,496, filed on Aug. 3, 1998, now Pat. No. 6,169,079, which is a continuation of application No. 08/440,740, filed on May 12, 1995, now Pat. No. 5,843,738, which is a continuation-in-part of application No. 08/063,167, filed on May 17, 1993, now Pat. No. 5,514,788, which is a continuation of application No. 07/969,151, filed on Feb. 10, 1993, now abandoned, which is a continuation-in-part of application No. 08/007,997, filed on Jan. 21, 1993, now Pat. No. 5,591,623.

(51) Int. Cl.$^7$ .......................... A01N 43/04; C12P 19/34; C12N 15/63; C07H 21/02; C07H 21/04

(52) U.S. Cl. ............................ 514/44; 435/6; 435/91.1; 435/91.31; 435/455; 536/23.1; 536/24.5

(58) Field of Search ..................... 435/6, 91.1, 91.31, 435/455, 458; 514/44; 536/23.1, 24.5

(56) References Cited

U.S. PATENT DOCUMENTS

| 5,786,201 | A | | 7/1998 | Kahn et al. ............... 435/240.2 |
| 5,843,738 | A | | 12/1998 | Bennett et al. ........... 435/172.3 |
| 6,153,582 | A | * | 11/2000 | Skelnik ....................... 514/12 |
| 6,537,808 | B2 | * | 3/2003 | Lambiase ................... 435/325 |

OTHER PUBLICATIONS

Agrawal et al. Molecular Med. Today, Feb. 2000, vol. 6: 72–81.*
Pihl–Carey, I. BioWorld Today. Dec. 1999, vol. 10: 1–2.*
Chirila et al. Biomaterials, 2002, vol. 23: 321–342.*
Palu et al. Biotech. 1999, vol. 68: 1–13.*
Tamm et al. The Lancet. Aug., 2001, vol. 358: 489–497.*
Busen et al., "Ribonuclease H Levels during the Response of Bovine Lymphocytes to Concanavalin A", *Eur. J. Biochem.*, 1977, 74, 203–208.
Busen, W., and Hausen, P., "*Distinct Ribonuclease H Activities in Calf Thymus*", *Bur. J. Biochem.*, 1975, 52, 179–190.
Busen, W., *J. Biol. Chem.*, "The Subunit Structure of Calf Thymus Ribonuclease HI As Revealed by Immunological Analysis", 1982, 257, 7106–7108.

Cazenave et al., "Comparative inhibition of rabbit globin mRNA translation by modified antisense oligodeoxynucleotides", *Nucleic Acid Res.*, 1989, 17, 4255–4273.
Crooke, S.T. et al., "Kinetic characteristics of *Escherichia coli* Rnase H1: cleavage of various antisense oligonucleotide–RNA duplexes", *Biochem. J.*, 1995, 312, 599–608.
Dash et al., "Selective elimination of mRNAs in vivo: Complementary oligodeoxynucleotides promote RNA degradation by an Rnase H–like activity", *Proc. Nat'l Acad. Sci. USA*, 1987, 84, 7896–7900.
Frank et al., "Purification and characterization of human ribonuclease HII", *Nucleic Acids Res.*, 1994, 22, 5247–5254.
Gagnor et al., "α–DNA VI:comparative study of α–and β–anomeric oligodeoxyribonucleotides in hybridization to mRNA and in cell free translation inhibition", *Nucleic Acid Res.*, 1987, 15, 10419–10436.
Itaya, M., "Isolation and characterization of a second Rnase H (Rnase HII) of *Escherichia coli* K–12 encoded by the rnhB gene", *Proc. Natl. Acad. Sci. USA*, 1990, 87, 8587–8591.
Itaya, M. Kondo K., Molecular cloning of a ribonuclease H (Rnase HI) gene from an extreme thermophile *Thermus thermophilus* HB8: a thermostable Rnase H can functionally replace the *Escherichia coli* enzyme in vivo.
Itaya et al., "*Selective cloning of genes encoding Rnase H from Salmonella typhimurium, Saccharomyces cerevisiae* and *Escherichia coli rnh mutant*", *Mol. Gen. Genet.*, 1991, 227, 438–445.
Kanaya et al., Importance of the Positive Charge Cluster in *Escherichia coli* Ribonuclease HI for the Effective Binding of the S *J. Biol. Chem.*, 1991, 266, 11621–11627.
Kane, C. M., "Renaturase and Ribonuclease H: A Novel Mechanism That Influences Transcript Displacement by RNA Polymerase II in Vitro", *Biochemistry*, 1988, 27, 3187–3196.
Katayanagi et al., "Crystal Structure of *Escherichia coli* Rnase HI in Complex with Mg$^{2+}$ at 2.8 A Resolution: Proof for a Single Mg$^2$ Binding Site", *Proteins: Struct., Funct., Genet.*, 1993, 17, 337–346.
Katayanagi et al., "Three–dimensional structure of ribonuclease H from *E. Coli*", *Nature*, 1990, 347, 306–309.
Lima, W.F. and Crooke, S.T., "Binding Affinity and Specificity of *Escherichia coli* Rnase H1: Impact on the Kinetics of Catalysis of Antisense Oligonucleotide–RNA Hybrids", *Biochemistry*, 1997, 36, 390–398.

(List continued on next page.)

Primary Examiner—Ram R. Shukla
Assistant Examiner—Jane Zara
(74) Attorney, Agent, or Firm—Licata & Tyrrell P.C.

(57) ABSTRACT

Compositions and methods for the treatment of ophthalmic disorders, particularly preservation of corneal explants and prevention of corneal allograft rejection. These compositions comprise oligonucleotides which are specifically hybridizable with nucleic acids encoding the cellular adhesion molecules intercellular adhesion molecule-1 (ICAM-1), vascular cell adhesion molecule-1 (VCAM-1) and endothelial leukocyte adhesion molecule-1 (ELAM-1).

9 Claims, 26 Drawing Sheets

OTHER PUBLICATIONS

Lima, W.F. et al., "The Influence of Antisense Oligonucleotide–induced RNA Structure on *Escherichia coli* Rnase H1 Activity", *J. Biol. Chem.*, 1997, 272, 18191–18199.

Monia et al., "Evaluation of 2'–Modified Oligonucleotides Containing 2'–Deoxy Gaps as Antisense Inhibitors of Gene Expression", *J. Biol. Chem.*, 1993, 266:13, 14514–14522.

Nakamura et al., "How does Rnase H recognize a DNA–RNA hybrid", *Proc. Natl. Acad. Sci. USA*, 1991, 88, 11535–11539.

Tidd, D.M. and Worenius, H.M., "Partial protection of oncogene, anti–sense oligodeoxynucleotides against serum nuclease degradation using terminal methylphosphonate groups", *Br. J. Cancer*, 1989, 60, 343 ups:.

Tidd, D.M. et al., "Evaluation of N–ras oncogene anti–sense, sense and nonsense sequence methylphosphonate oligonucleotide analogues", *Anti–Cancer Drug Des.*, 1988, 3, 117.

Walder, R.Y. and Walder, J.A., "Role of Rnase H in hybrid–arrested translation by antisense oligonucleotides", *Proc. Nat'l Acad. Sci. USA*, 1988, 85, 5011–5015.

Wintersberger, U., "Ribonucleases H of Retroviral and Cellular Origin", *Pharmac. Ther.*, 1990, 48, 259–280.

Yang et al., "Structure of Ribonuclease H Phased at 2 A Resolution by MAD Analysis of Selenomethionyl Protein", *Science*, 1990, 249, 1398–1405.

Agrawal, S. et al., "Site–specific excision from RNA by Rnase H and mixed–phosphate–backbone oligodeoxynynucleotides" *Proc. Natl. Acad. Sci. USA* 1990 87(4):1401–1405.

Boado R.J. et al., "Complete inactivation of target mRNA by biotinylated antisense oligodeoxynucleotide–avidin conjugates" *Bioconjug. Chem.* 1994 5(5):406–410.

Bordier, B. et al., "Sequence–specific Inhibition of Human Immunodeficiency virus (HIV) reverse transcription by Antisense Oligonucleotides:Comparative Study in Cell–free assays and in HIV–infected cells", *Proc. Natl. Acad. Sci. USA* 1995 92:9383–9387.

Chiang, M.Y. et al., "Antisense oligonucleotides inhibit intercellular adhesion molecule 1 expression by two distinct mechanisms", *J. Biol. Chem.* 1991 266(27):18162–18171.

Dean, N.M. et al., "Inhibition of protein kinase C–alpha expression in human A549 cells by antisense oligonucleotides inhibits induction of intercellular adhesion molecule 1 (CAM–1) mRNA phorbol esters" *J. Biol. Chem.* 1994 269(23):16416–16424.

Furdon, P.J. et al., "RNASE H cleavage of RNA hybridized to oligonucleotides containing methylphosphonate, phosphorothioate and phosphodiester bonds", *Nucleic Acids Res.* 1989 17(22):9193–9204.

Ghosh, M.K. et al., "Phosphorothioate–phosphodiester oligonucleotide copolymers; assessement for antisense application", *Anticancer Drug Des.* 1993 8(1):15–32.

Giles R.V. et al., "Enhanced RNase H activity with methylphosphonodiester/phosphodiester chimeric antisense oligodeoxynucleotides", *Anticancer Drug Des.* 1992 7(1):37–48.

Giles, R.V. et al., "Increased specificity for antisense oligodeoxynucleotide targeting of RNA cleavage by RNase H using chimeric methylphosphonodiester/phosphodiester structures", *Nucleic Acids Res.* 1992 20(4):763–770.

Godard, G. et al., "Antisense effects of cholesterol–oligonucleotide conjugates associated with poly(alkylcyanoacrylate) nonoparticles", *Eur. J. Biochem.* 1995 232(2):404–410.

Gottikh, M. et al., "Alpha beta chimeric antisense oligonucleotides; synthesis and nuclease resistance in biological media", *Antisense Res. Dev.* 1994 4(4):251–258.

Hoke, G.D. et al., "Effects of phosphorothioate capping on antisense oligonucleotide stability, hybridization and antiviral efficacy versus herpes simplex virus infection", *Nucleic Acids Res.* 1991 19(20)5743–5748.

Lee C.H. et al., "Antisense gene suppression against human ICAM–1, ELAM–1 and VCAM–1 in cultured human umbilical vein endothelial cells", *Shock* 1995 4(1):1–10.

Liu P.K. et al., "Suppression of ischemia–induced fos expression and AP–1 activity by an antisense oligodeoxynucleotide to c–fos mRNA", *Ann. Neurol.* 1994 36(4):566–576.

Rosolen A. et al., "Effect of over–expression of bacterial ribonuclease H on the utility of antisense MYC oligodeoxynucleotides in the monocytic leukemia cell line U937", *Biochimie* 1993 75(1–2):79–87.

Saison–Behmoaras B.T. et al. "Short modified antisense oligonucleotides directed against Ha–ras point mutation induce selective cleavage of the mRNA and inhibit T24 cells proliferation", *EMBO J.* 1991 10(5):1111–1118.

Dagle J.M. et al., "Targeted degradation of mRNA in *Xenopus oocytes* and embryos directed by modified oligonucleotides: studies of An2 and cyclin in embryogenesis", *Nucleic Acids Res.* 1990 18(16):4751–4757.

Kawasaki E., "Quantitative hybridization–arrest of mRNA in *Xenopus oocytes* using single–stranded complementary DNA or oligonucleotide probes", *Nucleic Acids Res.* 1985 13(13):4991–5005.

Quartin R.S., "Number and distribution of methylphosphonate linkages in oligodeoxynucleotides affect exo–and endonuclease sensitivity and ability to form RNASE H substrates", *Nucleic Acids Res.* 1989 17(18):7233–7262.

Adams et al., Intercellular Adhesion Molecule 1 on Liver Allografts During Rejection, *Lancet* 1989, 1122–1125.

Anderson and Springer, Leukocyte Adhesion Deficiency: An Inherited Defect in the Mac–1, LFA–1, and p150,95 Glycoproteins, *Ann. Rev. Med.* 1987, 38, 175–194.

Bevilacqua et al., Endothelial Leukocyte Adhesion Molecule 1: An Inducible Receptor for Neutorophils Related to Complement Regulatory Proteins and Lectins, *Science* 1989, 243, 1160–1165.

Bevilacqua et al., Identification of an Inducible Endothelial–leukocyte Adhesion Molecule, *Proc. Natl. Acad. Sci. USA* 1987, 84, 9238–9242.

Campbell et al., Intercellular Adhesion Molecule 1 is Induced on Isolated Endocrine Islet Cells by Cytokines but not be Reovirus Infection, *Proc. Natl. Acad. Sci. U.S.A.* 1989, 86, 4282–4286.

Cosimi et al., In vivo Effects of Monoclonal Antibody to ICAM–1 (CD54) in Nonhuman Primates with Renal Allografts, *J. Immunol.* 1990, 144, 4604–4612.

Dustin and Springer, Lymphocyte Function–associated Antigen–1 (LFA–1) Interaction with Intercellular Adhesion Molecule–1 (ICAM–1) is One of At Least Three Mechanisms for Lymphocye Adhesion to Cultured Endothelial Cells, *J. Cell Biol.* 1988, 107, 321–331.

Faull and Russ, Tubular Expression of Intercellular Adhesion Molecule–1 During Renal Allograft Rejection, *Transplantation* 1989, 48, 226–230.

Frohman et al., The induction of intercellular adhesion moleculte 1 (ICAM–1) expression on human fetal astrocytes by interferon–γ, tumor necrosis factor α, lymphotoxim, and interleukin–1: relevance to intracerebral antigen presentation, *J. Neuroimmunol.* 1989, 23, 117–124.

Greve et al., The Major Human Rhinovirus Receptor is ICAM–1, *Cell* 1989, 56, 839–847.

Griffiths and Nickoloff, Keratinocyte Intercellulr Adhesion Molecule–1 (ICAM–1) Expression Precedes Dermal T Lymphocytic Infiltratin in Allergic Contact Dermatitis (*Rhus dermatitis*), *Am. J. Pathology* 1989, 135, 1045–1053.

Hale et al., Immunohistologic Analysis of the Distribution of Cell Adhesion Molecules with the Inflammatory Synovial Microenvironment, *Arth. Rheum.* 1989, 32, 22–30.

Harlan, J.M., Leukocyte–Endothelial Interactions, *Blood* 1985, 65, 513–525.

Ho et al., Treatment of Severe Lichen Planus with Cyclosporine, *J. Am. Acad. Dermatol.* 1990, 22, 64–68.

Isobe et al., Specific Acceptance of Cardiac Allograft After Treatment with Antibodies to ICAM–1 and LFA–1, *Science* 1992, 255, 1125–1127.

Isobe et al., *Early Detection of Rejection and Assessment of Cyclosporine Therapy by* $^{111}$*In Antimyosin Imaging in Mouse Heart Allografts,* (1991) Circulation 84:1246–1255.

Lisby et al., Intercellular Adhesion Molecule–1 (ICAM–1) Expression Correlated to Inflammation, *Br. J. Dermatol.* 1989, 120, 479–484.

M. Zuker, On Findings All Suboptimal Foldings of an RNA Molecule, *Science* 1989, 244, 48–52.

Marlin et al., A soluble form of intercellular adhesion molecule–1 inhibits rhinovirus infection, *Nature* 1990, 344, 70–72.

Miller, D.E. and Welch, D.R., Cytokine Modulation of Intercellular Adhesion Molecule–1 Surface Expression on Human Melanoma Cells; Correlation with Adhesion of Peripheral Blook Leukocytes, (1990) Proc. Am. Assoc. Cancer Res. 13: 353.

Osborn et al., Direct Expression Cloning of Vasular Cell Adhesion Molecule 1, a Cytokine–Induced Endothelial Protein that Binds to Lymphocytes, *Cell* 1989 59:1203–11.

P.E. Nielsen, et al., Sequence–Selective Recognition of DNA by Strand Displacement with a Thymine–Substituted Polyamide, *Science* 1991, 254, 1497.

Petersheim, M. and D.H. Turner, Base–Stacking and Base–Pairing Contributions to Helix Stability: Thermodynamics of Double–Helix Formation with CCGG, CCGGp, CCGGAp, ACCGGp, CCGGUp and ACCGGUp, *Biochemistry* 1983, 22, 256–263.

Rice and Bevilacqua, An Inducible Endothelial Cell Surface Glycoprotein Mediates Melanoma Adhesion, *Science* 1989, 246, 1303–1306.

Rice et al., Inducible Cell Adhesion Molecule 110 (INCAM–110) is an Endothelial Receptor for Lymphocytes, *J. Exp. Med.* 1990, 171, 1369–1374.

Rothenberg et al., Oligonucleotides as Anti–sense Inhibitors of Gene Expression: Therapeutic Implications, *J. Natl. Cancer Inst.* 1989, 81, 1539–1544.

Shiohara et al., Fixed Druge Eruption, *Arch. Dermatol.* 1989, 125, 1371–1376.

Staunton et al., A Cell Adhesion Molecule, ICAM–1, is the Major Surface Receptor for Rhimoviruses, *Cell* 1989, 56, 849–853.

Staunton et al., Primary Structure of ICAM–1 Demonstrates Interaction between Members of the Immunoglobulin and Integrin Supergene Families, *Cell* 1988, 52, 925–933.

Staunton et al., The Arrangement of the Immunoglobulin–like Domains of ICAM–1 and the Binding Sites for LFA–1 and Rhinovirus, *Cell* 1990, 61, 243–254.

Weetman et al., Expression of an Intercellular Adhesion Molecule, ICAM–1, by Human Thyroid Cells, *J. Endocrinol.* 1989, 122, 185–191.

Wegner et al., Intercellular Adhesion Molecule–1 (ICAM–1) in the Phatogenesis of Asthma, *Science* 1990, 247, 456–459.

Wellicome et al., A Monoclonal Antibody that Detects a Novel Antigen on Endothelial Cells that is Induced by Tumor Necrosis Factor, IL–1, or Lipopolysaccharide, *J. Immunol.* 1990, 144, 2558–2565.

Zon, G., Oligonucleotide Analogues as Potential Chemotherapeutic Agents, *Pharmaceutical Res.* 1988, 5, 539–549.

Okayasu et al., A Novel Method in the Induction of Reliable Experimental Acute and Chronic Ulcerative Colitis in Mice, (1990) Gastroenterology 98:694–702.

Sambrook et al., *Molecular Cloning, A Laboratory Manual*, 2nd ed., Cold Spring Harbor Laboratory Press, 1989, vol. 2, p. 10.59.

* cited by examiner

FIG. 1A

```
GCTATAAGGA TCACGCGCCC CAGTCGACGC TGAGCTCCTC TGCTACTCAG AGTTGCAACC TCAGCCTCGCT

ATG GCT CCC AGC AGC CCC CGG CCC GCA CTC CTG GTC GTG CTC GGG GGA GCT CTG TTC CCA
MET ALA PRO SER SER PRO ARG PRO ALA LEU LEU VAL VAL LEU GLY GLY ALA LEU PHE PRO

GGA CCT GGC AAT GCC CAG ACA TCT GTG TCC CCC AAA ATC CTG CCC CGG GGA GGC TCC GTG
GLY PRO GLY ASN ALA GLN THR SER VAL SER PRO LYS ILE LEU PRO ARG GLY GLY SER VAL

CTG GTG ACA TGC AGC ACC TCC TGT GAC CAG CCC AAG TTG GGC ATA CCG TTG CCT AAA
LEU VAL THR CYS SER THR SER CYS ASP GLN PRO LYS LEU GLY ILE PRO LEU PRO LYS

AAG GAG TTG CTC CTG TAT CAG AAG GTG TAT GAA CGG ACC TTC CTC ACC GTG TAC
LYS GLU LEU LEU LEU TYR GLN LYS VAL TYR GLU ARG THR PHE LEU THR VAL TYR

CAA CCA ATG TGC TAT TCA AAC TGC CCT GAT GGG CAG TCA GCT AAA ACA CCA GTG TAC
GLN PRO MET CYS TYR SER ASN CYS PRO ASP GLY GLN SER ALA LYS THR PRO VAL TYR

TGG ACT CCA GAA CGG GTG GAG CTG CCC TCT TGG CAG CCC GCA GTG CCA AAC TTC CTC ACC
TRP THR PRO GLU ARG VAL GLU LEU PRO SER TRP GLN PRO ALA VAL PRO ASN PHE LEU THR

CTA CGC TGC CAG GTG CAG GAG GGT GGG CCC CGG GCC AAC CTG ACC GTG GTG CTC CGT GGG GAG
LEU ARG CYS GLN VAL GLN GLU GLY GLY PRO ARG ALA ASN LEU THR VAL VAL LEU ARG GLY GLU

AAG GAG CTG AAA CGG GAG CCA GCT GTG GGG GAG CCC GCT GAG GTC ACG ACG GTG CTG AGG
LYS GLU LEU LYS ARG GLU PRO ALA VAL GLY GLU PRO ALA GLU VAL THR THR VAL LEU ARG

AGA GAT CAC CAC GGA GCC AAT TTC TCG TGC CGC ACT GAA GAC CTG GAC CCC CAA GGG CTG GAG
ARG ASP HIS HIS GLY ALA ASN PHE SER CYS ARG THR GLU ASP LEU ASP PRO GLN GLY LEU GLU
```

| | | | | | | | | | | | | | | | | | | | | | |
|---|---|---|---|---|---|---|---|---|---|---|---|---|---|---|---|---|---|---|---|---|---|
| CTG LEU | TTT PHE | GAG GLU | AAC ASN | ACC THR | TCG SER | GCC ALA | CCC PRO | TAC TYR | CAG GLN | CTC LEU | CAG GLN | ACC THR | TTT PHE | GTC VAL | CTG LEU | CCA PRO | GCG ALA | ACT THR | CCC PRO | CCA PRO | CAA GLN |
| CTT LEU | GTC VAL | AGC SER | CCC PRO | CGG ARG | GTC VAL | CTA LEU | GAG GLU | GTG VAL | GAC ASP | ACG THR | GGG GLY | CAG GLN | ACC THR | GTG VAL | GTC VAL | TGT CYS | TCC SER | CTG LEU | GAC ASP | GGG GLY | CTG LEU |
| TTC PHE | CCA PRO | GTC VAL | TCG SER | GAG GLU | TCG SER | GCC ALA | CAG GLN | CAC HIS | CTG LEU | GCA ALA | CTG LEU | GGG GLY | GAC ASP | CAG GLN | GAC ASP | TTG LEU | AAC ASN | CCC PRO | ACA THR | GTC VAL | ACC THR |
| TAT TYR | GGC GLY | GAC ASP | TTC PHE | TCC SER | TGT CYS | GCA ALA | AAG LYS | GTC VAL | TCA SER | GCC ALA | AGT SER | GTG VAL | ACC THR | GTG VAL | CAG GLN | ACC THR | GGC GLY | GGC GLY | ACC THR | ACC THR | CAG GLN |
| CGG ARG | CTG LEU | ACG THR | TTC PHE | TGT CYS | GCA ALA | ATA ILE | CTG LEU | AAG LYS | GGG GLY | AAC ASN | CAG GLN | GAG GLU | ACA THR | CAG GLN | ACA THR | GGG GLY | ACC THR | ACC THR | ATC ILE | ACA THR | TAC TYR |
| AGC SER | TTT PHE | CCG PRO | GCG ALA | CCT PRO | AAC ASN | GTG VAL | ATT ILE | CTG LEU | CTG LEU | AAG LYS | CCA PRO | GAA GLU | GGG GLY | GTC VAL | TCA SER | GAG GLU | CGG ARG | CCA PRO | GCA ALA | GTG VAL | ACA THR |
| AAG LYS | TGT CYS | GAG GLU | GCC ALA | CAC HIS | CCT PRO | AGA ARG | CTG LEU | GCC ALA | AAG LYS | GTG VAL | ACG THR | ACG THR | AAT ASN | GGG GLY | GCC ALA | GCC ALA | TCC SER | TGC CYS | TCT SER | GCA ALA | ACC THR |
| AGG ARG | GCC ALA | CAG GLN | CTC LEU | CAC HIS | AAC ASN | AAG LYS | AAG LYS | AAG LYS | ACC THR | CCA PRO | CAG GLN | GAC ASP | GGG GLY | GAC ASP | AAC ASN | CGG ARG | TTC PHE | CTG LEU | GTC VAL | CAG GLN | CCG PRO |
| CTG LEU | GAG GLU | GTG VAL | GCC ALA | GGC GLY | CAG GLN | CTT LEU | ATA ILE | TGG TRP | GAG GLU | AAG LYS | CAC HIS | CAG GLN | GGG GLY | AAC ASN | CGG ARG | GAG GLU | CTG LEU | CTG LEU | TAT TYR | ATG MET | GGC GLY |
| CGA ARG | CTG LEU | GAC ASP | GAG GLU | AGG ARG | GAT ASP | TGT CYS | CCG PRO | CCG PRO | ACG THR | AAC ASN | ACG THR | GAA GLU | GGA GLY | AAT ASN | TCC SER | CCA PRO | CAG GLN | AAT ASN | CCA PRO | CCA PRO | ATC ILE |
| TGC CYS | CAG GLN | GCT ALA | TGG TRP | GGG GLY | AAG LYS | CTA LEU | TTG LEU | CCC PRO | ATG MET | CCC PRO | GAG GLU | CTG LEU | GAT ASP | GGC GLY | GGC GLY | ACT THR | TTC PHE | TTC PHE | CCA PRO | ATG MET | CCC PRO |
| | | | | CCA PRO | TGT CYS | AAG LYS | CCC PRO | GAG GLU | CTG LEU | CTG LEU | CTG LEU | TAC TYR | GGC GLY | CTG LEU | GCA ALA | TGC CYS | GGC GLY | TAT TYR | TGC CYS | CTG LEU | CCC PRO |

FIG. 1B

```
ATC GGG GAA TCA GTG ACT GTC ACT CGA GAT CTT GAG GGC ACC TAC CTC TGT CGG GCC AGG AGC ACT
ILE GLY GLU SER VAL THR VAL THR ARG ASP LEU GLU GLY THR TYR LEU CYS ARG ALA ARG SER THR

CAA GGG GAG GTC ACC CGC ACC GAG GTG ACC GTG AAT GTG ACC CCC CGG TAT GAG ATT GTC ATC ATC
GLN GLY GLU VAL THR ARG THR GLU VAL THR VAL ASN VAL THR LEU SER PRO ARG TYR GLU ILE VAL ILE ILE

ACT GTG GTA GCA GCC GCA GTC ATA ATG GGC ACT GCA GGC CTC AGC ACG TAC CTC TAT AAC CGC CAG
THR VAL VAL ALA ALA ALA VAL ILE MET GLY THR ALA GLY LEU SER THR TYR LEU TYR ASN ARG GLN

CGG AAG ATC AAG AAA TAC AGA CTA CAA CAG GCC CAA AAA GGG ACC CCC ATG AAA CCG AAC ACA CAA
ARG LYS ILE LYS LYS TYR ARG LEU GLN GLN ALA GLN LYS GLY THR PRO MET LYS PRO ASN THR GLN

GCC ACG CCT CCC TGA ACCTATCCCG GGACAGGGCC TCTTCCTCGG CCTTCCCATA TTGGTGGCAG TGGTGCCACA
ALA THR PRO PRO ***

CTGAACAGAG TGGAAGACAT ATGCCATGCA GCTACACCTA CCGGCCCTGG GACGCCGGAG GACAGGGCAT TGTCCTCAGT

CAGATACAAC AGCATTTGGG GCCATGGTAC CTGCACACCT AAAACACTAG GCCACGCATC TGATCTGTAG TCACATGACT

AAGCCAAGAG GAAGGAGCAA GACTCAAGAC ATGATTGATG GATGTTAAAG TCTAGCCTGA TGAGAGGGGA AGTGGTGGGG

GAGACATAGC CCCACCATGA GGACATACAA CTGAAACTTG CTGCCTATTG GGTATGCTGA GGCCCACAGA

CTTACAGAAG AAGTGGCCCT CCATAGACAT GTGTAGCATC AAAACACAAA GGCCACACT TCCTGACGGA TGCCAGCTTG

GGCACTGCTG TCTACTGACC CCAACCCTTG ATGATATGTA TTTATTCATT TGTTATTTTA CCAGCTATTT ATTGAGTGTC

TTTTATGTAG GCTAAATGAA CATAGGTCTC TGGCCTCACG GAGCTCCCAG TCCATGTCAC ATTCAAGTCC ACCAGGTACA

GTTGTACAGG TTGTACACTG CAGGAGAGTG CCTGGCAAAA AGATCAAATG GGGCTGGGAC TTCTCATTGG CCAACCTGCC

TTTCCCCAGA AGGAGTGATT TTTCTATCGG CACAAAAGCA CTATATGGAC TGGTAATGGT TCACAGGTTC AGAGATTACC
```

FIG. 1C

```
CAGTGAGGCC TTATTCCTCC CTTCCCCCCA AAACTGACAC CTTTGTTAGC CACCTCCCCA CCCACATACA TTTCTGCCAG
TGTTACAATG ACACTCAGCG GTCATGTCTG GACATGAGTG CCCAGGGAAT ATGCCCAAGC TATGCCTTGT CCTCTTGTCC
TGTTTGCATT TCACTGGGAG CTTGCACTAT TGCAGCTCCA GTTTCCTGCA GTGATCAGGG TCCTGCAAGC AGTGGGAAG
GGGGCCAAGG TATTGGAGGA CTCCCTCCCA GCTTTGGAAG GGTCATCCGC GTGTGTGTGT GTAGACAAGC
TCTCGCTCTG TCACCCAGGC TGGAGTGCAG TGGTGCAATC ATGGTTCACT GCAGTCTTGA CCTTTGGGC TCAAGTGATC
CTCCCACCTC AGCCTCCTGA GTAGCTGGGA CCATAGGCTC ACAACACCAC ACCTGGCAAA TTTGATTTTT TTTTTTTTTT
TCAGAGACGG GGTCTCGCCAA CATTGCCCAG ACTTCCTTTG TGTTAGTTAA TAAAGCTTTC TCAACTGCCA AAAAAAAAAA
AAAAAAA
```

TTCACATCAA AACTCCTATA CTGACCTGAG ACAGAGGCAG CAGTGATACC CACCTGAGAG ATCCTGTGTT TGA

ACAACTG CTTCCCAAAA CGGAAAGTAT TTCAAGCCTA AACCTTTGGG TGAAAAGAAC TCTTGAAGTC ATG ATT
                                                                                                                                                   met ile GCT TCA CAG TTT CTC TCA GCT CTC ACT TTG GTG CTT CTC ATT AAA GAG AGT GGA GCC TGG
ala ser gln phe leu ser ala leu thr leu val leu leu ile lys glu ser gly ala trp TCT TAC AAC ACC TCC ACG GAA GCT ATG ACT TAT GAT GAG GCC AGT GCT TAT TGT CAG CAA
ser tyr asn thr ser thr glu ala met thr tyr asp glu ala ser ala tyr cys gln gln AGG TAC ACA CAC CTG GTT GCA ATT CAA AAC AAA GAA GAG ATT GAG TAC CTA AAC TCC ATA
arg tyr thr his leu val ala ile gln asn lys glu glu ile glu tyr leu asn ser ile TTG AGC TAT TCA CCA AGT TAT TAC TGG TAT TGG ATT GGA ATC AGA AAA GTC AAC AAT GTG TGG GTC
leu ser tyr ser pro ser tyr tyr trp tyr trp ile gly ile arg lys val asn asn val trp val TGG GTA GGA ACC CAG AAA CCT CTG ACA GAA GAA GCC AAG AAC TGG GCT CCA GGT GAA CCC
trp val gly thr gln lys pro leu thr glu glu ala lys asn trp ala pro gly glu pro AAC AAT AGG CAA AAA GAT GAG GAC TGC GTG GAG ATC TAC ATC AAG AAG AGA GAA AAA GAT GTG
asn asn arg gln lys asp glu asp cys val glu ile tyr ile lys lys arg glu lys asp val GGC ATG TGG AAT GAT GAG AGG TGC AGC AAG AAG AAG CTT GCC CTA TGC CTA ACA GCT GCC
gly met trp asn asp glu arg cys ser lys lys lys leu ala leu cys tyr thr ala ala TGT ACC AAT ACA TCC AAT ACA TCC TGC CAC GGT GAA TGT GTA GAG ACC ATC AAT AAT TAC ACT
cys thr asn thr ser cys ser gly his gly glu cys val glu thr ile asn asn tyr thr TGC AAG TGT GAC CCT GGC TTC AGT GGA CTC AAG TGT GAG CAA ATT GTG AAC TGT ACA GCC
cys lys cys asp pro gly phe ser gly leu lys cys glu gln ile val asn cys thr ala

```
CTG GAA TCC CCT GAG CAT GGA AGC CTG GTT TGC AGT CAC CCA CTG GGA AAC TTC AGC TAC
leu glu ser pro glu his gly ser leu val cys ser his pro leu gly asn phe ser tyr AAT TCT TCC TGC ATC TCT AGC TGT GAT AGG GGT TAC CTG CCA AGC AGC ATG GAG ACC ATG
asn ser ser cys ser ile ser cys asp arg gly tyr leu pro ser ser met glu thr met CAG TGT ATG TCC TCT GGA GAA TGG GCT CCT ATT CCA GCC TCC AAT GTG GTT GAG TGT
gln cys met ser ser gly glu trp ala pro ile pro ala ser asn val val glu cys GAT GCT GTG ACA AAT CCA GCC AAT GGG TTC GTG GAA TGT TTC CAA AAC CCT GGA AGC TTC
asp ala val thr asn pro ala asn gly phe val glu cys phe gln asn pro gly ser phe CCA TGG AAC ACA ACC TGT TAC ACA TTT GAC TGT GAA GAA GGA TTT GAA CTA ATG GGA CAG
pro trp asn thr thr cys tyr thr phe asp cys glu glu gly phe glu leu met gly gln AGC CTT CAG TGT ACC TCA TCT GGC AAT TGG GAC AAC GAG AAG CCA TGT AAA GCT GTG
ser leu gln cys thr ser ser gly asn trp asp asn glu lys pro thr cys lys ala val ACA TGC AGG GCC GTC TTC AAA TCA CCT CGC CAG AAT GGC TCT GTG AGG TGC AGC CAT TCC CCT GCT
thr cys arg ala val arg gln pro gln asn gly ser val arg cys ser his ser pro ala GGA GAG TTC ACC TTC CAG TCC TGC TAC AAC TTC ACC TGT GAG GGC GGA TGC AGC ATG TTG CAG
gly glu phe thr phe gln ser cys tyr asn phe thr cys glu gly gly phe met leu gln GGA CCA GCC CAG GTT GAA ACT GAA TGC ACT CAA CAG GGG CAG CAG TGG CAG CAA ATC CCA GTT TGT
gly pro ala gln val glu cys thr thr gln gly gln trp gln gln ile pro val cys GAA GCT TTC CAG TGC ACA GCC TTG TCC AAC CCC GAG GGC CGA TAC ATG AAT TGT CTT CCT
glu ala phe gln cys thr ala leu ser asn pro glu gly arg gly tyr met asn cys leu pro
```

FIG. 2B

| AGT | GCT | TCT | GGC | AGT | TTC | CGT | TAT | GGG | TCC | AGC | TGT | GAG | TTC | TCC | TGT | GAG | CAG | GGT | TTT |
|---|---|---|---|---|---|---|---|---|---|---|---|---|---|---|---|---|---|---|---|
| ser | ala | ser | gly | ser | phe | arg | tyr | gly | ser | ser | cys | glu | phe | ser | cys | glu | gln | gly | phe |

| GTG | TTG | AAG | GGA | TCC | AAA | AGG | CTC | CAA | TGT | GGC | CCC | ACA | GGG | GAG | TGG | GAC | AAC | GAG | AAG |
|---|---|---|---|---|---|---|---|---|---|---|---|---|---|---|---|---|---|---|---|
| val | leu | lys | gly | ser | lys | arg | leu | gln | cys | gly | pro | thr | gly | glu | trp | asp | asn | glu | lys |

| CCC | ACA | TGT | GAA | GCT | GTG | AGA | TGC | GAT | GCT | GTC | CAC | CAG | CCC | AAG | GGT | TTG | GTG | AGC |
|---|---|---|---|---|---|---|---|---|---|---|---|---|---|---|---|---|---|---|
| pro | thr | cys | glu | ala | val | arg | cys | asp | ala | val | his | gln | pro | lys | gly | leu | val | arg |

| TGT | GCT | CAT | TCC | CCT | ATT | GGA | GAA | TTC | ACC | TAC | AAG | TCC | TGT | GCC | TTC | AGC | TGT | GAG |
|---|---|---|---|---|---|---|---|---|---|---|---|---|---|---|---|---|---|---|
| cys | ala | his | ser | pro | ile | gly | glu | phe | thr | tyr | lys | ser | cys | ala | phe | ser | cys | glu |

| GAG | GGA | TTT | GAA | TTA | TAT | GGA | TCA | ACT | CAA | CTT | GAG | TGC | ACA | TCT | CAG | GTT | CAG | CAA | ATC |
|---|---|---|---|---|---|---|---|---|---|---|---|---|---|---|---|---|---|---|---|
| glu | gly | phe | glu | leu | tyr | gly | ser | thr | gln | leu | glu | cys | thr | ser | gln | val | gln | lys | ile |

| GAA | GAG | GTT | CCT | TCC | TGC | CAA | GTA | GTA | GTG | TGT | TCA | AGC | CTG | GCA | GTT | CCG | GGA | AAG | ATC |
|---|---|---|---|---|---|---|---|---|---|---|---|---|---|---|---|---|---|---|---|
| glu | glu | val | pro | ser | cys | gln | val | val | val | cys | ser | ser | leu | ala | val | pro | gly | lys | ile |

| AAC | ATG | AGC | TGC | AAT | GGC | TCT | GCA | GCT | CCC | GTG | TTT | GGC | ACT | GTG | TGC | AAG | TTC | GCC | TGT | CCT | GAA |
|---|---|---|---|---|---|---|---|---|---|---|---|---|---|---|---|---|---|---|---|---|---|
| asn | met | ser | cys | asn | gly | ser | ala | ala | pro | val | phe | gly | thr | val | cys | lys | phe | ala | cys | pro | glu |

| GGA | TGG | ACG | CTC | AAT | GGC | TCT | GCA | GCT | CGG | ACA | TGT | GGA | GCC | ACA | GGA | CAC | TGG | GTA | GCT | TCT | GGC |
|---|---|---|---|---|---|---|---|---|---|---|---|---|---|---|---|---|---|---|---|---|---|
| gly | trp | thr | leu | asn | gly | ser | ala | ala | arg | thr | cys | gly | ala | thr | gly | his | trp | val | ala | ser | gly |

| CTG | CTA | CCT | ACC | TGT | GAA | GCT | CCC | ACT | GAG | TCC | AAC | ATT | CCC | TTG | GTA | GCT | GGA | CTT | TCT |
|---|---|---|---|---|---|---|---|---|---|---|---|---|---|---|---|---|---|---|---|
| leu | leu | pro | thr | cys | glu | ala | pro | thr | glu | ser | asn | ile | pro | leu | val | ala | gly | leu | ser |

| GCT | GCT | GGA | CTC | TCC | CTC | CTG | ACA | CCA | TTA | GCA | CCA | TTT | CTC | CTC | TGG | CGG | AAA | TGC | TTA |
|---|---|---|---|---|---|---|---|---|---|---|---|---|---|---|---|---|---|---|---|
| ala | ala | gly | leu | ser | leu | leu | thr | pro | leu | ala | pro | phe | leu | leu | trp | arg | lys | cys | leu |

| CGG | AAA | GCA | AAG | TTT | GTT | CCT | GCC | AGC | TGC | CAA | AGC | TGC | CTT | GAA | TCA | GAC | GGA | AGC |
|---|---|---|---|---|---|---|---|---|---|---|---|---|---|---|---|---|---|---|
| arg | lys | ala | lys | lys | phe | val | pro | ala | ser | cys | gln | ser | cys | leu | glu | ser | asp | gly | ser |

FIG. 2C

TAC CAA AAG CCT TCT TAC ATC CTT TAA GTTCAAA AGAATCAGAA ACAGGTGCAT CTGGGAACT A
tyr gln lys pro ser tyr ile leu ***

GAGGGATAC ACTGAAGTTA ACAGAGACAG ATAACTCTCC TCGGGTCTCT GGCCCTTCTT GCCTACTATG CCAG

ATCCCT TTATGGCTGA AACCGCAACA CCCATCACCA CTTCAATAGA TCAAAGTCCA GCAGGCAAGG ACGGCCT

TCA ACTGAAAAGA CTCAGTGTTC CCTTTCCTAC TCTCAGGATC AAGAAAGTGT TGGCTAATGA AGGGAAGGA

TATTTCTTC CAAGCAAGG TGAAGAGACC AAGACTCTGA AATCTCAGAA TTCCTTTCT AACTCTCCCT TG

CTCGCTGT AAATCTTGG CACAGAAACA CAATATTTG TGGCTTTCTT TCTTTTGCCC TTCACAGTGT TTGA

CAGCT GATTACACAG TTGCTGTCAT AAGAATGAAT AATAATTATC CAGAGTTTAG AGGAAAAAA TGACTAAA

AA TATTATAACT TAAAAAAATG ACAGATGTTG AATGCCCACA GGCAAATGCA TGGAGGGTTG TTAATGGTGC

AAATCCTACT GAATGCTCTG TCCGAGGGTT ACTATGCCACA ATTTAATCAC TTTCATCCCT ATGGGATTCA GTG

CTTCTTA AAGAGTTCTT AAGGATTGTG ATATTTTTAC TTGCATTGAA TATATTATAA TCTTCCATAC TTCTTC

ATTC AATACAAGTG TGGTAGGGAC TTAAAAAACT TGTAAATGCT GTCAACTATG ATATGGTAAA AGTTACTTA

T TCTAGATTAC CCCCTCATTG TTTATTAACA AATTATGTTA CATCTGTTT AAATTTATTT CAAAAAGGA A

ACTATTGTC CCCTAGCAAG GCATGATGTT AACCAGAATA AAGTTCTGAG TGTTTTTACT ACAGTTGTTT TTTG

AAAACA TGGTAGAATT GGAGAGTAAA AACTGAATGG AAGGTTTGTA TATTGTCAGA TATTTTTCA GAAATAT

GTG GTTCCACGA TGAAAAACTT CCATGAGGCC AAACGTTTTG AACTAATAAA AGCATAAATG CAAACACACA

AAGGTATAAT TTTATGAATG TCTTTGTTGG AAAAGAATAC AGAAAGATGG ATGTGCTTTG CATTCCTACA AA

GATGTTTG TCAGATGTGA TATGTAAACA TAATTCTTGT ATATTATGGA AGATTTTAAA TTCACAATAG AAACT

FIG. 2D

```
CACCA TGTAAAAGAG TCATCTGGTA GATTTTTAAC GAATGAAGAT GTCTAATAGT TATTCCCTAT TTGTTTTC
TT CTGTATGTTA GGGTGCTCTG GAAGAGAGGA ATGCCTGTGT GAGCAAGCAT TTATGTTTAT TTATAAGCAG
ATTAACAAT TCCAAAGGAA TCTCCAGTTT TCAGTTGATC ACTGGCAATG AAAAATTCTC AGTCAGTAAT TGC
CAAAGCT GCTCTAGCCT TGAGGAGTGT GAGAATCAAA ACTCTCCCTAC ACTTCCATTA ACTTAGCATG TGTTGA
AAAA AAAAGTTTCA GAGAAGTTCT GGCTGAACAC TGGCAACGAC AAAGCCAACA GTCAAAACAG AGATGTGAT
A AGGATCAGAA CAGCAGAGGT TCTTTTAAAG GGGCAGAAAA ACTCTGGGAA ATAAGAGAGA ACAACTACTG T
GATCAGGCT ATGTATGGAA TACAGTGTTA TTTTCTTTGA AATTGTTTAA GTGTTGTAAA TATTTATGTA AACT
GCCATTA GAAATTAGCT GTGTGAAATA CCAGTGTGGT TTGTGTTTGA GTTTTATTGA GAATTTTAAA TTATAAC
TTA AAATATTTTA TAATTTTTAA AGTATATATT TATTTAAGCT TATGTCAGAC CTATTTGACA TAACACTATA
AAGGTTGACA ATAAATGTGC TTATGTTT
```

```
CGGGCCTCAC TGGCTTCAGG AGCTGAATAC CCTCCCAGGC ACACACAGGT GGGACACAAA TAAGGGTTTT GGA

ACCACTA TTTTCTCATC ACGACAGCAA CTTAAA ATG CCT GGG AAG ATG GTC GTG ATC CTT GGA GCC
                                        met pro gly lys met val val ile leu gly ala TCA AAT ATA CTT TGG ATA ATG TTT GCA GCT TCT CAA GCT TTT AAA ATC GAG ACC ACC CCA
ser asn ile leu trp ile met phe ala ala ser gln ala phe lys ile glu thr thr pro GAA TCT AGA TAT CTT GCT CAG ATT GGT GAC TCC TCA TTG ACT TGC AGC ACC ACA GGC
glu ser arg tyr leu ala gln ile gly asp ser val ser leu thr cys ser thr thr gly TGT GAG TCC CCA TTT TTC TCT TGG AGA ACC CAG ATA GAT AGT CCA CTG AAT GGG AAG GTG
cys glu ser pro phe phe ser trp arg thr gln ile asp ser pro leu asn gly lys val ACG AAT GAG GGG ACC ACA TCT ACG CTG ACA ATG AAT CCT GTT AGT TTT GGG AAC GAA CAC
thr asn glu gly thr thr ser thr leu thr met asn pro val ser phe gly asn glu his TCT TAC CTG TGC ACA GCA ACT TGT GAA TCT AGG AAA TTG GAA AAA GGA ATC CAG GTG GAG
ser tyr leu cys thr ala thr cys glu ser arg lys leu glu lys gly ile gln val glu ATC TAC TCT TTT CCT AAG GAT CCA GAG ATT CAT TTG AGT GGC CCT CTG GAG GCT GGG AAG
ile tyr ser phe pro lys asp pro glu ile his leu ser gly pro leu glu ala gly lys CCG ATC ACA GTC AAG TGT TCA GTT GCT GAT GTA TAC CCA TTT GAC AGG CTG GAG ATA GAC
pro ile thr val lys cys ser val ala asp val tyr pro phe asp arg leu glu ile asp TTA CTG AAA GGA GAT CAT CTC ATG AAG AGT CAG GAA TTT CTG GAG GAT GCA GAC AGG AAG
leu leu lys gly asp his leu met lys ser gln glu phe leu glu asp ala asp arg lys TCC CTG GAA ACC AAG TTG GAA GTA ACC TTT ACT CCT GTC ATT GAG GAT ATT GGA AAA
ser leu glu thr lys leu glu val thr phe thr pro val ile glu asp ile gly lys GTT CTT GTT TGC CGA GCT AAA TTA CAC ATT GAT GAA ATG GAT TCT GTG CCC ACA GTA AGG
val leu val cys arg ala lys leu his ile asp glu met asp ser val pro thr val arg
```

CAG GCT GTA AAA GAA TTG CAA GTC TAC ATA TCA CCC AAG AAT ACA GTT ATT TCT GTG AAT
gln ala val lys glu leu gln val tyr ile ser pro lys asn thr val ile ser val asn CCA TCC ACA AAG CTG CAA GAA GGT GGC TCT GTG ACC ATG ACC TGT TCC AGC GAG GGT CTA
pro ser thr lys leu gln glu gly gly ser val thr met thr cys ser ser glu gly leu CCA CCT CCA GAG ATT TTC TGG AGT AAA AAA TTA GAT AAT GGG AAT CTA CAG CAC CTT TCT
pro ala pro glu ile phe trp ser lys lys leu asp asn gly asn leu gln his leu ser GGA AAT GCA ACT CTC ATT GGG TTA ATT GCT ATG AGG ATG GAA GAT TCT GGA ATT TAT GTG TGT
gly asn ala thr leu ile gly leu ile ala met arg met glu asp ser gly ile tyr val cys GAA GTT ATT GGG AAA AAC AGA AAA GAG GTG GAA TTA ATT GTT CAA GCA TTC
glu val ile gly lys asn arg lys glu val glu leu ile val gln ala phe CCT AGA GAT CCA ATC GAG ATG AGT GGT GGC CTC GTG AAT GGG AGC TCT GTC ACT GTA
pro arg asp pro ile glu met ser gly gly leu val asn gly ser ser val thr val AGC TGC AAG GTT CCT AGC GTG TAC CCC CTT GAC CGG ATT GAA TTA CTT AAG GGG
ser cys lys val pro ser val tyr pro leu asp arg ile glu leu leu lys gly GAG ACT ATT CTG GAG AAT ATA GAG TTT TTG GAG GAT ATG ACG GAT ACT GGA AAA TCT CTA GAG AAC
glu thr ile leu glu asn ile glu phe leu glu asp met thr asp thr gly lys ser leu glu asn AAA AGT TTG GAA ATG ACC TTC ATC CCT ACC ATT GAA GAT ACT GGA AAA GCT CTT GTT TGT
lys ser leu glu met thr phe ile pro thr ile glu asp thr gly lys ala leu val cys CAG GCT AAG TTA CAT ATT GAT GAC ATG GAA TTC GAA CCC AAA CAA AGG CAG AGT ACG CAA
gln ala lys leu his ile asp asp met glu phe glu pro lys gln arg gln ser thr gln ACA CTT TAT GTC AAT GTT GCC AGA GAT GCC ACA GAT ACC GTC TTG GTC CCT AGC TCC ATC
thr leu tyr val asn val ala pro arg asp ala thr val leu val pro ser ser ile CTG GAG GAA GGC AGT ACA ATG ATG ACA TGC CGG GCG TTT CCT CCT GCT CCG AAA
leu glu glu gly ser thr met met thr cys arg ala phe pro pro ala pro lys

FIG. 3B

```
ATC CTG TGG AGC AGG CAG CTC CCT AAC GGG GAG CTA CAG CCT CTT TCT GAG AAT GCA ACT
ile leu trp ser arg gln leu pro asn gly glu leu gln pro leu ser glu asn ala thr CTC ACC TTA ATT TCT ACA AAA ATG GAA GAT TCT GGG GTT TAT TTA TGT GAA GGA ATT AAC
leu thr leu ile ser thr lys met glu asp ser gly val tyr leu cys glu gly ile asn CAG GCT GGA AGA AGC AGA GAA GTG GAA TTA ATT CAA GTT ACT CCA AAA GAC ATA
gln ala gly arg ser arg lys glu val glu leu ile ile gln val thr pro lys asp ile AAA CTT ACA GCT TTT CCT GAG AGT GTC AAA GAA GCA GAC ACT GTC ATC ATC TCT TGT
lys leu thr ala phe pro ser glu ser val lys glu gly asp thr val ile ile ser cys ACA TGT GGA AAT GTT CCA GAA ACA TGG ATA ATC ATC CTG AAG AAA AAA AAA GCG GAG GAC
thr cys gly asn val pro glu thr trp ile ile ile leu lys lys lys ala glu gly asp ACA GTA CTA AAA TCT ATA GAT GGC GCC TAT ACC ATC CGA AAG AAG CAG TTG AAG GAT GCG
thr val leu lys ser ile asp gly ala tyr thr ile arg lys lys ala gln leu lys asp ala GGA GTA TAT GAA TGT AAA AAC GTT GGC TCA CAA GTT TTA AGA AGT TTA ACA CTT
gly val tyr glu cys lys asn lys val gly ser gln leu arg ser leu thr leu GAT GTT CAA GGA AGA GAA AAC GAC TAT TTT TCT CCT GAG CTT CTC GTG CTC TAT
asp val gln gly arg glu asn asp tyr phe ser pro glu leu leu val leu tyr TTT GCA TCC TTA ATA ATA CCT GCC ATT GGA ATC ATA TTT GCA GCA CAG AAA TCA AAA GTG TAG CTAATGCTTG
phe ala ser leu ile ile pro ala ile gly met ile tyr phe ala arg lys ala ***

AAC ATC AAG GGG TCA TAT ACT CTT GTA GAA GCA CAG AAA TCA AAA GTG TAG CTAATGCTTG
asn met lys gly ser tyr ser leu val glu val gln ala gln lys ser lys val ***

ATATGTTCAA CTGGAGACAC TATTTATCTG TGCAAATCCT TGATACTGCT CATCATTCCT TGAGAAAAC AAT

GAGCTGA GAGGCAGACT TCCCTGAATG TATTGAACTT GGAAGAAAT GCCCATCTAT GTCCCTTGCT GTGAGC

AAGA AGTCAAAGTA AAACTTGCTG CCTGAAGAAC AGTAACTCCC ATCAAGATGA GAGAACTGGA GGAGTTCCT

T GATCTGTATA TACAATAACA TAATTTCTAC ATATGTAAAA TAAAATTATG CCATAGCAAG ATTGCTAAAA
```

FIG. 3C

TAGCAACAC TCTATATTTA GATTGTTAAA ATAACTAGTG TTGCTTGGAC TATTATAATT TAATGCATGT TAGG

AAAATT TCACATTAAT ATTTGCTCAC AGCTGACCTT TGTCATCTTT CTTCTATTTT ATTCCCTTTC ACAAAAT

TTT ATTCCTATAT AGTTTATTGA CAATAATTTC AGGTTTTGTA AAGATGCCGG GTTTTATATT TTTATAGACA

AATAATAAGC AAAGGGAGCA CTGGGTTGAC TTTCAGGTAC TAAATACCTC AACCTATGGT ATAAATGGTTG AC

TGGGTTTC TCTGTATAGT ACTGGCATGG TACGGAGATG TTTCACGAAG TTTGTTCATC AGACTCCTGT GCAAC

TTTCC CAATGTGGCC TAAAAATGCA ACTTCTTTTT ATTTCTTTT GTAAATGTTT AGGTTTTTTT GTATAGTA

AA GTGATAATTT CTGGAATTAA AAA

FIG. 3D

OLIGONUCLEOTIDE MODULATION OF CELL ADHESION

This application is a continuation-in-part of application Ser. No. 09/659,288, filed Sep. 12, 2000 (abandoned), which is a continuation of application Ser. No. 09/128,496, filed Aug. 3, 1998 (U.S. Pat. No. 6,169,079), which is a continuation of application Ser. No. 08/440,740, filed May 12, 1995 (U.S. Pat. No. 5,843,738), which is a continuation-in-part of application Ser. No. 08/063,167 filed May 17, 1993 (U.S. Pat. No. 5,514,788), which is a continuation of application Ser. No. 07/969,151 filed Feb. 10, 1993 (abandoned), which is a continuation-in-part of application Ser. No. 08/007,997 filed Jan. 21, 1993 (U.S. Pat. No. 5,591,623). The entire contents of these applications and patents is incorporated herein by reference.

FIELD OF THE INVENTION

This invention relates to diagnostics, research reagents and therapies for disease states which respond to modulation of the synthesis or metabolism of cell adhesion molecules. In particular, this invention relates to antisense oligonucleotide interactions with certain messenger ribonucleic acids (mRNAs) or DNAs involved in the synthesis of proteins that regulate adhesion of white blood cells to other white blood cells and to other cell types. Antisense oligonucleotides designed to hybridize to the mRNA encoding intercellular adhesion molecule-1 (ICAM-1), endothelial leukocyte adhesion molecule-1 (ELAM-1, also known as E-selectin), and vascular cell adhesion molecule-1 (VCAM-1) are provided. These oligonucleotides have been found to lead to the modulation of the activity of the RNA or DNA, and thus to the modulation of the synthesis and metabolism of specific cell adhesion molecules. Palliation and therapeutic effect result.

BACKGROUND OF THE INVENTION

Inflammation is a localized protective response elicited by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue. Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. The adhesion of these leukocytes, or white blood cells, to vascular endothelium is an obligate step in the migration out of the vasculature. Harlan, J. M., *Blood* 1985, 65, 513–525. In general, the first inflammatory cells to appear at the site of inflammation are neutrophils followed by monocytes, and lymphocytes. Cell-cell interactions are also critical for propagation of both B-lymphocytes and T-lymphocytes resulting in enhanced humoral and cellular immune responses, respectively.

The adhesion of white blood cells to vascular endothelium and other cell types is mediated by interactions between specific proteins, termed "adhesion molecules," located on the plasma membrane of both white blood cells and vascular endothelium. The interaction between adhesion molecules is similar to classical receptor ligand interactions with the exception that the ligand is fixed to the surface of a cell instead of being soluble. The identification of patients with a genetic defect in leukocyte adhesion has enabled investigators to identify a family of proteins responsible for adherence of white blood cells. Leukocyte adhesion deficiency (LAD) is a rare autosomal trait characterized by recurrent bacterial infections and impaired pus formation and wound healing. The defect was shown to occur in the common B-subunit of three heterodimeric glycoproteins, Mac-1, LFA-1, and p150,95, normally expressed on the outer cell membrane of white blood cells. Anderson and Springer, *Ann. Rev. Med.* 1987, 38, 175–194. Patients suffering from LAD exhibit a defect in a wide spectrum of adherence-dependent functions of granulocytes, monocytes, and lymphocytes. Three ligands for LFA-1 have been identified, intercellular adhesion molecules 1, 2 and 3 (ICAM-1, ICAM-2 and ICAM-3). Both Mac-1 and p150,95 bind complement fragment C3bi and perhaps other unidentified ligands. Mac-1 also binds ICAM-1.

Other adhesion molecules have been identified which are involved in the adherence of white blood cells to vascular endothelium and subsequent migration out of the vasculature. These include endothelial leukocyte adhesion molecule-1 (ELAM-1), vascular cell adhesion molecule-1 (VCAM-1) and granule membrane protein-140 (GMP-140) and their respective receptors. The adherence of white blood cells to vascular endothelium appears to be mediated in part if not in toto by the five cell adhesion molecules ICAM-1, ICAM-2, ELAM-1, VCAM-1 and GMP-140. Dustin and Springer, *J. Cell Biol.* 1987, 107, 321–331. Expression on the cell surface of ICAM-1, ELAM-1, VCAM-1 and GMP-140 adhesion molecules is induced by inflammatory stimuli. In contrast, expression of ICAM-2 appears to be constitutive and not sensitive to induction by cytokines. In general, GMP-140 is induced by autocoids such as histamine, leukotriene $B_4$, platelet activating factor, and thrombin. Maximal expression on endothelial cells is observed 30 minutes to 1 hour after stimulation, and returns to baseline within 2 to 3 hours. The expression of ELAM-1 and VCAM-1 on endothelial cells is induced by cytokines such as interleukin-1β and tumor necrosis factor, but not gamma-interferon. Maximal expression of ELAM-1 on the surface of endothelial cells occurs 4 to 6 hours after stimulation, and returns to baseline by 16 hours. ELAM-1 expression is dependent on new mRNA and protein synthesis. Elevated VCAM-1 expression is detectable 2 hours following treatment with tumor necrosis factor, is maximal 8 hours following stimulation, and remains elevated for at least 48 hours following stimulation. Rice and Bevilacqua, *Science* 1989, 246, 1303–1306. ICAM-1 expression on endothelial cells is induced by cytokines interleukin-1 tumor necrosis factor and gamma-interferon. Maximal expression of ICAM-1 follows that of ELAM-1 occurring 8 to 10 hours after stimulation and remains elevated for at least 48 hours.

GMP-140 and ELAM-1 are primarily involved in the adhesion of neutrophils to vascular endothelial cells. VCAM-1 primarily binds T and B lymphocytes. In addition, VCAM-1 may play a role in the metastasis of melanoma, and possibly other cancers. ICAM-1 plays a role in adhesion of neutrophils to vascular endothelium, as well as adhesion of monocytes and lymphocytes to vascular endothelium, tissue fibroblasts and epidermal keratinocytes. ICAM-1 also plays a role in T-cell recognition of antigen presenting cell, lysis of target cells by natural killer cells, lymphocyte activation and proliferation, and maturation of T cells in the thymus. In addition, recent data have demonstrated that ICAM-1 is the cellular receptor for the major serotype of rhinovirus, which account for greater than 50% of common colds. Staunton et al., *Cell* 1989, 56, 849–853; Greve et al., *Cell* 1989, 56, 839–847.

Expression of ICAM-1 has been associated with a variety of inflammatory skin disorders such as allergic contact dermatitis, fixed drug eruption, lichen planus, and psoriasis; Ho et al., *J. Am. Acad. Dermatol.* 1990, 22, 64–68; Griffiths and Nickoloff, *Am. J. Pathology* 1989, 135, 1045–1053; Lisby et al., *Br. J. Dermatol.* 1989,120, 479–484; Shiohara et al., *Arch. Dermatol.* 1989, 125, 1371–1376. In addition, ICAM-1 expression has been detected in the synovium of patients with rheumatoid arthritis; Hale et al., *Arth. Rheum.* 1989, 32, 22–30, pancreatic B-cells in diabetes; Campbell et al., *Proc. Natl. Acad. Sci. U.S.A.* 1989, 86, 4282–4286; thyroid follicular cells in patients with Graves' disease; Weetman et al.,*J. Endocrinol.* 1989, 122, 185–191; and with renal and liver allograft rejection; Faull and Russ, *Transplantation* 1989, 48, 226–230; Adams et al., *Lancet* 1989, 1122–1125. ICAM-1 is also expressed on corneal endothelial cells and is induced on corneal endothelial cells in response to inflammatory stimuli.

It is has been hoped that inhibitors of ICAM-1, VCAM-1 and ELAM-1 expression would provide a novel therapeutic class of anti-inflammatory agents with activity towards a variety of inflammatory diseases or diseases with an inflammatory component such as asthma, rheumatoid arthritis, allograft rejections, inflammatory bowel disease, various dermatological conditions, and psoriasis. In addition, inhibitors of ICAM-1, VCAM-1, and ELAM-1 may also be effective in the treatment of colds due to rhinovirus infection, AIDS, Kaposi's sarcoma and some cancers and their metastasis. To date, there are no known therapeutic agents which effectively prevent the expression of the cellular adhesion molecules ELAM-1, VCAM-1 and ICAM-1. The use of neutralizing monoclonal antibodies against ICAM-1 in animal models provide evidence that such inhibitors if identified would have therapeutic benefit for asthma; Wegner et al., *Science* 1990, 247, 456–459, renal allografts; Cosimi et al.,*J. Immunol.* 1990, 144, 4604–4612, and cardiac allografts; Isobe et al., *Science* 1992, 255, 1125–1127. The use of a soluble form of ICAM-1 molecule was also effective in preventing rhinovirus infection of cells in culture. Marlin et al., *Nature* 1990, 344, 70–72.

Current agents which affect intercellular adhesion molecules include synthetic peptides, monoclonal antibodies, and soluble forms of the adhesion molecules. To date, synthetic peptides which block the interactions with VCAM-1 or ELAM-1 have not been identified. Monoclonal antibodies may prove to be useful for the treatment of acute inflammatory response due to expression of ICAM-1, VCAM-1 and ELAM-1. However, with chronic treatment, the host animal develops antibodies against the monoclonal antibodies thereby limiting their usefulness. In addition, monoclonal antibodies are large proteins which may have difficulty in gaining access to the inflammatory site. Soluble forms of the cell adhesion molecules suffer from many of the same limitations as monoclonal antibodies in addition to the expense of their production and their low binding affinity. Thus, there is a long felt need for molecules which effectively inhibit intercellular adhesion molecules. Antisense oligonucleotides avoid many of the pitfalls of current agents used to block the effects of ICAM-1, VCAM-1 and ELAM-1.

PCT/US90/02357 (Hession et al.) discloses DNA sequences encoding Endothelial Adhesion Molecules (ELAMs), including ELAM-1 and VCAM-1 and VCAM-1b. A number of uses for these DNA sequences are provided, including (1) production of monoclonal antibody preparations that are reactive for these molecules which may be used as therapeutic agents to inhibit leukocyte binding to endothelial cells; (2) production of ELAM peptides to bind to the ELAM ligand on leukocytes which, in turn, may bind to ELAM on endothelial cells, inhibiting leukocyte binding to endothelial cells; (3) use of molecules binding to ELAMS (such as anti-ELAM antibodies, or markers such as the ligand or fragments of it) to detect inflammation; (4) use of ELAM and ELAM ligand DNA sequences to produce nucleic acid molecules that intervene in ELAM or ELAM ligand expression at the translational level using antisense nucleic acid and ribozymes to block translation of a specific MRNA either by masking MRNA with antisense nucleic acid or cleaving it with a ribozyme. It is disclosed that coding regions are the targets of choice. For VCAM-1, AUG is believed to be most likely; a 15-mer hybridizing to the AUG site is specifically disclosed in Example 17.

In the United States, 40,000 corneal transplants are performed per year. Human corneal allograft rejection is a major problem in corneal clinical practice. To date, no totally reliable and reproducible medication regimen provides assurance that allograft rejection will not occur in high risk patients, including those with corneal neovascularization and previous rejections. Corneal transplants require months of meticulous follow-up care, and significantly restrict the physical activity of recipients. In addition, corneal transplantation often necessitates general anesthesia and is very expensive. Therefore, allograft rejection presents significant personal, economic and anesthetic risks to patients. Thus, there is a need for compositions and methods which will prevent corneal allograft rejection.

BRIEF DESCRIPTION OF THE DRAWINGS

FIG. 1 is the mRNA sequence of human intercellular adhesion molecule-1 (ICAM-1) (SEQ ID NO:87) and amino acid sequence encoded thereby (SEQ ID NO:88).

FIG. 2 is the mRNA sequence of human endothelial leukocyte adhesion molecule-1 (ELAM-1) (SEQ ID NO:89) and amino acid sequence encoded thereby (SEQ ID NO:90).

FIG. 3 is the mRNA sequence of human vascular cell adhesion molecule-1 (VCAM-1) (SEQ ID NO:91) and amino acid sequence encoded thereby (SEQ ID NO:92).

SUMMARY OF THE INVENTION

Figure 4:
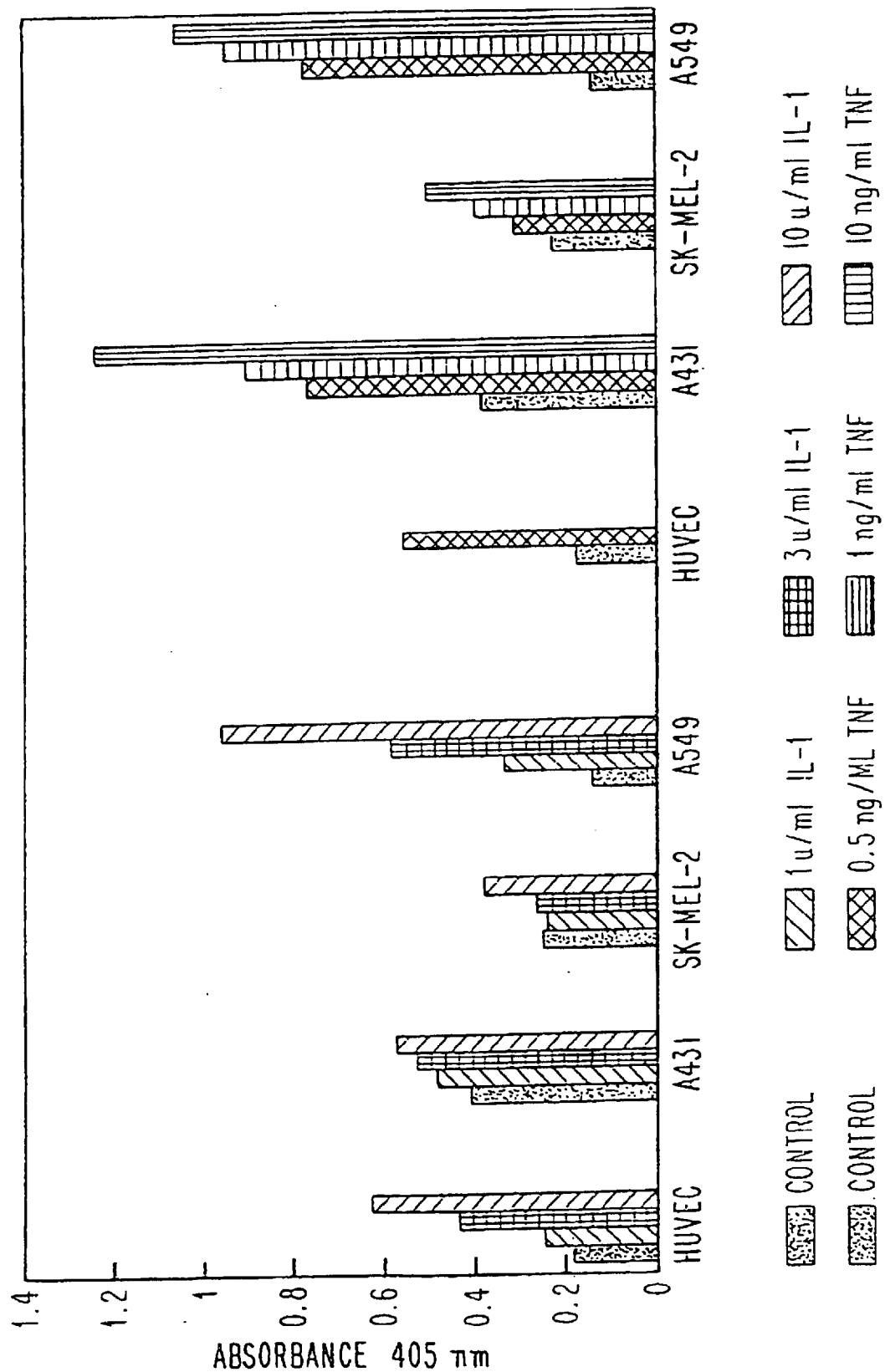
FIG. 4 is a graphical representation of the induction of ICAM-1 expression on the cell surface of various human cell lines by interleukin-1 and tumor necrosis factor.

In accordance with the present invention, oligonucleotides are provided which specifically hybridize with nucleic acids encoding intercellular adhesion molecule-1 (ICAM-1), vascular cell adhesion molecule-1 (VCAM-1) and endothelial leukocyte adhesion molecule-1 (ELAM-1). The oligonucleotides are designed to bind either directly to mRNA or to a selected DNA portion forming a triple stranded structure, thereby modulating the amount of mRNA made from the gene. This relationship is commonly denoted as "antisense."

Oligonucleotides are commonly used as research reagents and diagnostics. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed for research use. This specificity and sensitivity is also harnessed by those of skill in the art for diagnostic uses.

It is preferred to target specific genes for antisense attack. "Targeting" an oligonucleotide to the associated ribonucleotides, in the context of this invention, is a multi-step process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a cellular gene associated with a particular disease state. The targeting process also includes determination of a site or sites within this region for the oligonucleotide interaction to occur such that the desired effect, either detection of or modulation of expression of the protein will result. Once the target site or sites have been identified, oligonucleotides are chosen which are sufficiently complementary to the target, i.e., hybridize sufficiently well and with sufficient specificity, to give the desired effect.

It has been discovered that the genes coding for ICAM-1, VCAM-1 and ELAM-1 are particularly useful for this approach. Inhibition of ICAM-1, VCAM-1 and ELAM-1 expression is expected to be useful for the treatment of inflammatory diseases, diseases with an inflammatory component, allograft rejection, psoriasis and other skin diseases, inflammatory bowel disease, cancers and their metastasis, and viral infections.

Methods of modulating cell adhesion comprising contacting the animal with an oligonucleotide hybridizable with nucleic acids encoding a protein capable of modulating cell adhesion are provided. Oligonucleotides hybridizable with an RNA or DNA encoding ICAM-1, VCAM-1 and ELAM-1 are preferred.

The present invention is also useful in diagnostics and in research. Since the oligonucleotides of this invention hybridize to ICAM-1, ELAM-1 or VCAM-1, sandwich and other assays can easily be constructed to exploit this fact. Provision of means for detecting hybridization of an oligonucleotide with one of these intercellular adhesion molecules present in a sample suspected of containing it can routinely be accomplished. Such provision may include enzyme conjugation, radiolabelling or any other suitable detection system. A number of assays may be formulated employing the present invention, which assays will commonly comprise contacting a tissue sample with a detectably labeled oligonucleotide of the present invention under conditions selected to permit hybridization and measuring such hybridization by detection of the label.

For example, radiolabeled oligonucleotides can be prepared by $^{32}P$ labeling at the 5' end with polynucleotide kinase. Sambrook et al., *Molecular Cloning. A Laboratory Manual*, Cold Spring Harbor Laboratory Press, 1989, Volume 2, pg. 10.59. Radiolabeled oligonucleotides are then contacted with tissue or cell samples suspected of containing an intercellular adhesion molecule and the sample is washed to remove unbound oligonucleotide. Radioactivity remaining in the sample indicates bound oligonucleotide (which in turn indicates the presence of an intercellular adhesion molecule) and can be quantitated using a scintillation counter or other routine means. Expression of these proteins can then be detected.

Radiolabeled oligonucleotides of the present invention can also be used to perform autoradiography of tissues to determine the localization, distribution and quantitation of intercellular adhesion molecules for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a intercellular adhesion molecule. Quantitation of the silver grains permits expression of these molecules to be detected and permits targeting of oligonucleotides to these areas.

Analogous assays for fluorescent detection of expression of intercellular adhesion molecules can be developed using oligonucleotides of the present invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va.).

Each of these assay formats is known in the art. One of skill could easily adapt these known assays for detection of expression of intercellular adhesion molecules in accordance with the teachings of the invention providing a novel and useful means to detect expression of these molecules. Antisense oligonucleotide inhibition of the expression of intercellular adhesion molecules in vitro is useful as a means to determine a proper course of therapeutic treatment. For example, before a patient is treated with an oligonucleotide composition of the present invention, cells, tissues or a bodily fluid from the patient can be treated with the oligonucleotide and inhibition of expression of intercellular adhesion molecules can be assayed. Effective in vitro inhibition of the expression of molecules in the sample indicates that the expression will also be modulated in vivo by this treatment.

Kits for detecting the presence or absence of intercellular adhesion molecules may also be prepared. Such kits include an oligonucleotide targeted to ICAM-1, ELAM-1 or VCAM-1.

The oligonucleotides of this invention may also be used for research purposes. Thus, the specific hybridization exhibited by the oligonucleotides may be used for assays, purifications, cellular product preparations, and in other methodologies which may be appreciated by persons of ordinary skill in the art.

DETAILED DESCRIPTION OF PREFERRED EMBODIMENTS

Antisense oligonucleotides hold great promise as therapeutic agents for the treatment of many human diseases. Oligonucleotides specifically bind to the complementary sequence of either pre-mRNA or mature mRNA, as defined by Watson-Crick base pairing, inhibiting the flow of genetic information from DNA to protein. The properties of antisense oligonucleotides, which make them specific for their target sequence, also make them extraordinarily versatile. Because antisense oligonucleotides are long chains of four monomeric units they may be readily synthesized for any target RNA sequence. Numerous recent studies have documented the utility of antisense oligonucleotides as biochemical tools for studying target proteins. Rothenberg et al., *J. Natl. Cancer Inst.* 1989, 81, 1539–1544; Zon, G. *Pharmaceutical Res.* 1988, 5, 539–549). Because of recent advances in synthesis of nuclease resistant oligonucleotides, which exhibit enhanced cell uptake, it is now possible to consider the use of antisense oligonucleotides as a novel form of therapeutics.

Antisense oligonucleotides offer an ideal solution to the problems encountered in prior art approaches. They can be designed to selectively inhibit a given isoenzyme, they inhibit the production of the enzyme, and they avoid non-specific mechanisms such as free radical scavenging or binding to multiple receptors. A complete understanding of enzyme mechanisms or receptor-ligand interactions is not needed to design specific inhibitors.

DESCRIPTION OF TARGETS

The acute infiltration of neutrophils into the site of inflammation appears to be due to increased expression of GMP-140, ELAM-1 and ICAM-1 on the surface of endothelial cells. The appearance of lymphocytes and monocytes during the later stages of an inflammatory reaction appear to be mediated by VCAM-1 and ICAM-1. ELAM-1 and GMP-140 are transiently expressed on vascular endothelial cells, while VCAM-1 and ICAM-1 are chronically expressed.

Human ICAM-1 is encoded by a 3.3-kb mRNA resulting in the synthesis of a 55,219 dalton protein (FIG. 1). ICAM-1 is heavily glycosylated through N-linked glycosylation sites. The mature protein has an apparent molecular mass of 90 kDa as determined by SDS-polyacrylamide gel electrophoresis. Staunton et al., *Cell* 1988, 52, 925–933. ICAM-1 is a member of the immunoglobulin supergene family, containing 5 immunoglobulin-like domains at the amino terminus, followed by a transmembrane domain and a cytoplasmic domain. The primary binding site for LFA-1 and rhinovirus are found in the first immunoglobulin-like domain. However, the binding sites appear to be distinct. Staunton et al., *Cell* 1990, 61, 243–354. Recent electron micrographic studies demonstrate that ICAM-1 is a bent rod 18.7 nm in length and 2 to 3 nm in diameter. Staunton et al., *Cell* 1990, 61, 243–254.

ICAM-1 exhibits a broad tissue and cell distribution, and may be found on white blood cells, endothelial cells, fibroblast, keratinocytes and other epithelial cells. The expression of ICAM-1 can be regulated on vascular endothelial cells, fibroblasts, keratinocytes, astrocytes and several cell lines by treatment with bacterial lipopolysaccharide and cytokines such as interleukin-1, tumor necrosis factor, gamma-interferon, and lymphotoxin. See, e.g., Frohman et al., *J. Neuroimmunol.* 1989, 23, 117–124. The molecular mechanism for increased expression of ICAM-1 following cytokine treatment has not been determined. ELAM-1 is a 115-kDa membrane glycoprotein (FIG. 2) which is a member of the selectin family of membrane glycoproteins. Bevilacqua et al., *Science* 1989, 243, 1160–1165. The amino terminal region of ELAM-1 contains sequences with homologies to members of lectin-like proteins, followed by a domain similar to epidermal growth factor, followed by six tandem 60-amino acid repeats similar to those found in complement receptors 1 and 2. These features are also shared by GMP-140 and MEL-14 antigen, a lymphocyte homing antigen. ELAM-1 is encoded for by a 3.9-kb mRNA. The 3'-untranslated region of ELAM-1 mRNA contains several sequence motifs ATTTA which are responsible for the rapid turnover of cellular mRNA consistent with the transient nature of ELAM-1 expression.

ELAM-1 exhibits a limited cellular distribution in that it has only been identified on vascular endothelial cells. Like ICAM-1, ELAM-1 is inducible by a number of cytokines including tumor necrosis factor, interleukin-1 and lymphotoxin and bacterial lipopolysaccharide. In contrast to ICAM-1, ELAM-1 is not induced by gamma-interferon. Bevilacqua et al., *Proc. Natl. Acad. Sci. USA* 1987, 84, 9238–9242; Wellicome et al., *J. Immunol.* 1990, 144, 2558–2565. The kinetics of ELAM-1 mRNA induction and disappearance in human umbilical vein endothelial cells precedes the appearance and disappearance of ELAM-1 on the cell surface. As with ICAM-1, the molecular mechanism for ELAM-1 induction is not known.

VCAM-1 is a 110-kDa membrane glycoprotein encoded by a 3.2-kb mRNA (FIG. 3). VCAM-1 appears to be encoded by a single-copy gene which can undergo alternative splicing to yield products with either six or seven immunoglobulin domains. Osborn et al., *Cell* 1989, 59, 1203–1211. The receptor for VCAM-1 is proposed to be CD29 (VLA-4) as demonstrated by the ability of monoclonal antibodies to CD29 to block adherence of Ramos cells to VCAM-1. VCAM-1 is expressed primarily on vascular endothelial cells. Like ICAM-1 and ELAM-1, expression of VCAM-1 on vascular endothelium is regulated by treatment with cytokines. Rice and Bevilacqua, *Science* 1989, 246, 1303–1306; Rice et al., *J. Exp. Med.* 1990, 171, 1369–1374. Increased expression appears to be due to induction of the mRNA.

For therapeutics, an animal suspected of having a disease which can be treated by decreasing the expression of ICAM-1, VCAM-1 and ELAM-1 is treated by administering oligonucleotides in accordance with this invention. Oligonucleotides may be formulated in a pharmaceutical composition, which may include carriers, thickeners, diluents, buffers, preservatives, surface active agents, liposomes or lipid formulations and the like, in addition to the oligonucleotide. Pharmaceutical compositions may also include one or more active ingredients such as antimicrobial agents, anti-inflammatory agents, anesthetics, and the like, in addition to oligonucleotide.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions, which may also contain buffers, liposomes, diluents and other suitable additives.
Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The present invention employs oligonucleotides for use in antisense inhibition of the function of RNA and DNA corresponding to proteins capable of modulating inflammatory cell adhesion. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions, which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl and halogen-substituted sugar moieties comprising one of the following at the 2' position: OH, SH, $SCH_3$, F, OCN, $O(CH_2)_n NH_2$ or $O(CH_2)_n CH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group.

The oligonucleotides in accordance with this invention preferably comprise from about 3 to about 50 nucleic acid base units. It is more preferred that such oligonucleotides comprise from about 8 to 25 nucleic acid base units, and still more preferred to have from about 12 to 22 nucleic acid base units. As will be appreciated, a nucleic acid base unit is a base-sugar combination suitably bound to an adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; however, the actual synthesis of the oligonucleotides are well within the talents of the routineer. It is also well known to use similar techniques to prepare other oligonucleotides such as the phosphorothioates and alkylated derivatives.

In accordance with this invention, persons of ordinary skill in the art will understand that messenger RNA identified by the open reading frames (ORFs) of the DNA from which they are transcribed includes not only the information from the ORFs of the DNA, but also associated ribonucleotides which form regions known to such persons as the 5'-untranslated region, the 3'-untranslated region, and intervening sequence ribonucleotides. Thus, oligonucleotides may be formulated in accordance with this invention, which are targeted wholly or in part to these associated ribonucleotides as well as to the informational ribonucleotides. In preferred embodiments, the oligonucleotide is specifically hybridizable with a transcription initiation site, a translation initiation site, an intervening sequence and sequences in the 3'-untranslated region.

In accordance with this invention, the oligonucleotide is specifically hybridizable with portions of nucleic acids encoding a protein involved in the adhesion of white blood cells either to other white blood cells or other cell types. In preferred embodiments, said proteins are intercellular adhesion molecule-1, vascular cell adhesion molecule-1 and endothelial leukocyte adhesion molecule-1. Oligonucleotides comprising the corresponding sequence, or part thereof, are useful in the invention. For example, FIG. 1 is a human intercellular adhesion molecule-1 mRNA sequence. A preferred sequence segment, which may be useful in whole or in part, is:

| 5' 3' | SEQ ID NO: |
|---|---|
| TGGGAGCCATAGCGAGGC | 1 |
| GAGGAGCTCAGCGTCGACTG | 2 |
| GACACTCAATAAATAGCTGGT | 3 |
| GAGGCTGAGGTGGGAGGA | 4 |
| CGATGGGCAGTGGGAAAG | 5 |
| GGGCGCGTGATCCTTATAGC | 6 |
| CATAGCGAGGCTGAGGTTGC | 7 |
| CGGGGGCTGCTGGGAGCCAT | 8 |
| TCAGGGAGGCGTGGCTTGTG | 13 |
| CCTGTCCCGGGATAGGTTCA | 14 |
| TTGAGAAAGCTTTATTAACT | 16 |
| CCCCCACCACTTCCCCTCTC. | 15 |

FIG. 2 is a human endothelial leukocyte adhesion molecule-1 mRNA sequence. A preferred sequence segment, which may be useful in whole or in part, is:

| 5' 3' | SEQ ID NO: |
|---|---|
| CAATCATGACTTCAAGAGTTCT | 28 |
| TCACTGCTGCCTCTGTCTCAGG | 73 |
| TGATTCTTTTGAACTTAAAAGGA | 74 |
| TTAAAGGATGTAAGAAGGCT | 75 |
| CATAAGCACATTTATTGTC | 76 |
| TTTTGGGAAGCAGTTGTTCA | 77 |
| AACTGTGAAGCAATCATGACT | 78 |
| CCTTGAGTGGTGCATTCAACCT | 79 |
| AATGCTTGCTCACACAGGCATT | 80. |

FIG. 3 is a human vascular cell adhesion molecule-1 mRNA sequence. A preferred sequence segment, which may be useful in whole or in part, is:

| 5' 3' | SEQ ID NO: |
|---|---|
| CCAGGCATTTTAAGTTGCTGT | 40 |
| CCTGAAGCCAGTGAGGCCCG | 41 |
| GATGAGAAAATAGTGGAACCA | 42 |
| CTGAGCAAGATATCTAGAT | 43 |
| CTACACTTTTGATTTCTGT | 44 |
| TTGAACATATCAAGCATTAGCT | 45 |
| TTTACATATGTACAAATTATGT | 46 |
| AATTATCACTTTACTATACAAA | 47 |
| AGGGCTGACCAAGACGGTTGT | 48. |

While the illustrated sequences are believed to be accurate, the present invention is directed to the correct sequences, should errors be found. Oligonucleotides useful in the invention comprise one of these sequences, or part thereof. Thus, it is preferred to employ any of these oligonucleotides as set forth above or any of the similar oligonucleotides which persons of ordinary skill in the art can prepare from knowledge of the preferred antisense targets for the modulation of the synthesis of inflammatory cell adhesion molecules.

Several preferred embodiments of this invention are exemplified in accordance with the following nonlimiting examples. The target mRNA species for modulation relates to intercellular adhesion molecule-1, endothelial leukocyte adhesion molecule-1, and vascular cell adhesion molecule-1. Persons of ordinary skill in the art will appreciate that the present invention is not so limited, however, and that it is generally applicable. The inhibition or modulation of production of the ICAM-1 and/or ELAM-1 and/or VCAM-1 are expected to have significant therapeutic benefits in the treatment of disease. In order to assess the effectiveness of the compositions, an assay or series of assays is performed.

One type of disorder suitable for treatment with the oligonucleotides of the present invention are in inflammatory ophthalmic disorders including redness and inflammation caused by allergens and allergic reactions. The oligonucleotides can also be used as an adjuvant to antibiotic treatment of conjunctivitis. In a preferred embodiment, the oligonucleotides are used to preserve corneal explants ex vivo and to prevent corneal allograft rejection. These oligonucleotides may be placed in solution and administered as eyedrops for topical treatment of the allograft. The solution is suitable for use as a storage medium for corneal explants, and is administered in eye drop form following corneal transplant to prevent corneal allograft rejection.

The following examples are provided for illustrative purposes only and are not intended to limit the invention.

EXAMPLES

Example 1

Expression of ICAM-1, VCAM-1 and ELAM-1 on the surface of cells can be quantitated using specific monoclonal antibodies in an ELISA. Cells are grown to confluence in 96 well microtiter plates. The cells are stimulated with either interleukin-1 or tumor necrosis factor for 4 to 8 hours to quantitate ELAM-1 and 8 to 24 hours to quantitate ICAM-1 and VCAM-1. Following the appropriate incubation time with the cytokine, the cells are gently washed three times with a buffered isotonic solution containing calcium and magnesium such as Dulbecco's phosphate buffered saline (D-PBS). The cells are then directly fixed on the microtiter plate with 1 to 2% paraformaldehyde diluted in D-PBS for 20 minutes at 25° C. The cells are washed again with D-PBS three times. Nonspecific binding sites on the microtiter plate are blocked with 2% bovine serum albumin in D-PBS for 1 hour at 37° C. Cells are incubated with the appropriate monoclonal antibody diluted in blocking solution for 1 hour at 37° C. Unbound antibody is removed by washing the cells three times with D-PBS. Antibody bound to the cells is detected by incubation with a 1:1000 dilution of biotinylated goat anti-mouse IgG (Bethesda Research Laboratories, Gaithersburg, Md.) in blocking solution for 1 hour at 37° C. Cells are washed three times with D-PBS and then incubated with a 1:1000 dilution of streptavidin conjugated to β-galactosidase (Bethesda Research Laboratories) for 1 hour at 37° C. The cells are washed three times with D-PBS for 5 minutes each. The amount of β-galactosidase bound to the specific monoclonal antibody is determined by developing the plate in a solution of 3.3 mM chlorophenolred-β-D-galactopyranoside, 50 mM sodium phosphate, 1.5 mM $MgCl_2$; pH=7.2 for 2 to 15 minutes at 37° C. The concentration of the product is determined by measuring the absorbance at 575 nm in an ELISA microtiter plate reader.

An example of the induction of ICAM-1 observed following stimulation with either interleukin-1β or tumor necrosis factor α in several human cell lines is shown in FIG. 4. Cells were stimulated with increasing concentrations of interleukin-1 or tumor necrosis factor for 15 hours and processed as described above. ICAM-1 expression was determined by incubation with a 1:1000 dilution of the monoclonal antibody 84H10 (Amac Inc., Westbrook, Me.). The cell lines used were passage 4 human umbilical vein endothelial cells (HUVEC), a human epidermal carcinoma cell line (A431), a human melanoma cell line (SK-MEL -2) and a human lung carcinoma cell line (A549). ICAM-1 was induced on all the cell lines, however, tumor necrosis factor was more effective than interleukin-1 in induction of ICAM-1 expression on the cell surface (FIG. 4).

Figure 5:
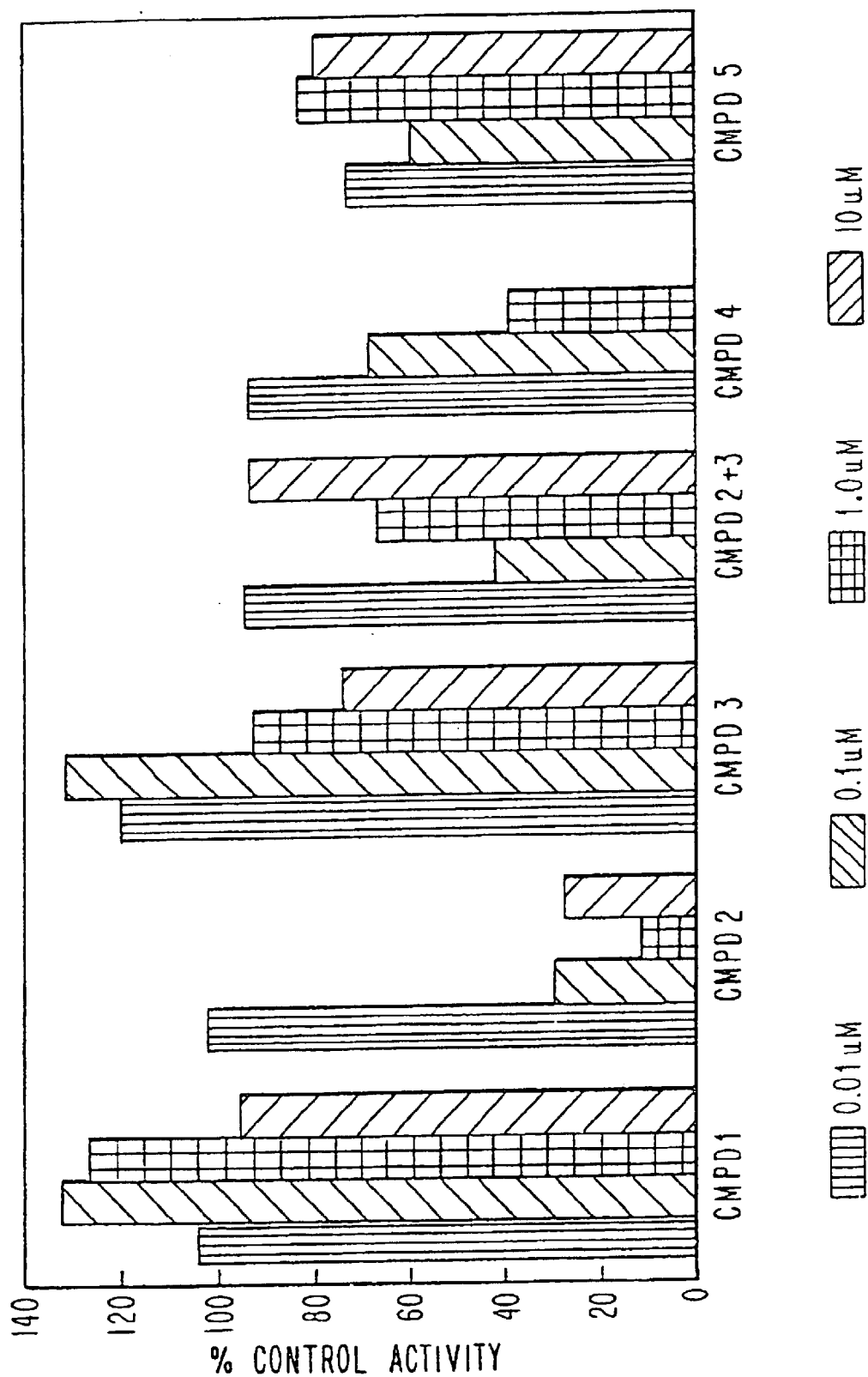
FIG. 5 is a graphical representation of the effects of selected antisense oligonucleotides on ICAM-1 expression on human umbilical vein endothelial cells.

Screening antisense oligonucleotides for inhibition of ICAM-1, VCAM-1 or ELAM-1 expression is performed as described above with the exception of pretreatment of cells with the oligonucleotides prior to challenge with the cytokines. An example of antisense oligonucleotide inhibition of ICAM-1 expression is shown in FIG. 5. Human umbilical vein endothelial cells (HUVEC) were treated with increasing concentration of oligonucleotide diluted in Opti MEM (GIBCO, Grand Island, N.Y.) containing 8 μM N-[1-(2,3-dioleyloxy) propyl]-N,N,N-trimethylammonium chloride (DOTMA) for 4 hours at 37° C. to enhance uptake of the oligonucleotides. The medium was removed and replaced with endothelial growth medium (EGM-UV; Clonetics, San Diego, Calif.) containing the indicated concentration of oligonucleotide for an additional 4 hours. Interleukin-1β was added to the cells at a concentration of 5 units/ml and incubated for 14 hours at 37° C. The cells were quantitated for ICAM-1 expression using a 1:1000 dilution of the monoclonal antibody 84H10 as described above. The oligonucleotides used were:

COMPOUND 1—(ISIS 1558) a phosphodiester oligonucleotide designed to hybridize with position 64–80 of the mRNA covering the AUG initiation of translation codon having the sequence 5'-TGGGAGCCATAGCGAGGC-3' (SEQ ID NO: 1).

COMPOUND 2—(ISIS 1570) a phosphorothioate containing oligonucleotide corresponding to the same sequence as COMPOUND 1.

COMPOUND 3—a phosphorothioate oligonucleotide complementary to COMPOUND 1 and COMPOUND 2 exhibiting the sequence 5'-GCCTCGCTATGGCTCCCA-3' (SEQ ID NO: 81).

COMPOUND 4"(ISIS 1572) a phosphorothioate containing oligonucleotide designed to hybridize to positions 2190–2210 of the mRNA in the 3' untranslated region containing the sequence 5'-GACACTCAATAAATAGCTGGT-3' (SEQ ID NO: 3).

COMPOUND 5—(ISIS 1821) a phosphorothioate containing oligonucleotide designed to hybridize to human 5-lipoxygenase mRNA used as a control containing the sequence 5'-CATGGCGCGGGCCGCGGG-3' (SEQ ID NO: 82).

The phosphodiester oligonucleotide targeting the AUG initiation of translation region of the human ICAM-1 mRNA (COMPOUND 1) did not inhibit expression of ICAM-1; however, the corresponding phosphorothioate containing oligonucleotide (COMPOUND 2) inhibited ICAM-1 expression by 70% at a concentration of 0.1 μM and 90% at 1 μM concentration (FIG. 4). The increased potency of the phosphorothioate oligonucleotide over the phosphodiester is probably due to increased stability. The sense strand to COMPOUND 2, COMPOUND 3, modestly inhibited ICAM-1 expression at 10 μM. If COMPOUND 2 was prehybridized to COMPOUND 3 prior to addition to the cells, the effects of COMPOUND 2 on ICAM-1 expression were attenuated suggesting that the activity of COMPOUND 2 was due to antisense oligonucleotide effect, requiring hybridization to the mRNA. The antisense oligonucleotide directed against 3' untranslated sequences (COMPOUND 4) inhibited ICAM-1 expression 62% at a concentration of 1 μM (FIG. 5). The control oligonucleotide, targeting human 5-lipoxygenase (COMPOUND 5) reduced ICAM-1 expression by 20%. These data demonstrate that oligonucleotides are capable of inhibiting ICAM-1 expression on human umbilical vein endothelial cells and suggest that the inhibition of ICAM-1 expression is due to an antisense activity.

Figure 6A:
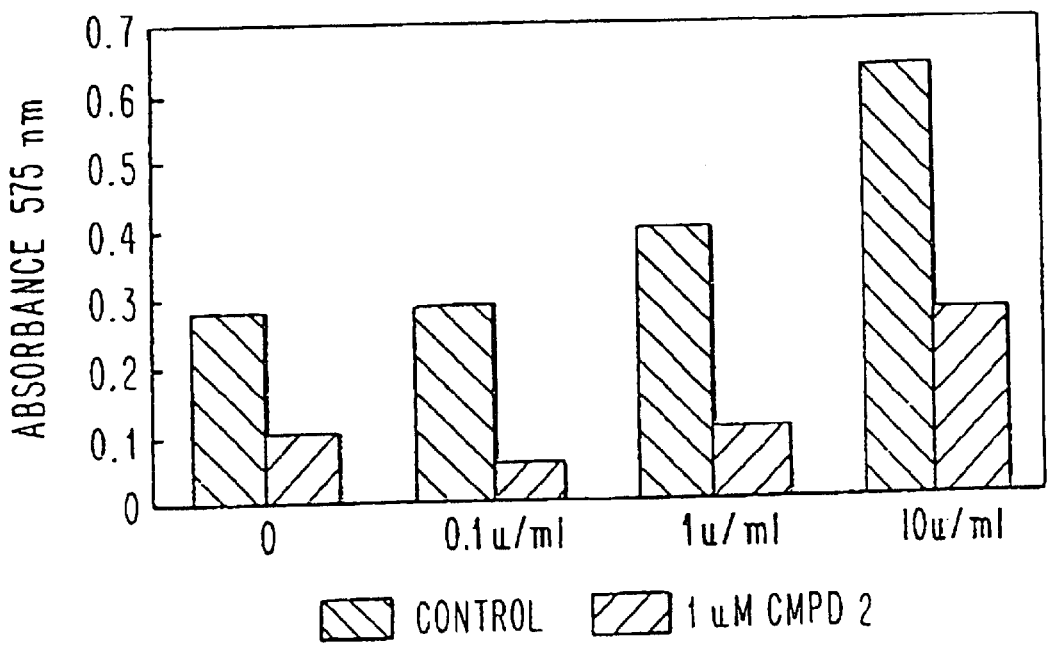
FIGS. 6A and 6B are a graphical representation of the effects of an antisense oligonucleotide on the expression of ICAM-1 in human umbilical vein endothelial cells stimulated with tumor necrosis factor and interleukin-1.
Figure 6B:
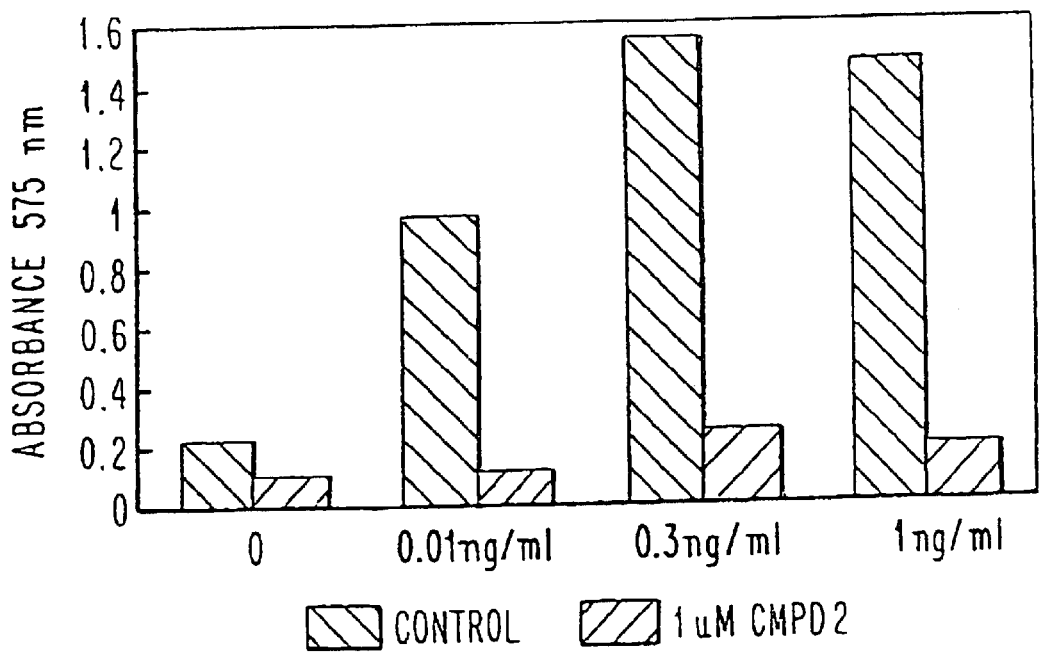

The antisense oligonucleotide COMPOUND 2 at a concentration of 1 μM inhibits expression of ICAM-1 on human umbilical vein endothelial cells stimulated with increasing concentrations of tumor necrosis factor and interleukin-1 (FIG. 6). These data demonstrate that the effects of COMPOUND 2 are not specific for interleukin-1 stimulation of cells.

Analogous assays can also be used to demonstrate inhibition of ELAM-1 and VCAM-1 expression by antisense oligonucleotides.

Example 2

A second cellular assay which can be used to demonstrate the effects of antisense oligonucleotides on ICAM-1, VCAM-1 or ELAM-1 expression is a cell adherence assay. Target cells are grown as a monolayer in a multiwell plate, treated with oligonucleotide followed by cytokine. The adhering cells are then added to the monolayer cells and incubated for 30 to 60 minutes at 37° C. and washed to remove nonadhering cells. Cells adhering to the monolayer may be determined either by directly counting the adhering cells or prelabeling the cells with a radioisotope such as $^{51}Cr$ and quantitating the radioactivity associated with the monolayer as described. Dustin and Springer, *J. Cell Biol.* 1988, 107, 321–331. Antisense oligonucleotides may target either ICAM-1, VCAM-1 or ELAM-1 in the assay.

Figure 7:
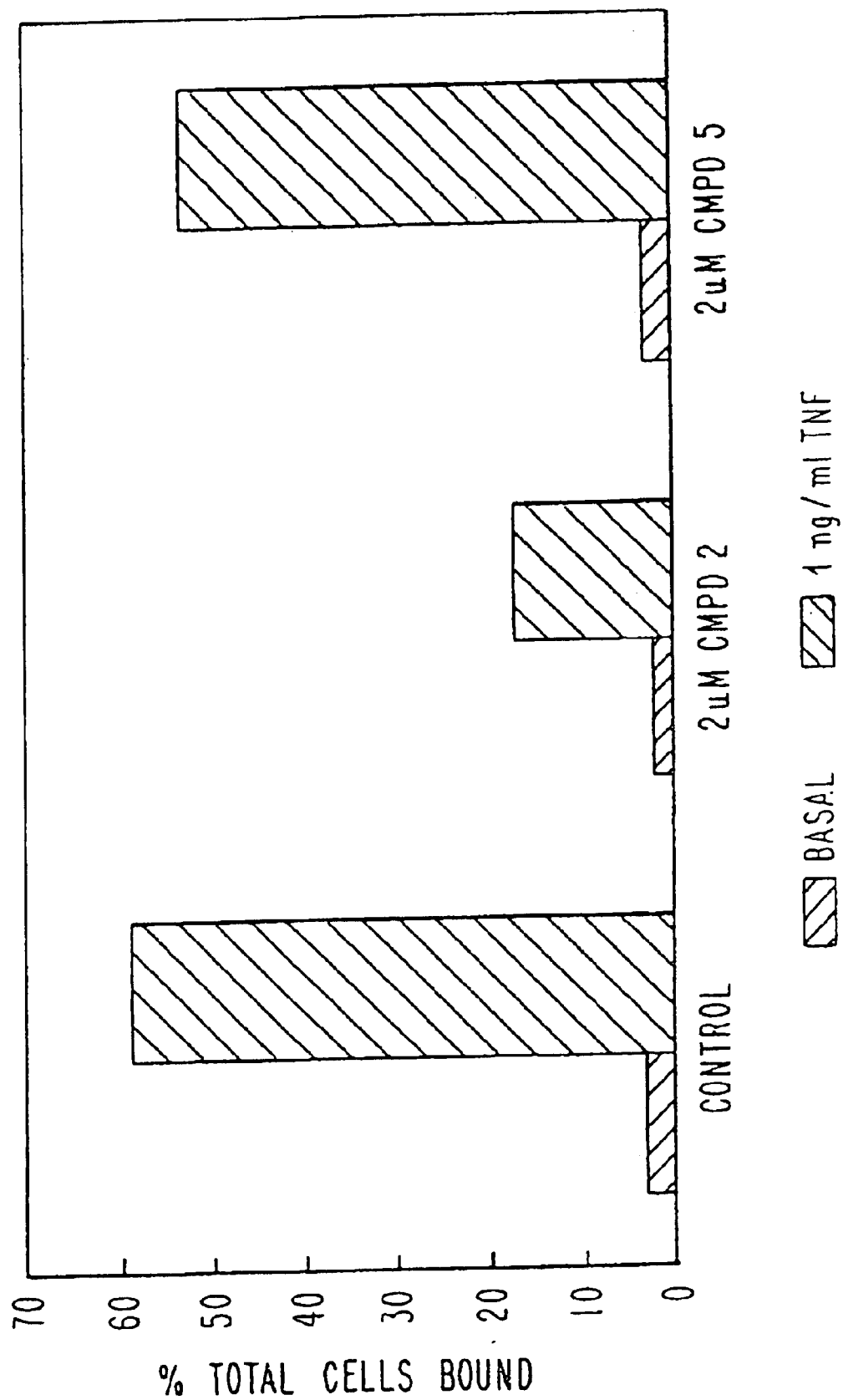
FIG. 7 is a graphical representation of the effect of antisense oligonucleotides on ICAM-1 mediated adhesion of DMSO differentiated HL-60 cells to control and tumor necrosis factor treated human umbilical vein endothelial cells.

An example of the effects of antisense oligonucleotides targeting ICAM-1 mRNA on the adherence of DMSO differentiated HL-60 cells to tumor necrosis factor treated human umbilical vein endothelial cells is shown in FIG. 7. Human umbilical vein endothelial cells were grown to 80% confluence in 12 well plates. The cells were treated with 2 μM oligonucleotide diluted in Opti-MEM containing 8 μM DOTMA for 4 hours at 37° C. The medium was removed and replaced with fresh endothelial cell growth medium (EGM-UV) containing 2 μM of the indicated oligonucleotide and incubated 4 hours at 37° C. Tumor necrosis factor, 1 ng/ml, was added to cells as indicated and cells incubated for an additional 19 hours. The cells were washed once with EGM-UV and $1.6 \times 10^6$ HL-60 cells differentiated for 4 days with 1.3% DMSO added. The cells were allowed to attach for 1 hour at 37° C. and gently washed 4 times with Dulbecco's phosphate-buffered saline (D-PBS) warmed to 37° C. Adherent cells were detached from the monolayer by addition of 0.25 ml of cold (4EC) phosphate-buffered saline containing 5 mM EDTA and incubated on ice for 5 minutes.

The number of cells removed by treatment with EDTA was determined by counting with a hemocytometer. Endothelial cells detached from the monolayer by EDTA treatment could easily be distinguished from HL-60 cells by morphological differences. In the absence of tumor necrosis factor, 3% of the HL-60 cells bound to the endothelial cells. Treatment of the endothelial cell monolayer with 1 ng/ml tumor necrosis factor increased the number of adhering cells to 59% of total cells added (FIG. 7). Treatment with the antisense oligonucleotide COMPOUND 2 or the control oligonucleotide COMPOUND 5 did not change the number of cells adhering to the monolayer in the absence of tumor necrosis factor treatment (FIG. 7). The antisense oligonucleotide, COMPOUND 2 reduced the number of adhering cells from 59% of total cells added to 17% of the total cells added (FIG. 7). In contrast, the control oligonucleotide COMPOUND 5 did not significantly reduce the number of cells adhering to the tumor necrosis factor treated endothelial monolayer, i.e., 53% of total cells added for COMPOUND 5 treated cells versus 59% for control cells.

These data indicate that antisense oligonucleotides are capable of inhibiting ICAM-1 expression on endothelial cells and that inhibition of ICAM-1 expression correlates with a decrease in the adherence of a neutrophil-like cell to the endothelial monolayer in a sequence specific fashion. Because other molecules also mediate adherence of white blood cells to endothelial cells, such as ELAM-1, and VCAM-1 it is not expected that adherence would be completely blocked.

Example 3
Synthesis and Characterization of Oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide.

2'-fluoro phosphorothioate oligonucleotides were synthesized using 5'-dimethoxytrityl-3'-phosphoramidites and prepared as disclosed in U.S. patent application Serial Nos. 463,358, filed Jan. 11, 1990, and 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems) and deblocking in concentrated ammonium hydroxide at 55EC for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and phosphorothioate oligonucleotides were judged from electrophoresis to be greater than 80% full length material.

RNA oligonucleotide synthesis was performed on an ABI model 380B DNA synthesizer. The standard synthesis cycle was modified by increasing the wait step after the pulse delivery of tetrazole to 900 seconds. The bases were deprotected by incubation in methanolic ammonia overnight. Following base deprotections the oligonucleotides were dried in vacuo. The t-butyldimethylsilyl protecting the 2' hydroxyl was removed by incubating the oligonucleotide in 1 M tetrabutylammonium-fluoride in tetrahydrofuran overnight. The RNA oligonucleotides were further purified on $C_{18}$ Sep-Pak cartridges (Waters, Division of Millipore Corp., Milford Mass.) and ethanol precipitated.

The relative amounts of phosphorothioate and phosphodiester linkages obtained by this synthesis were periodically checked by $^{31}p$ NMR spectroscopy. The spectra were obtained at ambient temperature using deuterium oxide or dimethyl sulfoxide-$d_6$ as solvent. Phosphorothioate samples typically contained less than one percent of phosphodiester linkages.

Secondary evaluation was performed with oligonucleotides purified by trityl-on HPLC on a PRP-1 column (Hamilton Co., Reno, Nev.) using a gradient of acetonitrile in 50 mM triethylammonium acetate, pH 7.0 (4% to 32% in 30 minutes, flow rate=1.5 ml/min). Appropriate fractions were pooled, evaporated and treated with 5% acetic acid at ambient temperature for 15 minutes. The solution was extracted with an equal volume of ethyl acetate, neutralized with ammonium hydroxide, frozen and lyophilized. HPLC-purified oligonucleotides were not significantly different in potency from precipitated oligonucleotides, as judged by the ELISA assay for ICAM-1 expression.

Example 4
Cell Culture and Treatment with Oligonucleotides

The human lung carcinoma cell line A549 was obtained from the American Type Culture Collection (Bethesda Md.). Cells were grown in Dulbecco's Modified Eagle's Medium (Irvine Scientific, Irvine Calif.) containing 1 gm glucose/liter and 10% fetal calf serum (Irvine Scientific). Human umbilical vein endothelial cells (HUVEC) (Clonetics, San Diego Calif.) were cultured in EGM-UV medium (Clonetics). HUVEC were used between the second and sixth passages. Human epidermal carcinoma A431 cells were obtained from the American Type Culture Collection and cultured in DMEM with 4.5 g/l glucose. Primary human keratinocytes were obtained from Clonetics and grown in KGM (Keratinocyte growth medium, Clonetics).

Cells grown in 96-well plates were washed three times with Opti-MEM (GIBCO, Grand Island, N.Y.) prewarmed to 37° C. 100 μl of Opti-MEM containing either 10 μg/ml N-[1-(2,3-dioleyloxy)propyl]-N,N,N-trimethylammonium chloride (DOTMA, Bethesda Research Labs, Bethesda Md.) in the case of HUVEC cells or 20 μg/ml DOTMA in the case of A549 cells was added to each well. Oligonucleotides were sterilized by centrifugation through 0.2 μm Centrex cellulose acetate filters (Schleicher and Schuell, Keene, N.H.). oligonucleotides were added as 20× stock solution to the wells and incubated for 4 hours at 37° C. Medium was removed and replaced with 150 μl of the appropriate growth medium containing the indicated concentration of oligonucleotide. Cells were incubated for an additional 3 to 4 hours at 37° C. then stimulated with the appropriate cytokine for 14 to 16 hours, as indicated. ICAM-1 expression was determined as described in Example 1. The presence of DOTMA during the first 4 hours incubation with oligonucleotide increased the potency of the oligonucleotides at least 100-fold. This increase in potency correlated with an increase in cell uptake of the oligonucleotide.

Example 5
ELISA Screening of Additional Antisense Oligonucleotides for Activity Against ICAM-1 Gene Expression in Interleukin-1β-Stimulated Cells Antisense oligonucleotides were originally designed that would hybridize to five target sites on the human ICAM-1 mRNA. Oligonucleotides were synthesized in both phosphodiester (P=O; ISIS 1558, 1559, 1563, 1564 and 1565) and phosphorothioate (P=S; ISIS 1570, 1571, 1572, 1573, and 1574) forms. The oligonucleotides are shown in Table 1.

TABLE 1

ANTISENSE OLIGONUCLEOTIDES WHICH TARGET HUMAN ICAM-1

| ISIS NO. | SEQ ID NO. | TARGET REGION | MODIFICATION |
|---|---|---|---|
| 1558 | 1 | AUG Codon (64–81) | P = O |
| 1559 | 2 | 5'-Untranslated (32–49) | P = O |
| 1563 | 3 | 3'-Untranslated (2190–3010) | P = O |
| 1564 | 4 | 3'-Untranslated (2849–2866) | P = O |
| 1565 | 5 | Coding Region (1378–1395) | P = O |
| 1570 | 1 | AUG Codon (64–81) | P = S |
| 1571 | 2 | 5'-Untranslated (32–49) | P = S |
| 1572 | 3 | 3'-Untranslated (2190–3010) | P = S |
| 1573 | 4 | 3'-Untranslated (2849–2866) | P = S |
| 1574 | 5 | Coding Region (1378–1395) | P = S |
| 1930 | 6 | 5'-Untranslated (1–20) | P = S |
| 1931 | 7 | AUG Codon (55–74) | P = S |
| 1932 | 8 | AUG Codon (72–91) | P = S |
| 1933 | 9 | Coding Region (111–130) | P = S |
| 1934 | 10 | Coding Region (351–370) | P = S |
| 1935 | 11 | Coding Region (889–908) | P = S |
| 1936 | 12 | Coding Region (1459–1468) | P = S |
| 1937 | 13 | Termination Codon (1651–1687) | P = S |
| 1938 | 14 | Termination Codon (1668–1687) | P = 5 |
| 1939 | 15 | 3'-Untranslated (1952–1971) | P = S |
| 1940 | 16 | 3'-Untranslated (2975–2994) | P = S |
| 2149 | 17 | AUG Codon (64–77) | P = S |
| 2163 | 18 | AUG Codon (64–75) | P = S |
| 2164 | 19 | AUG Codon (64–73) | P = S |
| 2165 | 20 | AUG Codon (66–80) | P = S |
| 2173 | 21 | AUG Codon (64–79) | P = S |
| 2302 | 22 | 3'-Untranslated (2114–2133) | P = S |
| 2303 | 23 | 3'-Untranslated (2039–2058) | P = S |
| 2304 | 24 | 3'-Untranslated (1895–1914) | P = S |
| 2305 | 25 | 3'-Untranslated (1935–1954) | P = S |
| 2307 | 26 | 3'-Untranslated (1976–1995) | P = S |
| 2634 | 1 | AUG-Codon (64–81) | 2'-fluoro A, C & U; P = S |
| 2637 | 15 | 3'-Untrans. (1952–1971) | 2'-fluoro A, C & U; |
| 2691 | 1 | AUG Codon (64–81) | P = O, except last 3 bases, P = S |
| 2710 | 15 | 3'-Untrans. (1952–1971) | 2'-O—methyl; P = O |
| 2711 | 1 | AUG Codon (64–81) | 2'-O—methyl; P = O |
| 2973 | 15 | 3'-Untrans. (1952–1971) | 2'-O—methyl; P = S |
| 2974 | 1 | AUG Codon (64–81) | 2'-O—methyl; P = S |
| 3064 | 27 | 5'-CAP (32–51) | P = S; G & C added as spacer to 3' |
| 3067 | 84 | 5'-CAP (32–51) | P = S |
| 3222 | 84 | 5'-CAP (32–51) | 2'-O—methyl; P = O |
| 3224 | 84 | 5'-CAP (32–51) | 2'-O—methyl; P = S |
| 3581 | 85 | 3'-Untranslated (1959–1978) | P = S |

Inhibition of ICAM-1 expression on the surface of interleukin-1β-stimulated cells by the oligonucleotides was determined by ELISA assay as described in Example 1. The oligonucleotides were tested in two different cell lines. None of the phosphodiester oligonucleotides inhibited ICAM-1 expression. This is probably due to the rapid degradation of phosphodiester oligonucleotides in cells. Of the five phosphorothioate oligonucleotides, the most active was ISIS 1570, which hybridizes to the AUG translation initiation codon. A 2'-o-methyl phosphorothioate oligonucleotide, ISIS 2974, was approximately threefold less effective than ISIS 1570 in inhibiting ICAM-1 expression in HUVEC and A549 cells. A 2'-fluoro oligonucleotide, ISIS 2634, was also less effective.

Figure 8:
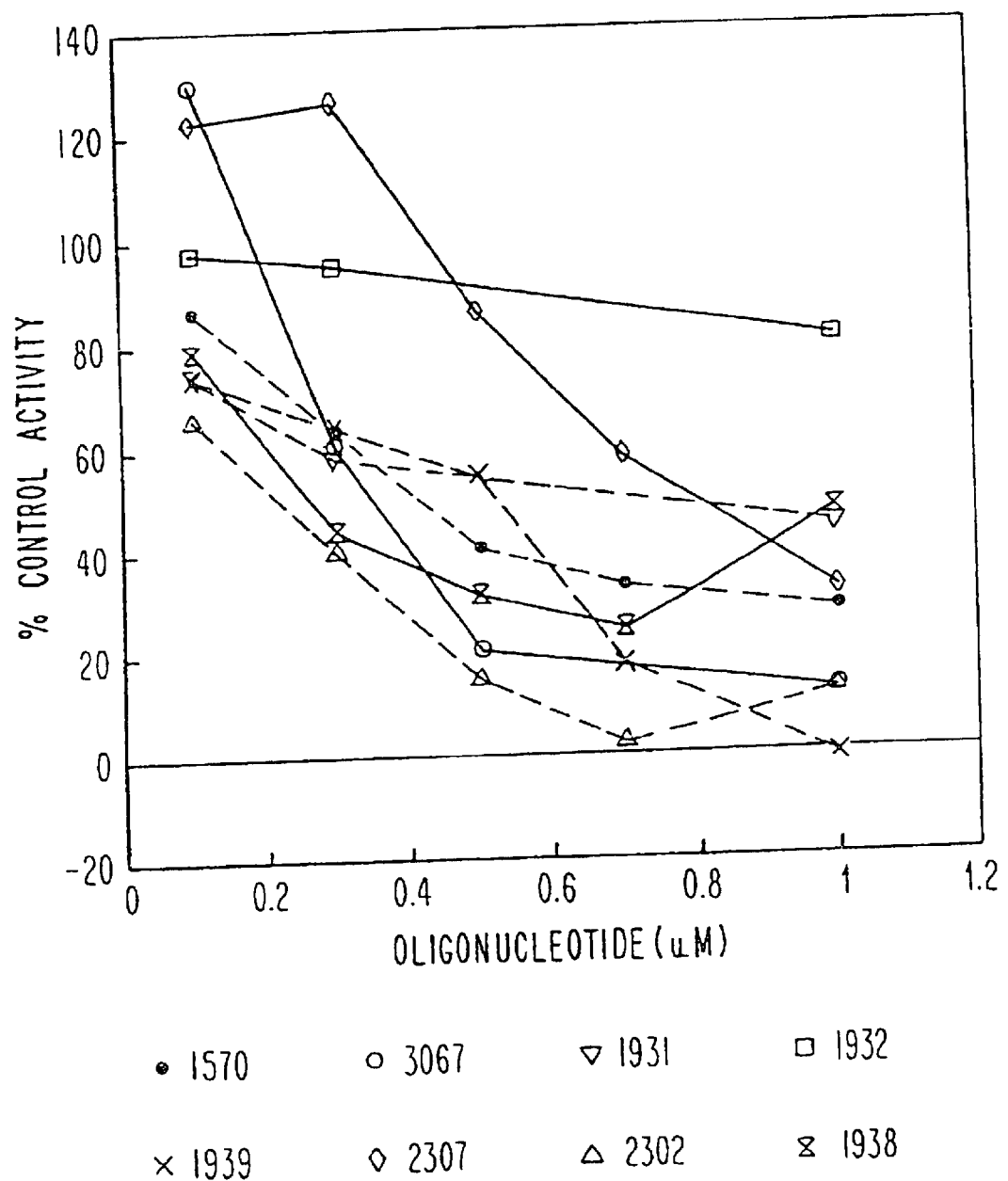
FIG. 8 is a graphical representation of the effects of selected antisense oligonucleotides on ICAM-1 expression in A549 human lung carcinoma cells.

Based on the initial data obtained with the five original targets, additional oligonucleotides were designed which would hybridize with the ICAM-1 mRNA. The antisense oligonucleotide (ISIS 3067) which hybridizes to the predicted transcription initiation site (5' cap site) was approximately as active in IL-1β-stimulated cells as the oligonucleotide that hybridizes to the AUG codon (ISIS 1570), as shown in FIG. 8. ISIS 1931 and 1932 hybridize 5'and 3', respectively, to the AUG translation initiation codon. All three oligonucleotides that hybridize to the AUG region inhibit ICAM-1 expression, though ISIS 1932 was slightly less active than ISIS 1570 and ISIS 1931. Oligonucleotides which hybridize to the coding region of ICAM-1 mRNA (ISIS 1933, 1934, 1935, 1574 and 1936) exhibited weak activity. Oligonucleotides that hybridize to the translation termination codon (ISIS 1937 and 1938) exhibited moderate activity.

Surprisingly, the most active antisense oligonucleotide was ISIS 1939, a phosphorothioate oligonucleotide targeted to a sequence in the 3'-untranslated region of ICAM-1 mRNA (see Table 1). Other oligonucleotides having the same sequence were tested, 2'-O-methyl (ISIS 2973) and 2'-fluoro (ISIS 2637); however, they did not exhibit this level of activity. Oligonucleotides targeted to other 3' untranslated sequences (ISIS 1572, 1573 and 1940) were also not as active as ISIS-1939. In fact, ISIS 1940, targeted to the polyadenylation signal, did not inhibit ICAM-1 expression.

Because ISIS 1939 proved unexpectedly to exhibit the greatest antisense activity of the original 16 oligonucleotides tested, other oligonucleotides were designed to hybridize to sequences in the 3'-untranslated region of ICAM-1 mRNA (ISIS 2302, 2303, 2304, 2305, and 2307, as shown in Table 1). ISIS 2307, which hybridizes to a site only five bases 3' to the ISIS 1939 target, was the least active of the series (FIG. 8). ISIS 2302, which hybridizes to the ICAM-1 mRNA at a position 143 bases 3' to the ISIS 1939 target, was the most active of the series, with activity comparable to that of ISIS 1939. Examination of the predicted RNA secondary structure of the human ICAM-1 mRNA 3'-untranslated region (according to M. Zuker, Science 1989, 244, 48–52) revealed that both ISIS 1939 and ISIS 2302 hybridize to sequences predicted to be in a stable stem-loop structure. Current dogma suggests that regions of RNA secondary structure should be avoided when designing antisense oligonucleotides. Thus, ISIS 1939 and ISIS 2302 would not have been predicted to inhibit ICAM-1 expression.

The control oligonucleotide ISIS 1821 did inhibit ICAM-1 expression in HUVEC cells with activity comparable to that of ISIS 1934; however, in A549 cells ISIS 1821 was less effective than ISIS 1934. The negative control, ISIS 1821, was found to have a small amount of activity against ICAM expression, probably due in part to its ability to hybridize (12 of 13 base match) to the ICAM-1 mRNA at a position 15 bases 3' to the AUG translation initiation codon.

These studies indicate that the AUG translation initiation codon and specific 3'-untranslated sequences in the ICAM-1 mRNA were the most susceptible to antisense oligonucleotide inhibition of ICAM-1 expression.

Figure 9:
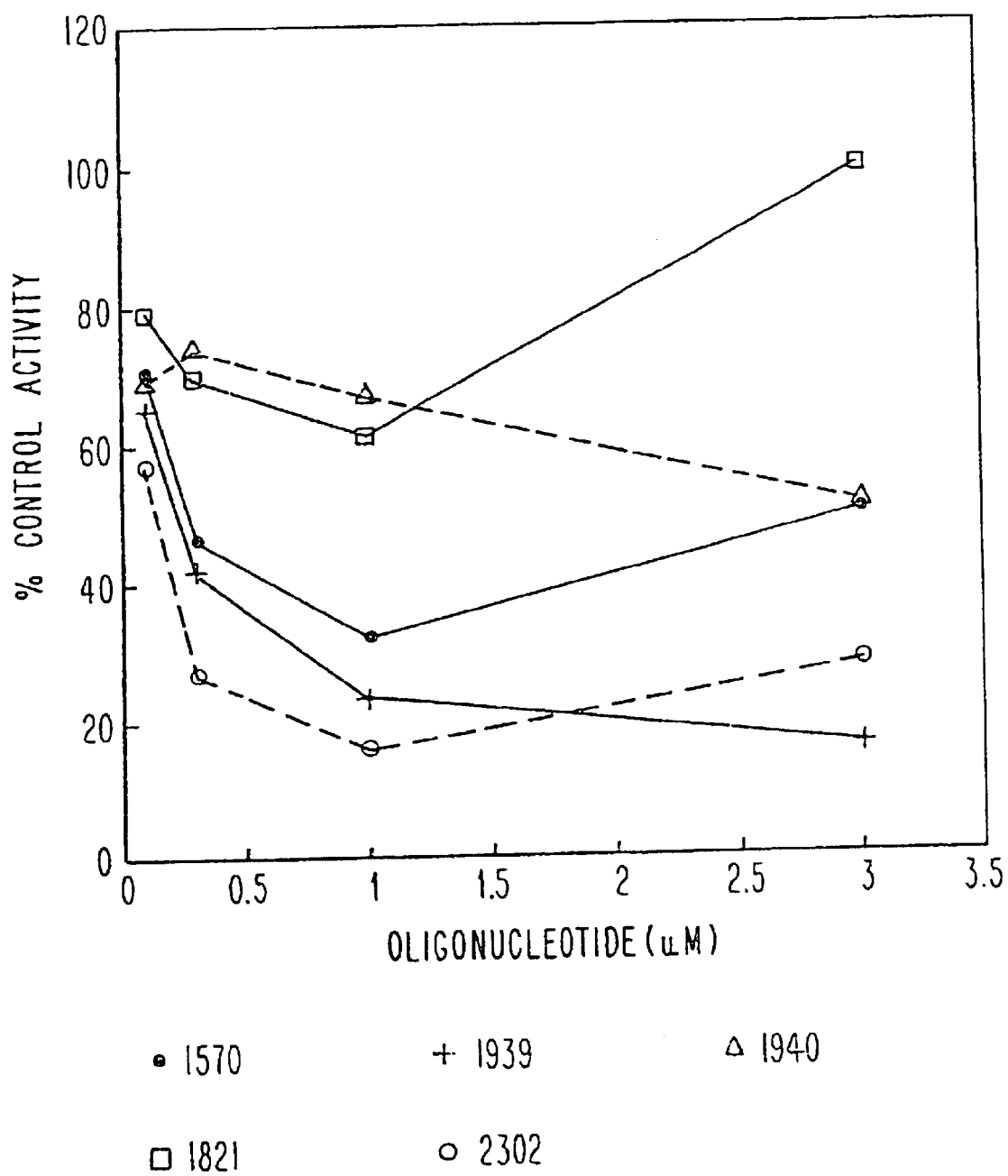
FIG. 9 is a graphical representation of the effects of selected antisense oligonucleotides on ICAM-1 expression in primary human keratinocytes.

In addition to inhibiting ICAM-1 expression in human umbilical vein cells and the human lung carcinoma cells (A549), ISIS 1570, ISIS 1939 and ISIS 2302 were shown to inhibit ICAM-1 expression in the human epidermal carcinoma A431 cells and in primary human keratinocytes (shown in FIG. 9). These data demonstrate that antisense oligonucleotides are capable of inhibiting ICAM-1 expression in several human cell lines. Furthermore, the rank order potency of the oligonucleotides is the same in the four cell lines examined. The fact that ICAM-1 expression could be inhibited in primary human keratinocytes is important because epidermal keratinocytes are an intended target of the antisense nucleotides.

Example 6
Antisense Oligonucleotide Inhibition of ICAM-1 Expression in Cells Stimulated with Other Cytokines Two oligonucleotides, ISIS 1570 and ISIS 1939, were tested for their ability to inhibit TNF-α and IFN-α-induced ICAM-1 expression. Treatment of A549 cells with 1 μM antisense oligonucleotide inhibited IL-1β, TNF-α and IFN-α-induced ICAM-1 expression in a sequence-specific manner. The antisense oligonucleotides inhibited IL-1β and TNF-α-induced ICAM-1 expression to a similar extent, while IFN-α-induced ICAM-1 expression was more sensitive to antisense inhibition. The control oligonucleotide, ISIS 1821, did not significantly inhibit IL-1β- or TNF-α-induced ICAM-1 expression and inhibited IFN-α-induced ICAM-1 expression slightly, as follows:
Antisense Oligonucleotide
(% Control Expression)

| Cytokine | ISIS 1570 | ISIS 1939 | ISIS 1821 |
|---|---|---|---|
| 3 U/ml IL-1â | 56.6 " 2.9 | 38.1 " 3.2 | 95 " 6.6 |
| 1 ng/ml TNF-á | 58.1 " 0.9 | 37.6 " 4.1 | 103.5 " 8.2 |
| 100 U/ml gamma-IFN | 38.9 " 3.0 | 18.3 " 7.0 | 83.0 " 3.5 |

Example 7
Antisense Effects are Abolished by Sense Strand Controls

The antisense oligonucleotide inhibition of ICAM-1 expression by the oligonucleotides ISIS 1570 and ISIS 1939 could be reversed by hybridization of the oligonucleotides with their respective sense strands. The phosphorothioate sense strand for ISIS 1570 (ISIS 1575), when applied alone, slightly enhanced IL-1β-induced ICAM-1 expression. Premixing ISIS 1570 with ISIS 1575 at equal molar concentrations, prior to addition to the cells, blocked the effects of ISIS 1570. The complement to ISIS 1939 (ISIS 2115) enhanced ICAM-1 expression by 46% when added to the cells alone. Prehybridization of ISIS 2115 to ISIS 1939 completely blocked the inhibition of ICAM-1 expression by ISIS 1939.

Example 8
Measurement of Oligonucleotide Tm (Dissociation Temperature of Oligonucleotide from Target)

To determine if the potency of the inhibition of ICAM-1 expression by antisense oligonucleotides was due to their affinity for their target sites, thermodynamic measurements were made for each of the oligonucleotides. The antisense oligonucleotides (synthesized as phosphorothioates) were hybridized to their complementary DNA sequences (synthesized as phosphodiesters). Absorbance vs. temperature profiles were measured at 4 μM each strand oligonucleotide in 100 mM Na+, 10 mM phosphate, 0.1 mM EDTA, pH 7.0. Tm's and free energies of duplex formation were obtained from fits of data to a two-state model with linear sloping baselines (Petersheim, M. and D. H. Turner, Biochemistry 1983, 22, 256–263). Results are averages of at least three experiments.

When the antisense oligonucleotides were hybridized to their complementary DNA sequences (synthesized as phosphodiesters), all of the antisense oligonucleotides with the exception of ISIS 1940 exhibited a Tm of at least 50° C. All the oligonucleotides should therefore be capable of hybridizing to the target ICAM-1 mRNA if the target sequences were exposed. Surprisingly, the potency of the antisense oligonucleotide did not correlate directly with either Tm or $\mathring{A}GE_{37}$. The oligonucleotide with the greatest biological activity, ISIS 1939, exhibited a Tm which was lower than that of the majority of the other oligonucleotides. Thus, hybridization affinity is not sufficient to ensure biological activity.

Figure 10:
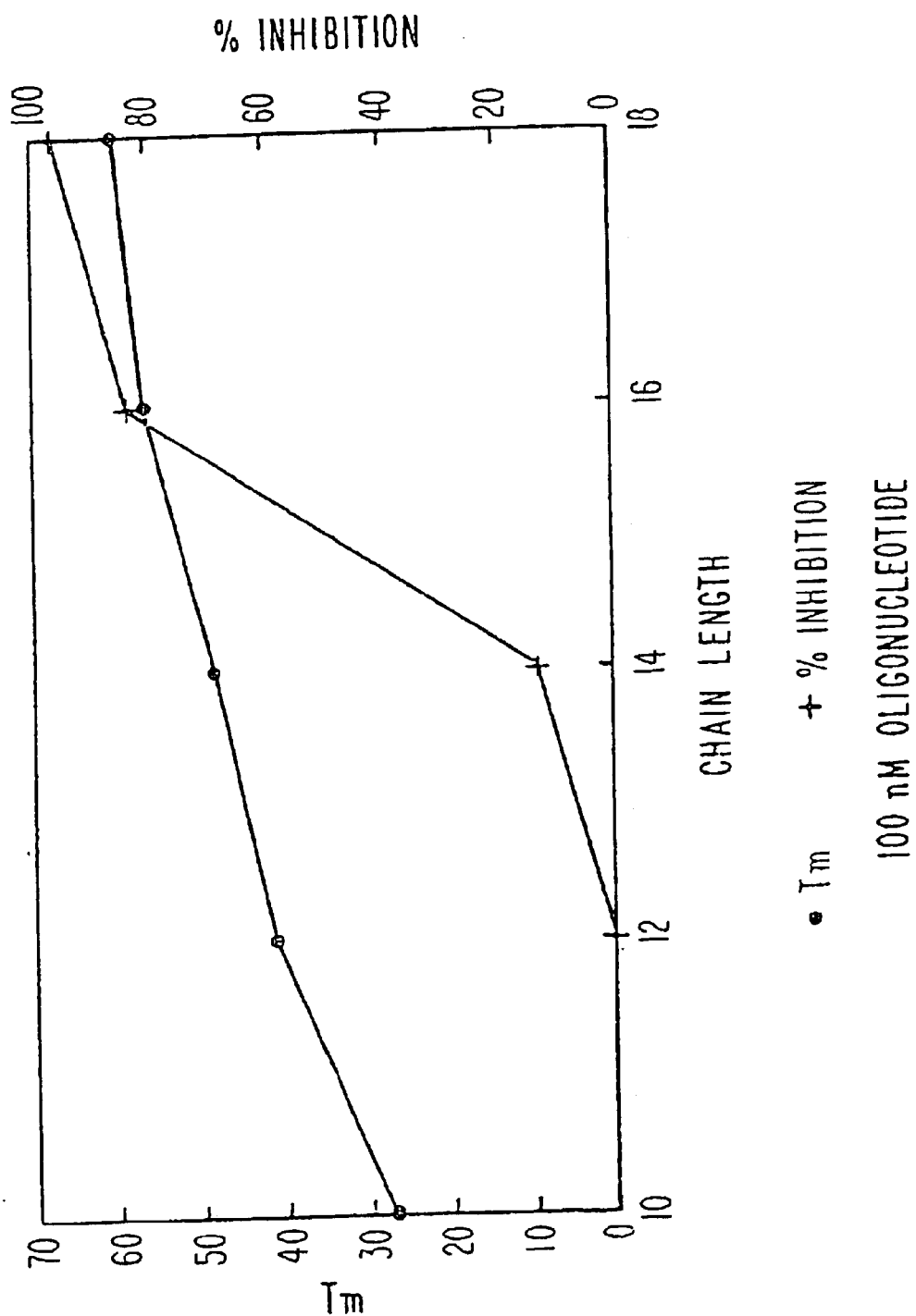
FIG. 10 is a graphical representation of the relationship between oligonucleotide chain length, Tm and effect on inhibition of ICAM-1 expression.

Example 9
Effect of Oligonucleotide Length on Antisense Inhibition of ICAM-1 Expression The effect of oligonucleotide length on antisense activity was tested using truncated versions of ISIS 1570 (ISIS 2165, 2173, 2149, 2163 and 2164) and ISIS 1939 (ISIS 2540, 2544, 2545, 2546, 2547 and 2548). In general, antisense activity decreased as the length of the oligonucleotides decreased. Oligonucleotides 16 bases in length exhibited activity slightly less than 18 base oligonucleotides. Oligonucleotides 14 bases in length exhibited significantly less activity, and oligonucleotides 12 or 10 bases in length exhibited only weak activity. Examination of the relationship between oligonucleotide length and Tm and antisense activity reveals that a sharp transition occurs between 14 and 16 bases in length, while Tm increases linearly with length (FIG. 10).

Example 10
Specificity of Antisense Inhibition of ICAM-1

The specificity of the antisense oligonucleotides ISIS 1570 and ISIS 1939 for ICAM-1 was evaluated by immunoprecipitation of $^{35}$S-labelled proteins. A549 cells were grown to confluence in 25 cm² tissue culture flasks and treated with antisense oligonucleotides as described in Example 4. The cells were stimulated with interleukin-1β for 14 hours, washed with methionine-free DMEM plus 10% dialyzed fetal calf serum, and incubated for 1 hour in methionine-free medium containing 10% dialyzed fetal calf serum, 1 μM oligonucleotide and interleukin-1β as indicated. $^{35}$S-Methionine/cysteine mixture (Tran$^{35}$S-label, purchased from ICN, Costa Mesa, Calif.) was added to the cells to an activity of 100 μCi/ml and the cells were incubated an additional 2 hours. Cellular proteins were extracted by incubation with 50 mM Tris-HCl pH 8.0, 150 mM NaCl, 1.0% NP-40, 0.5% deoxycholate and 2 mM EDTA (0.5 ml per well) at 4° C. for 30 minutes. The extracts were clarified by centrifugation at 18,000×g for 20 minutes. The supernatants were preadsorbed with 200 μl protein G-Sepharose beads (Bethesda Research Labs, Bethesda Md.) for 2 hours at 4° C., divided equally and incubated with either 5 μg ICAM-1 monoclonal antibody (purchased from AMAC Inc., Westbrook Me.) or HLA-A, B antibody (W6/32, produced by murine hybridoma cells obtained from the American Type Culture Collection, Bethesda, Md.) for 15 hours at 4° C. Immune complexes were trapped by incubation with 200 μl of a 50% suspension of protein G-Sepharose (v/v) for 2 hours at 4° C., washed 5 times with lysis buffer and resolved on an SDS-polyacrylamide gel. Proteins were detected by autoradiography.

Treatment of A549 cells with 5 units/ml of interleukin-1β was shown to result in the synthesis of a 95–100 kDa protein migrating as a doublet which was immunoprecipitated with the monoclonal antibody to ICAM-1. The appearance as a doublet is believed to be due to differently glycosylated forms of ICAM-1. Pretreatment of the cells with the antisense oligonucleotide ISIS 1570 at a concentration of 1 μM decreased the synthesis of ICAM-1 by approximately 50%, while 1 μM ISIS 1939 decreased ICAM-1 synthesis to near background. Antisense oligonucleotide ISIS 1940, inactive in the ICAM-1 ELISA assay (Examples 1 and 5) did not significantly reduce ICAM-1 synthesis. None of the antisense oligonucleotides hybridizable with ICAM-1 targets had a demonstrable effect on HLA-A, B synthesis, demonstrating the specificity of the oligonucleotides for ICAM-1. Furthermore, the proteins which nonspecifically precipitated with the ICAM-1 antibody and protein G-Sepharose were not significantly affected by treatment with the antisense oligonucleotides.

Figure 11:
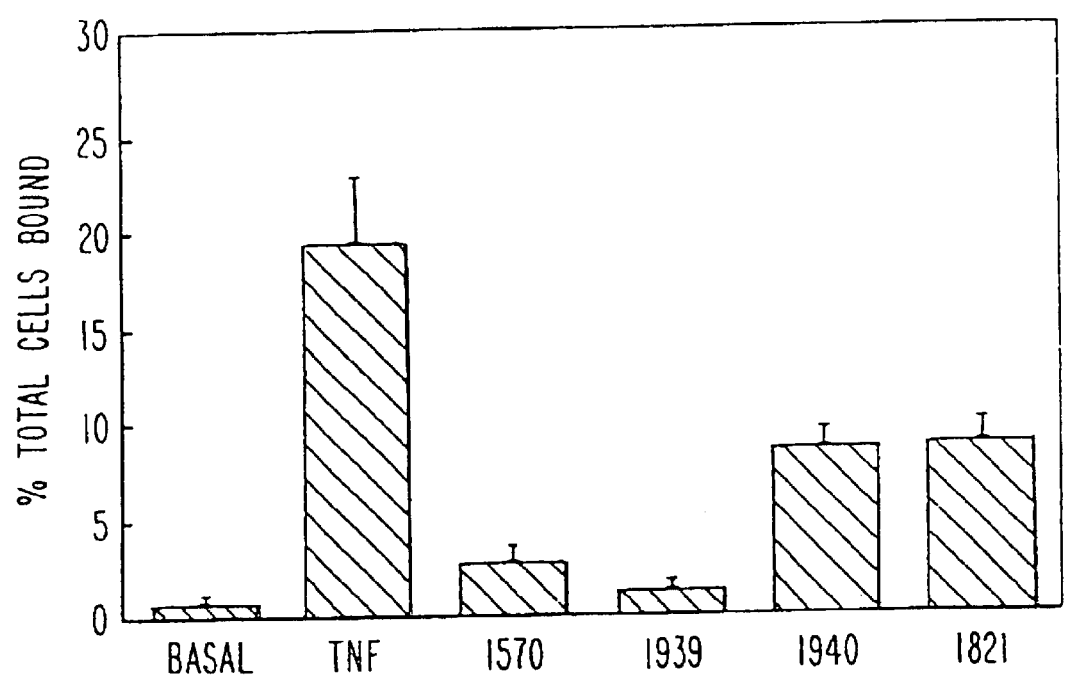
FIG. 11 is a graphical representation of the effect of selected antisense oligonucleotides on ICAM-1 mediated adhesion of DMSO differentiated HL-60 cells to control and tumor necrosis factor treated human umbilical vein endothelial cells.

Example 11
Screening of Additional Antisense Oligonucleotides for Activity Against ICAM-1 by Cell Adhesion Assay Human umbilical vein endothelial (HUVEC) cells were grown and treated with oligonucleotides as in Example 4. Cells were treated with either ISIS 1939, ISIS 1940, or the control oligonucleotide ISIS 1821 for 4 hours, then stimulated with TNF-α for 20 hours. Basal HUVEC minimally bound HL-60 cells, while TNF-stimulated HUVEC bound 19% of the total cells added. Pretreatment of the HUVEC monolayer with 0.3 ìM ISIS 1939 reduced the adherence of HL-60 cells to basal levels, as shown in FIG. 11. The control oligonucleotide, ISIS 1821, and ISIS 1940 reduced the percentage of cells adhering from 19% to 9%. These data indicate that antisense oligonucleotides targeting ICAM-1 may specifically decrease adherence of a leukocyte-like cell line (HL-60) to TNF-α-treated HUVEC.

Example 12
ELISA Screening of Antisense Oligonucleotides for Activity Against ELAM-1 Gene Expression Primary human umbilical vein endothelial (HUVEC) cells, passage 2 to 5, were plated in 96-well plates and allowed to reach confluence. Cells were washed three times with Opti-MEM (GIBCO, Grand Island N.Y.). Cells were treated with increasing concentrations of oligonucleotide diluted in Opti-MEM containing 10 μg/ml DOTMA solution (Bethesda Research Labs, Bethesda, Md.) for 4 hours at 370C. The medium was removed and replaced with EGM-UV (Clonetics, San Diego Calif.) plus oligonucleotide. Tumor necrosis factor α was added to the medium (2.5 ng/ml) and the cells were incubated an additional 4 hours at 37° C.

ELAM-1 expression was determined by ELISA. Cells were gently washed three times with Dulbecco's phosphate-buffered saline (D-PBS) prewarmed to 37° C. Cells were fixed with 95% ethanol at 4° C. for 20 minutes, washed three times with D-PBS and blocked with 2% BSA in D-PBS. Cells were incubated with ELAM-1 monoclonal antibody BBA-1 (R&D Systems, Minneapolis Minn.) diluted to 0.5 μg/ml in D-PBS containing 2% BSA for 1 hour at 37° C. Cells were washed three times with D-PBS and the bound ELAM-1 antibody detected with biotinylated goat anti-mouse secondary antibody followed by β-galactosidase-conjugated streptavidin as described in Example 1.

The activity of antisense phosphorothioate oligonucleotides which target 11 different regions on the ELAM-1 cDNA and two oligonucleotides which target ICAM-1 (as controls) was determined using the ELAM-1 ELISA. The oligonucleotide and targets are shown in Table 2.

TABLE 2

ANTISENSE OLIGONUCLEOTIDES WHICH TARGET HUMAN ELAM-1

| ISIS NO. | SEQ ID NO. | TARGET REGION | MODIFICATION |
|---|---|---|---|
| 1926 | 28 | AUG Codon (143–164) | P = S |
| 2670 | 29 | 3'-Untranslated (3718–3737) | P = S |
| 2673 | 30 | 3'-Untranslated (2657–2677) | P = S |
| 2674 | 31 | 3'-Untranslated (2617–2637) | P = S |
| 2678 | 32 | 3'-Untranslated (3558–3577) | P = S |
| 2679 | 33 | 5'-Untranslated (41–60) | P = S |
| 2680 | 34 | 3'-Untranslated (3715–3729) | P = S |
| 2683 | 35 | AUG Codon (143–163) | P = S |
| 2686 | 36 | AUG Codon (149–169) | P = S |
| 2687 | 37 | 5'-Untranslated (18–37) | P = S |
| 2693 | 38 | 3'-Untranslated (2760–2788) | P = S |
| 2694 | 39 | 3'-Untranslated (2934–2954) | P = S |

Figure 12:
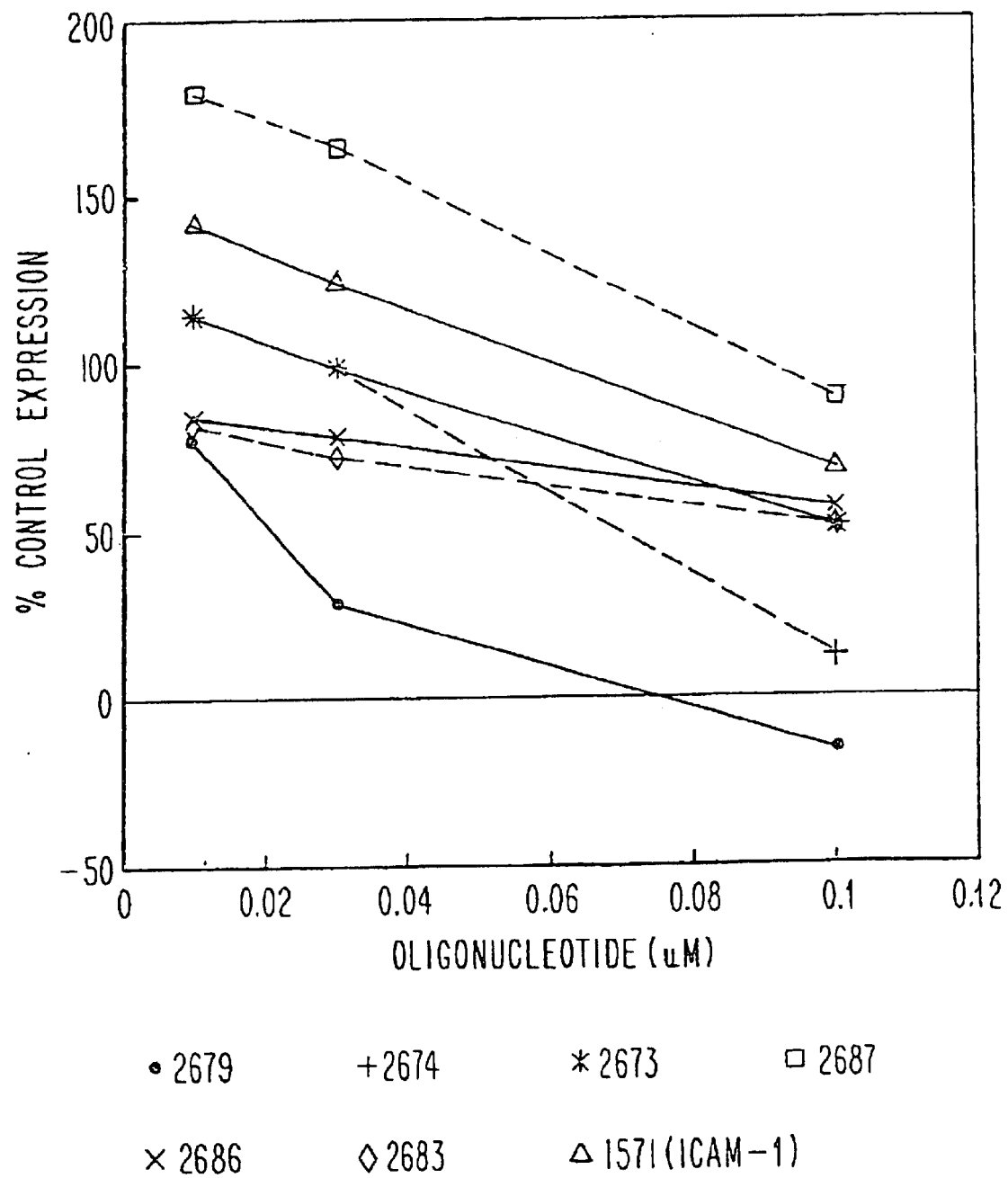
FIG. 12 is a graphical representation of the effects of selected antisense oligonucleotides on ELAM-1 expression on tumor necrosis factor-treated human umbilical vein endothelial cells.

In contrast to what was observed with antisense oligonucleotides targeted to ICAM-1 (Example 5), the most potent oligonucleotide modulator of ELAM-1 activity (ISIS 2679) was hybridizable with specific sequences in the 5'-untranslated region of ELAM-1. ISIS 2687, an oligonucleotide which hybridized to sequences ending three bases upstream of the ISIS 2679 target, did not show significant activity (FIG. 12). Therefore, ISIS 2679 hybridizes to a unique site on the ELAM-1 mRNA, which is uniquely sensitive to inhibition with antisense oligonucleotides. The sensitivity of this site to inhibition with antisense oligonucleotides was not predictable based upon RNA secondary structure predictions or information in the literature.

Example 13

Figure 13:
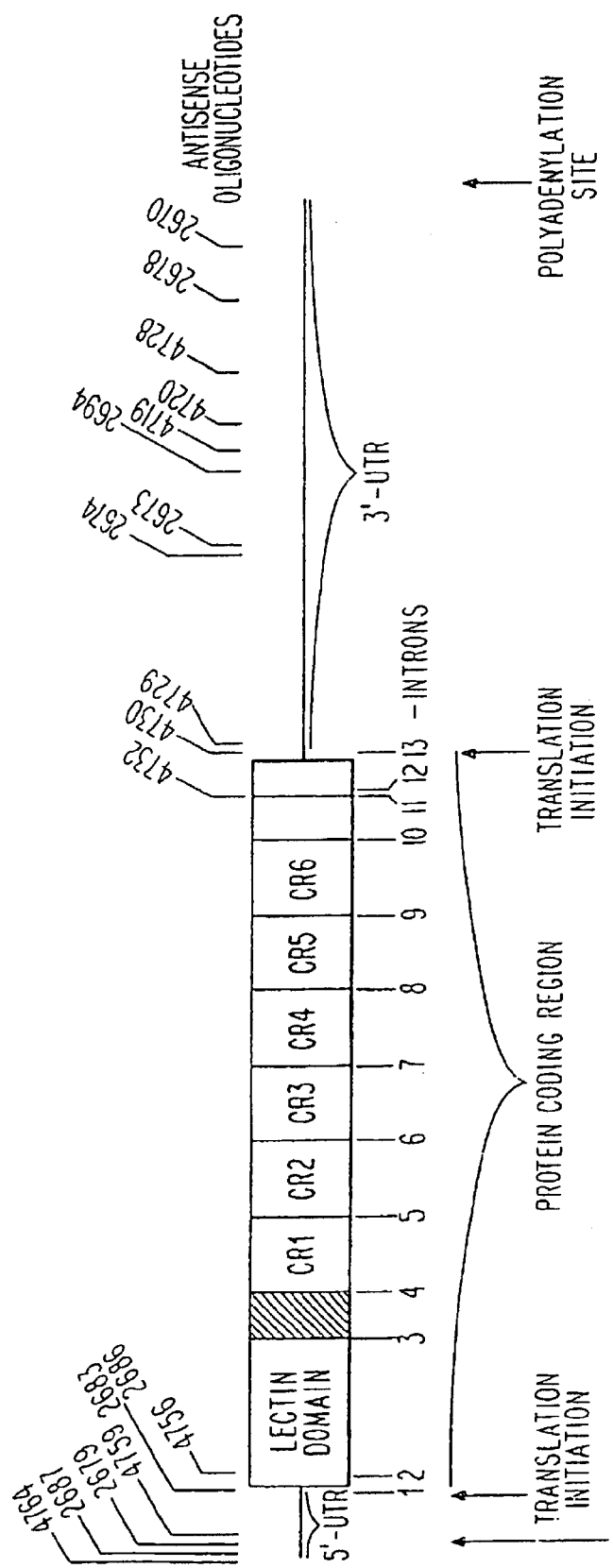
FIG. 13 is a graphical representation of the human ELAM-1 mRNA showing target sites of antisense oligonucleotides.

ELISA screening of additional antisense oligonucleotides for activity against ELAM-1 gene expression Inhibition of ELAM-1 expression by eighteen antisense phosphorothioate oligonucleotides was determined using the ELISA assay as described in Example 12. The target sites of these oligonucleotides on the ELAM-1 mRNA are shown in FIG. 13. The sequence and activity of each oligonucleotide against ELAM-1 are shown in Table 3. The oligonucleotides indicated by an asterisk (*) have IC50's of approximately 50 nM or below and are preferred. IC50 indicates the dosage of oligonucleotide, which results in 50% inhibition of ELAM-1 expression.

TABLE 3

INHIBITION OF HUMAN ELAM-1 EXPRESSION BY ANTISENSE OLIGONUCLEOTIDES
ELAM-1 expression is given as % of control

| ISIS# | SEQ ID NO: | POSITION | SEQUENCE | VCAM-1 EXPRESSION 30 nM oligo | 50 nM oligo |
|---|---|---|---|---|---|
| *4764 | 52 | 5'-UTR 1–19 | GAAGTCAGCCAAGAACAGCT | 70.2 | 50.2 |
| 2687 | 37 | 5'-UTR 17–36 | TATAGGAGTTTTGATGTGAA | 91.1 | 73.8 |

TABLE 3-continued

INHIBITION OF HUMAN ELAM-1 EXPRESSION BY ANTISENSE OLIGONUCLEOTIDES
ELAM-1 expression is given as % of control

| ISIS# | SEQ ID NO: | POSITION | SEQUENCE | VCAM-1 EXPRESSION 30 nM oligo | 50 nM oligo |
|---|---|---|---|---|---|
| *2679 | 33 | 5'-UTR 40-59 | CTGCTGCCTCTGTCTCAGGT | 6.4 | 6.0 |
| *4759 | 53 | 5'-UTR 64-83 | ACAGGATCTCTCAGGTGGGT | 30.0 | 20.2 |
| *2683 | 35 | AUG 143-163 | AATCATGACTTCAAGAGTTCT | 47.9 | 48.5 |
| *2686 | 36 | AUG 148-168 | TGAAGCAATCATGACTTCAAG | 51.1 | 46.9 |
| *4756 | 54 | I/E 177-196 | CCAAAGTGAGAGCTGAGAGA | 53.9 | 35.7 |
| 4732 | 55 | Coding 1936-1955 | CTGATTCAAGGCTTTGGCAG | 68.5 | 55.3 |
| *4730 | 56 | I/E 3'UTR 2006-2025 | TCCCCAGATGCACCTGTTT | 14.1 | 2.3 |
| *4729 | 57 | 3'-UTR 2063-2082 | GGGCCAGAGACCCGAGGAGA | 49.4 | 46.3 |
| *2674 | 31 | 3'-UTR 2617-2637 | CACAATCCTTAAGAACTCTTT | 33.5 | 28.1 |
| 2673 | 30 | 3'-UTR 2656-2676 | GTATGGAAGATTATAATATAT | 58.9 | 53.8 |
| 2694 | 39 | 3'-UTR 2933-2953 | GACAATATACAAACCTTCCAT | 72.0 | 64.6 |
| *4719 | 58 | 3'-UTR 2993-3012 | ACGTTTGGCCTCATGGAAGT | 36.8 | 34.7 |
| 4720 | 59 | 3'-UTR 3093-3112 | GGAATGCAAAGCACATCCAT | 63.5 | 70.6 |
| *2678 | 32 | 3'-UTR 3557-3576 | ACCTCTGCTGTTCTGATCCT | 24.9 | 15.3 |
| 2670 | 29 | 3'-UTR 3717-3736 | ACCACACTGGTATTTCACAC | 72.2 | 67.2 |

I/E indicates Intron/Exon junction
Oligonucleotides with IC50's of approximately 50 nM or below are indicated by an asterisk (*).

An additional oligonucleotide targeted to the 3'-untranslated region (ISIS 4728) did not inhibit ELAM expression.

Example 14

Figure 14:
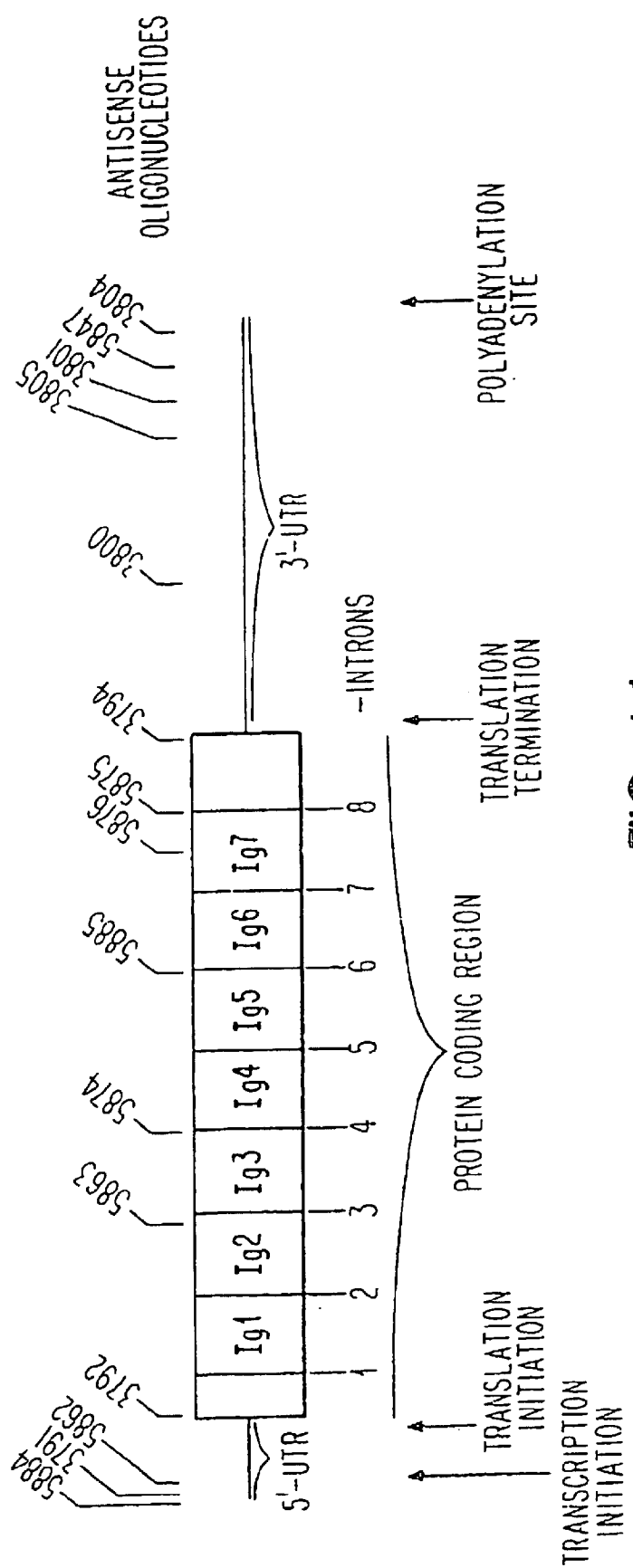
FIG. 14 is a graphical representation of the human VCAM-1 mRNA showing target sites of antisense oligonucleotides.

ELISA Screening of Antisense Oligonucleotides for Activity Against VCAM-1 Gene Expression Inhibition of VCAM-1 expression by fifteen antisense phosphorothioate oligonucleotides was determined using the ELISA assay approximately as described in Example 12, except that cells were stimulated with TNF-α for 16 hours and VCAM-1 expression was detected by a VCAM-1 specific monoclonal antibody (R & D Systems, Minneapolis, Minn.) used at 0.5 µg/ml. The target sites of these oligonucleotides on the VCAM-1 mRNA are shown in FIG. 14. The sequence and activity of each oligonucleotide against VCAM-1 are shown in Table 4. The oligonucleotides indicated by an asterisk (*) have IC50's of approximately 50 nM or below and are preferred. IC50 indicates the dosage of oligonucleotide which results in 50% inhibition of VCAM-1 expression.

TABLE 4

INHIBITION OF HUMAN VCAM-1 EXPRESSION BY ANTISENSE OLIGONUCLEOTIDES
VCAM-1 expression is given as % of control

| ISIS# | SEQ ID NO: | POSITION | SEQUENCE | VCAM-1 EXPRESSION 30 nM oligo | 50 nM oligo |
|---|---|---|---|---|---|
| *5884 | 60 | 5'-UTR 1-19 | CGATGCAGATACCGCGGAGT | 79.2 | 37.2 |
| 3791 | 61 | 5'UTR 38-58 | CCTGGGAGGGTATTCAGCT | 92.6 | 58.0 |
| 5862 | 62 | 5'-UTR 48-68 | CCTGTGTGTGCCTGGGAGGG | 115.0 | 3.5 |
| *3792 | 63 | AUG 110-129 | GGCATTTTAAGTTGCTGTCG | 68.7 | 33.7 |
| 5863 | 64 | CODING 745-764 | CAGCCTGCCTTACTGTGGGC | 95.8 | 66.7 |
| *5874 | 65 | CODING 1032-1052 | CTTGAACAATTAATTCCACCT | 66.5 | 35.3 |
| 5885 | 66 | E/I 1633-1649 + intron | TTACCATTGACATAAAGTGTT | 84.4 | 52.4 |
| *5876 | 67 | CODING 2038-2057 | CTGTGTCTCCTGTCTCCGCT | 43.5 | 26.6 |
| *5875 | 68 | CODING 2183-2203 | GTCTTTGTTGTTTTCTCTTCC | 59.2 | 34.8 |
| 3794 | 69 | TERMIN. 2344-2362 | TGAACATATCAAGCATTAGC | 75.3 | 52.6 |
| *3800 | 70 | 3'-UTR 2620-2639 | GCAATCTTGCTATGGCATAA | 64.4 | 47.7 |
| *3805 | 71 | 3'-UTR 2826-2845 | CCCGGCATCTTTACAAAACC | 7.7 | 44.9 |
| *3801 | 50 | 3'-UTR 2872-2892 | AACCCAGTGCTCCCTTTGCT | 36.5 | 21.3 |
| *5847 | 72 | 3'-UTR 2957-2976 | AACATCTCCGTACCATGCCA | 51.8 | 24.6 |
| *3804 | 51 | 3'-UTR 3005-3024 | GGCCACATTGGGAAAGTTGC | 55.1 | 29.3 |

E/I indicates exon/intron junction
Oligonucleotides with IC50's of approximately 50 nM or below are indicated by an asterisk (*).

Example 15

ICAM-1 Expression in C8161 Human Melanoma Cells

Human melanoma cell line C8161 (a gift of Dr. Dan Welch, Hershey Medical Center) was derived from an abdominal wall metastasis from a patient with recurrent malignant melanoma. These cells form multiple metastases in lung, subcutis, spleen, liver and regional lymph nodes after subcutaneous, intradermal and intravenous injection into athymic nude mice. Cells were grown in DMA-F12 medium containing 10% fetal calf serum and were passaged using 2 mM EDTA.

Exposure of C8161 cells to TNF-α resulted in a six-fold increase in cell surface expression of ICAM-1 and an increase in ICAM-1 mRNA levels in these cells. ICAM-1 expression on the cell surface was measured by ELISA. Cells were treated with increasing concentrations of antisense oligonucleotides in the presence of 15 µg/ml Lipofectin for 4 hours at 37° C. ICAM-1 expression was induced by incubation with 5 ng/ml TNF-α for 16 hours. Cells were washed 3× in DPBS and fixed for 20 minutes in 2% formaldehyde. Cells were washed in DPBS, blocked with 2% BSA for 1 hour at 37° C. and incubated with ICAM-1 monoclonal antibody 84H10 (AMAC, Inc., Westbrook, Me.). Detection of bound antibody was determined by incubation with a biotinylated goat anti-mouse IgG followed

Figure 15:
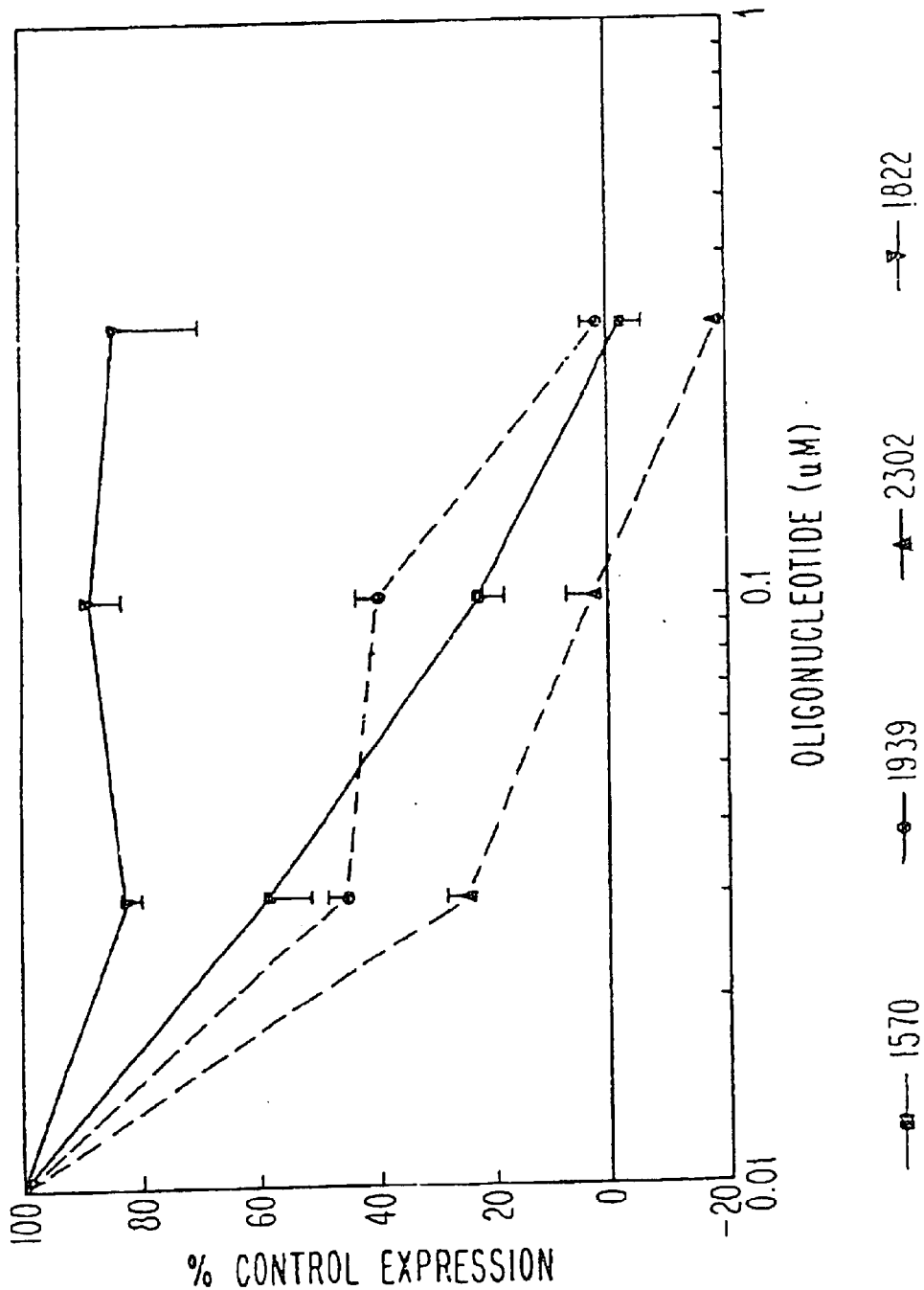
FIG. 15 is a line graph showing inhibition of ICAM-1 expression in C8161 human melanoma cells following treatment with antisense oligonucleotides complementary to ICAM-1.

Example 16
Oligonucleotide Inhibition of ICAM-1 Expression in C8161 Human Melanoma Cells As shown in FIG. 15, antisense oligonucleotides ICAM 1570 (SEQ ID NO: 1), ISIS 1939 (SEQ ID NO: 15) and ISIS 2302 (SEQ ID NO: 22) targeted to ICAM-1 decreased cell surface expression of ICAM-1 (detected by ELISA as in Example 16). ISIS 1822, a negative control oligonucleotide complementary to 5-lipoxygenase, did not affect ICAM-1 expression. The data were expressed as percentage of control activity, calculated as follows: (ICAM-1 expression for oligonucleotide-treated, cytokine-induced cells)−(basal ICAM-1 expression)/(ICAM-1 cytokine-induced expression)−(basal ICAM-1 expression)×100.

ISIS 1939 (SEQ ID NO: 15) and ISIS 2302 (SEQ ID NO: 22) markedly reduced ICAM-1 mRNA levels (detected by Northern blot analysis), but ISIS 1570 (SEQ ID NO: 1) decreased ICAM-1 mRNA levels only slightly.

Example 17
Experimental Metastasis Assay

To evaluate the role of ICAM-1 in metastasis, experimental metastasis assays were performed by injecting 1×10$^5$ C8161 cells into the lateral tail vein of athymic nude mice. Treatment of C8161 cells with the cytokine TNF-α and interferon α has previously been shown to result in an increased number of lung metastases when cells were injected into nude mice [Miller, D. E. and Welch, D. R., *Proc. Am. Assoc. Cancer Res.* 1990, 13, 353].

After 4 weeks, mice were sacrificed, organs were fixed in Bouin's fixative and metastatic lesions on lungs were scored with the aid of a dissecting microscope. Four-week-old female athymic nude mice (Harlan Sprague Dawley) were used. Animals were maintained under the guidelines of the NIH. Groups of 4–8 mice each were tested in experimental metastasis assays.

Example 18
Antisense Oligonucleotides ISIS 1570 and ISIS 2302 Decrease Metastatic Potential of C8161 Cells Treatment of C8161 cells with antisense oligonucleotides ISIS 1570 and ISIS 2302, complementary to ICAM-1, was performed in the presence of the cationic lipid, Lipofectin (Gibco/BRL, Gaithersburg, Md.). Antisense oligonucleotides were synthesized as described in Example 3. Cells were seeded in 60 mm tissue culture dishes at 106 cells/ml and incubated at 370C for 3 days, washed with OPTI-MEM (Gibco/BRL) 3 times and 100 μl of OPTI-MEM medium was added to each well. 0.5 μM oligonucleotide and 15 μg/ml lipofectin were mixed at room temperature for 15 minutes. 25 μl of the oligonucleotide-lipofectin mixture was added to the appropriate dishes and incubated at 37° C. for 4 hours. The oligonucleotide-lipofectin mixture was removed and replaced with DME-F12 medium containing 10% fetal calf serum. After 4 hours, 500 U/ml TNF-α was added to the appropriate wells and incubated for 18 hours at which time cells were removed from the plates, counted and injected into athymic nude mice.

Treatment of C8161 cells with ISIS 1570 (SEQ ID NO: 1) or ISIS 2302 (SEQ ID NO: 22) decreased the metastatic potential of these cells, and eliminated the enhanced metastatic ability of C8161 which resulted from TNF-a treatment. Data are shown in Table 5.

TABLE 5

EFFECT OF ANTISENSE OLIGONUCLEOTIDES TO ICAM-1 ON EXPERIMENTAL METASTASIS OF HUMAN MELANOMA CELL LINE C8161

| Treatment | No. Lung Metastases per Mouse (Mean ± S.E.M.) |
|---|---|
| Lipofectin only | 64 ± 13 |
| Lipofectin + TNF-á | 81 ± 8 |
| ISIS-1570 + Lipofectin | 38 ± 15 |
| ISIS-2302 + Lipofectin | 23 ± 6 |
| ISIS-1570 + Lipofectin + TNF-á | 49 ± 6 |
| ISIS-2302 + Lipofectin + TNF-á | 31 ± 8 |

Example 19
Murine Models for Testing Antisense Oligonucleotides Against ICAM-1

Many conditions which are believed to be mediated by intercellular adhesion molecules are not amenable to study in humans. For example, allograft rejection is a condition which is likely to be ameliorated by interference with ICAM-1 expression, but clearly this must be evaluated in animals rather than human transplant patients. Another such example is inflammatory bowel disease, and yet another is neutrophil migration (infiltration). These conditions can be tested in animal models, however, such as the mouse models used here. Oligonucleotide sequences for inhibiting ICAM-1 expression in murine cells were identified. Murine ICAM-1 has approximately 50% homology with the human ICAM-1 sequence; a series of oligonucleotides which target the mouse ICAM-1 mRNA sequence were designed and synthesized, using information gained from evaluation of oligonucleotides targeted to human ICAM-1. These oligonucleotides were screened for activity using an immunoprecipitation assay.

Murine DCEK-ICAM-1 cells (a gift from Dr. Adrienne Brian, University of California at San Diego) were treated with 1 μM of oligonucleotide in the presence of 20 μg/ml DOTMA/DOPE solution for 4 hours at 37° C. The medium was replaced with methionine-free medium plus 10% dialyzed fetal calf serum and 1 μM antisense oligonucleotide. The cells were incubated for 1 hour in methionine-free medium, then 100 μCi/ml $^{35}$S-labeled methionine/cysteine mixture was added to the cells. Cells were incubated an additional 2 hours, washed 4 times with PBS, and extracted with buffer containing 20 mM Tris, pH 7.2, 20 mM KCl, 5 mM EDTA, 1% Triton X-100, 0.1 mM leupeptin, 10 μg/ml aprotinin, and 1 mM PMSF. ICAM-1 was immunoprecipitated from the extracts by incubating with a murine-specific ICAM-1 antibody (YN1/1.7.4) followed by protein G-sepharose. The immunoprecipitates were analyzed by SDS-PAGE and autoradiographed. Phosphorothioate oligonucleotides ISIS 3066 and 3069, which target the AUG codon of mouse ICAM-1, inhibited ICAM-1 synthesis by 48% and 63%, respectively, while oligonucleotides ISIS 3065 and ISIS 3082, which target sequences in the 3'-untranslated region of murine ICAM-1 mRNA inhibited ICAM-1 synthesis by 47% and 97%, respectively. The most active antisense oligonucleotide against mouse ICAM-1 was targeted to the 3'-untranslated region. ISIS 3082 was evaluated further based on these results; this 20-mer phosphorothioate oligonucleotide comprises the sequence (5' to 3') TGC ATC CCC CAG GCC ACC AT (SEQ ID NO: 83).

Example 20
Antisense Oligonucleotides to ICAM-1 Reduce Inflammatory Bowel Disease in Murine Model System A mouse model for inflammatory bowel disease (IBD) has recently been developed. Okayasu et al., *Gastroenterology* 1990, 98, 694–702. Administration of dextran sulfate to mice induces colitis that mimics human IBD in almost every detail. Dextran sulfate-induced IBD and human IBD have subsequently been closely compared at the histological level and the mouse model has been found to be an extremely reproducible and reliable model. It is used here to test the effect of ISIS 3082, a 20-base phosphorothioate antisense oligonucleotide which is complementary to the 3' untranslated region of the murine ICAM-1.

Female Swiss Webster mice (8 weeks of age) weighing approximately 25 to 30 grams are kept under standard conditions. Mice are allowed to acclimate for at least 5 days before initiation of experimental procedures. Mice are given 5% dextran sulfate sodium in their drinking water (available ad libitum) for 5 days. Concomitantly, ISIS 3082 oligonucleotide in pharmaceutical carrier, carrier alone (negative control) or TGF-$\beta$ (known to protect against dextran sulfate-mediated colitis in mice) is administered. ISIS 3082 was given as daily subcutaneous injection of 1 mg/kg or 10 mg/kg for 5 days. TGF-$\beta$ was given as 1 $\mu$g/mouse intracolonically. At 1 mg/kg, the oligonucleotide was as effective as TGF-$\alpha$ in protecting against dextran-sulfate-induced colitis.

Figure 16:
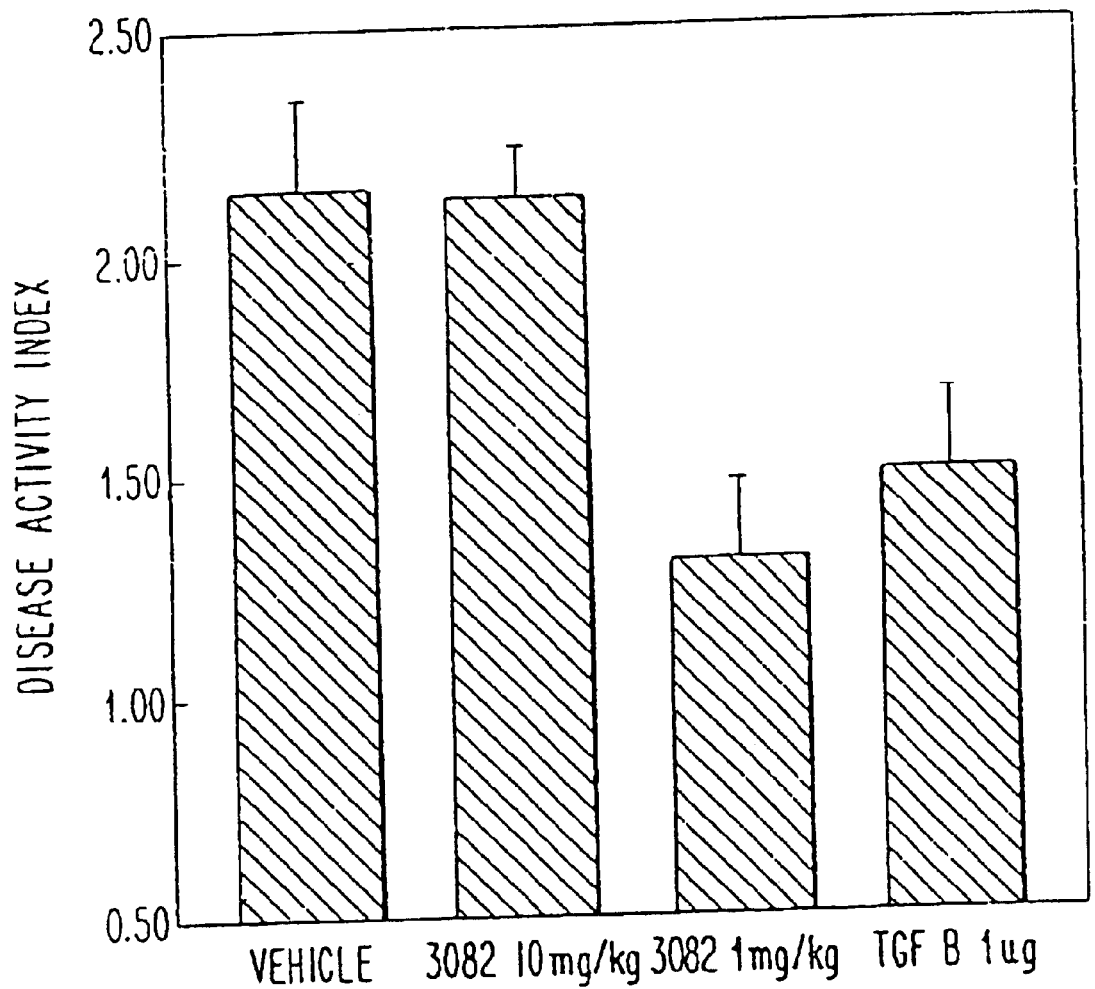
FIG. 16 is a bar graph showing the effect of ISIS 3082 on dextran sulfate (DSS)-induced inflammatory bowel disease.

Mice were sacrificed on day 6 and colons were subjected to histopathologic evaluation. Until sacrifice, disease activity was monitored by observing mice for weight changes and by observing stools for evidence of colitis. Mice were weighed daily. Stools were observed daily for changes in consistency and for presence of occult or gross bleeding. A scoring system was used to develop a disease activity index by which weight loss, stool consistency and presence of bleeding were graded on a scale of 0 to 3 (0 being normal and 3 being most severely affected) and an index was calculated. Drug-induced changes in the disease activity index were analyzed statistically. The disease activity index has been shown to correlate extremely well with IBD in general. Results are shown in FIG. 16. At 1 mg/kg, the oligonucleotide reduced the disease index by 40%.

Example 21
Antisense Oligonucleotide to ICAM-1 Increases Survival in Murine Heterotopic Heart Transplant Model To determine the therapeutic effects of ICAM-1 antisense oligonucleotide in preventing allograft rejection the murine ICAM-1 specific oligonucleotide ISIS 3082 was tested for activity in a murine vascularized heterotopic heart transplant model. Hearts from Balb/c mice were transplanted into the abdominal cavity of C3H mice as primary vascularized grafts essentially as described by Isobe et al., *Circulation* 1991, 84, 1246–1255. Oligonucleotides were administered by continuous intravenous administration via a 7-day Alzet pump. The mean survival time for untreated mice was 9.2±0.8 days (8, 9, 9, 9, 10, 10 days). Treatment of the mice for 7 days with 5 mg/kg ISIS 3082 increased the mean survival time to 14.3±4.6 days (11, 12, 13, 21 days).

Example 22
Antisense Oligonucleotide to ICAM-1 Decreases Leukocyte Migration Leukocyte infiltration of tissues and organs is a major aspect of the inflammatory process and contributes to tissue damage resulting from inflammation. The effect of ISIS 3082 on leukocyte migration was examined using a mouse model in which carrageenan-soaked sponges were implanted subcutaneously. Carrageenan stimulates leukocyte migration and edema. Effect of oligonucleotide on leukocyte migration in inflammatory exudates is evaluated by quantitation of leukocytes infiltrating the implanted sponges. Following a four hour fast, 40 mice were assigned randomly to eight groups each containing five mice. Each mouse was anesthetized with Metofane and a polyester sponge impregnated with 1 ml of a 20 mg/ml solution of carrageenan was implanted subcutaneously. Saline was administered intravenously to Group 1 at 10 ml/kg four hours prior to sponge implantation and this served as the vehicle control. Indomethacin (positive control) was administered orally at 3 mg/kg at a volume of 20 ml/kg to Group 2 immediately following surgery, again 6–8 hours later and again at 21 hours post-implantation. ISIS 3082 was administered intravenously at 5 mg/kg to Group 3 four hours prior to sponge implantation. ISIS 3082 was administered intravenously at 5 mg/kg to Group 4 immediately following sponge implantation. ISIS 3082 was administered intravenously at 5 mg/kg to Groups 5, 6, 7 and 8 at 2, 4, 8 and 18 hours following sponge implantation, respectively. Twenty-four hours after implantation, sponges were removed, immersed in EDTA and saline (5 ml) and squeezed dry. Total numbers of leukocytes in sponge exudate mixtures were determined.

The oral administration of indomethacin at 3 mg/kg produced a 79% reduction in mean leukocyte count when compared to the vehicle control group.

A 42% reduction in mean leukocyte count was observed following the administration of ISIS 3082 at 5 mg/kg four hours prior to sponge implantation (Group 3). A 47% reduction in mean leukocyte count was observed following the administration of ISIS 3082 at 5 mg/kg immediately following sponge implantation (Group 4). All animals appeared normal throughout the course of study.

Example 23
Compatibility of Antisense Oligonucleotide with Corneal Donor Storage Media and Determination of Toxicity The following studies were performed to determine whether antisense oligonucleotides were toxic to normal ocular tissues. A 20-mer antisense phosphorothioate oligonucleotide (APO) in three different concentrations (40, 200 and 400 $\mu$g/ml) was stored in OPTISOL™ corneal donor storage media (Bausch & Lomb) for a total of 30 days. At day 0, 2, 8 and 30 of incubation, aliquots from each concentration were removed, 2 ml samples were placed in freezer-safe tubes and frozen at −100° C. for storage. Samples were thawed and analyzed by capillary gel electrophoresis (CGE). Another 2 ml aliquot was obtained for each day for analysis of degradability using by spectrophotometry at 260 nm. The dose response curve in water was linear from 5–200 $\mu$g/ml concentrations. The samples containing OPTISOL™ were diluted 1:10 to decrease interference in the spectrophotometer.

No degradation or breakdown components of APO over the 30-day storage period was detected by CGE; however, degradation was observed when analysis was performed by spectrophotometry as indicated as decreased absorbance. Absorbance decreased by 39% after 8 days in the 400 $\mu$g/ml samples, 37% in the 200 g/ml samples and 60% in the 40 $\mu$g/ml samples on average. Thus, at the concentrations studied, the APO is stable in OPTISOL™ and does not appear to break down as determined by CGE.

Human donor corneas that were unsuitable for transplant were incubated with 3 different concentrations of APO in OPTISOL™ and evaluated after 1, 3 and 8 days using the same criteria applied to corneas for transplant. Corneas were fixed for histologic evaluation by light and electron microscopy. Although all corneas deteriorated over time, low concentrations of APO did not significantly affect either epithelial or endothelial cellular integrity, deturgescence or tissue viability. Thee results for the 1 and 8 day incubations are summarized in Table 6.

TABLE 6

CORNEAL CHANGES OBSERVED AFTER STORAGE FOR 24 HOURS OR 8 DAYS BY LIGHT MICROSCOPY ANALYSIS

|  | Edema | Epithelial defect | Inflammation | Absence of polarity |
| --- | --- | --- | --- | --- |
| APO (24 h) | 1/7 | 2/7 | 2/7 | 3/7 |
| Control (24 h) | 0/2 | 1/2 | 0/2 | 0/2 |
| APO (8 days) | 3/9 | 1/9 | 0/9 | 7/9 |
| Control (8 days) | 1/11 | 2/11 | 3/11 | 9/11 |

Rabbits were treated with topical doses (200 and 400 g/ml) of APO for 10 days four times per day. A different concentration was used in each of the two groups. The ocular surface was assessed by clinical examination using the MacDonald-Shadduck toxicology scale. No local toxicity was reported on the MacDonald-Shadduck scale or by light microscopy. The results are shown in Table 7.

TABLE 7

MACDONALD-SHADDUCK OCULAR IRRITATION SCORES

|  | Control[1] | APO (40 µg/ml) | APO (400 µg/ml) |
| --- | --- | --- | --- |
| Conjunctiva: | | | |
| Injection | Normal | Minor[2] | Minor |
| Chemosis/Swelling | Normal | Minor[3] | Minor |
| Discharge | None | Minimal | Minimal |
| Light reflex | Normal | Normal | Slightly sluggish (day 4–8) |
| Cornea: | | | |
| Loss of transparency | None | Minimal (d. 6–7)[4] | Minimal (d. 2–8) |
| Stromal opacity | None | Minimal (d. 7–8)[5] | Moderate (d. 2–8)[5] |
| Vascularization | None | None | Minimal[6] |
| Staining | None | None | None |

[1]Vehicle-treated control
[2]Less than 0.5 on a scale of 3.0 = minor flushing of palpebral conjunctiva with some perilimbal injection
[3]Less than 0.5 on a scale of 4.0 = some swelling without eversion of the lids
[4]Less than 0.5 on a scale of 4.0 = some loss of transparency in anterior half of stroma on days 7–8
[5]Minimal >0.5 on a scale of 4.0 = >10% area of stromal cloudiness
[6]Moderate 1.0 on a scale of 4.0 = <25% area of stromal cloudiness In addition, serum and aqueous humor were withdrawn and analyzed for the presence of APO to evaluate the ability to penetrate through the corneal tissues. The amount of APO in the serum was less than the limit of detection of the assay method. Significant amounts of APO were found to have penetrated into the aqueous humor, demonstrating the ability of the APO to penetrate through the cornea. After 10 days, the cornea and conjunctiva were studied by light and electron microscopy. By specular microscopy, there were no significant differences between corneas incubated in OPTISOL™ alone or with APO. Light microscopy demonstrated that epithelial polarity and thickness was unaffected by 200 µg/ml and was minimally affected at 400 µg/ml. Scanning electron microscopy (SEM) indicated that storage of corneas up to 8 days did not further increase the time related corneal endothelial degradation.

The experiments described above show that the antisense phosphorothioate oligonucleotides are compatible with corneal storage media, are not toxic to human corneas stored in corneal storage media and are not damaging to normal eye tissue when applied topically.

Example 24

Effect of ISIS 2302 on Corneal Integrity and Tissue Viability

Eleven human corneal donor buttons were stored in TM OPTISOL™ for 8 days and used as the control group. Additional corneal buttons were used for the experimental group and were stored in OPTISOL™ with either 200 µg/ml ISIS 2302 (n=10) or 400 µg/ml ISIS 2302 (n=8). Endothelial cell density was evaluated by specular microscopy. After 8 days, all corneas were prepared for SEM and photographs were taken of endothelial and epithelial surfaces.

Analysis by specular microscopy found that after 2 or 8 days of storage, there was no difference in endothelial cell density among the 3 groups. Both surfaces of the control and experimental groups were analyzed for cellular degradation as well as similarities and differences in their appearance. SEM revealed heavy exfoliation of the epithelial surface of the control group and moderate to heavy pitting and enucleation of the endothelial surface. The corneal buttons exposed to 200 or 400 µg/ml ISIS 2302 were similar in appearance to corneas in the control group. Severe pitting and hollowing of the endothelial surface and shedding of the epithelial surface seem to be consistent in both the control and experimental groups.

Although there were no obvious differences between the experimental and control groups, it should be noted that all corneal buttons were 1–2 days out of the orbit before experimentation began. Furthermore, after eight days in storage, sloughing and loss of the surface cells are to be expected. Thus, ISIS 2302 is not markedly toxic to stored human corneas.

Example 25

Effects of ICAM-1 Antisense Oligonucleotides (ISIS 9125 and 2105) on Allograft Rejection The following study was preformed to determine whether pretreating corneal allografts with the rat ICAM-1 antisense oligonucleotides ISIS 9125 (5'-AGGGCCACTGCTCGTCCACA-3', all 2'-deoxyphosphorothioate) (SEQ ID NO: 86) and ISIS 2105 inhibited corneal allograft rejection. Rejection was induced in rat corneas by removing the corneas from anesthetized donor ACI rats and transplanting them to anesthetized recipient Lewis rats. In this model of corneal transplant rejection, Lewis rat recipients normally produce a rejection reaction within 6–8 days. The cornea transplants were performed after pretreatment of the donor ACI corneas with either ISIS 9125 or with vehicle (Optisol™) alone. Under surgical anesthesia (ketamine 80 mg/kg, acepromazine 12 mg/kg), a 3 mm section of cornea was removed from one eye of the recipient rat, without damaging internal eye structures. Using the operating microscope, the donor corneal allograft was fitted over the recipient's corneal opening, and 8 to 12 sutures placed aseptically to secure the corneal allograft. Once sutures were in place, the anterior chamber was re-inflated using sterile saline, and tobramycin antibiotic ointment with dexamethasone was applied to the surgical site. The animals were allowed to recover and respiration and behavior were monitored. Some donor corneas were incubated in OPTISOL™ containing 400 µg/ml ISIS 9125 for 24 hours before transplantation.

Rats were examined post-op by slit lamp and rejection was based on the MacDonald-Shadduck scale modified for corneal graft rejection. Rejection criteria included corneal opacity, neovascularization, keratic precipitates and conjunctival inflammation. Following rejection, corneas were harvested for examination under light microscopy (H&E) and SEM. Some corneas were harvested on post-op day 3 for histologic examination. Confocal microscopy was used to document epithelial and endothelial changes in vivo.

Corneas transplanted immediately after removal from donor rats rejected an average of 5.94 days (range 4–8 days), while those treated with topical steroid lasted an average of 8.40 days (range 6–11 days). The group whose corneas were incubated in OPTISOL™ for 24 hours rejected an average of 4.80 days (range 3–7 days). Those whose corneas were incubated in OPTISOL™ plus ISIS 9125 for 24 hours rejected an average of 6.33 days (range 6–10 days). By day 3 post-surgery, the ISIS 9125 plus OPTISOL™ group was graded 50% better than the OPTISOL™ alone group for cornea opacity and neovascularization; however, the ISIS 9125 group had more corneal edema than the OPTISOL™ alone group.

A similar procedure was used with ISIS 2105 as the antisense oligonucleotide. The percent of allograft recipients showing no signs of rejection 3 days post-op in category is shown in Table 8.

TABLE 8

PERCENT OF ALLOGRAFT RECIPIENTS SHOWING NO SIGNS OF REJECTION 3 DAYS POST-OP IN CATEGORY

| Examination item | No pre/post treatment | Post-op steroids alone | 24 hr pre-op Optisol storage alone | 24 hr pre-op ISIS/Optisol storage |
|---|---|---|---|---|
| Conjunctival congestion | 100 | 100 | 100 | 100 |

TABLE 8-continued

PERCENT OF ALLOGRAFT RECIPIENTS SHOWING NO SIGNS OF REJECTION 3 DAYS POST-OP IN CATEGORY

| Examination item | No pre/post treatment | Post-op steroids alone | 24 hr pre-op Optisol storage alone | 24 hr pre-op ISIS/Optisol storage |
|---|---|---|---|---|
| Conjunctival discharge | 88 | 100 | 100 | 100 |
| Iris | 100 | 100 | 100 | 100 |
| Graft opacity | 44 | 67 | 50 | 80 |
| Graft edema | 25 | 33 | 0 | 40 |
| Graft neovascularization | 0 | 67 | 50 | 100 |
| Graft staining | 94 | 83 | 100 | 100 |
| Keratic precips | 100 | 100 | 100 | 100 |

The data show the ability of ISIS 9125 and 2105 to inhibit corneal rejection. Data with steroids, which increased days to rejection by 30%, confirms the validity of the transplant model. ISIS 9125 increased days to rejection by 25% over the 24 hour OPTISOL™ incubation control group. More subtle signs of inflammation were documented in vivo by confocal microscopy than could be detected by slit lamp. Although the allograft experiments were conducted with ISIS 9125, the use of other antisense oligonucleotides targeted to cellular adhesion molecules, particularly ICAM-1, VCAM-1 and ELAM-1, for inhibiting corneal allograft rejection is also within the scope of the present invention. The ability of any antisense oligonucleotide targeted to a cell adhesion molecule to inhibit corneal allograft rejection can be easily determined without undue experimentation by using the protocols described in the present application.

What is claimed is:

1. A method for preserving a corneal explant ex vivo, comprising incubating a corneal explant in a solution comprising a corneal storage medium and an antisense oligonucleotide between 8 and 50 nucleotides in length that is targeted to intercellular adhesion molecule-1 (ICAM-1), and wherein said antisense oligonucleotide inhibits the expression of intercellular adhesion molecule-1 (ICAM-1), and wherein inhibition of ICAM-1 expression results in preserving a corneal, explant ex vivo.

2. The method of claim 1, wherein said antisense oligonucleotide is SEQ ID NO: 22.

3. The method of claim 1, wherein said explant is a human explant.

4. A method of inhibiting corneal allograft rejection, comprising contacting a corneal allograft with a topical formulation comprising an antisense oligonucleotide between 8 and 50 nucleotides in length that is targeted to intercellular adhesion molecule-1 (ICAM-1), and wherein said antisense oligonucleotide inhibits the expression of intercellular adhesion molecule-1 (ICAM-1), and wherein inhibition of ICAM-1 expression results in corneal allograft rejection inhibition.

5. The method of claim 4, wherein said antisense oligonucleotide is SEQ ID NO: 22.

6. The method of claim 4, wherein the allograft is a human allograft.

7. The method of claim 4, wherein the topical formulation is a solution.

8. A method for preserving a corneal explant ex vivo, comprising incubating a corneal, explant in a solution comprising a corneal storage medium and an antisense oligonucleotide between 8 and 50 nucleotides in length that is targeted to extracellular adhesion molecule-1 (ELAM-1) or vascular cell adhesion molecule-1 (VCAM-1), and wherein said antisense oligonucleotide inhibits the expression of extracellular adhesion molecule-1 (ELAM-1) or vascular cell adhesion molecule-1 (VCAM-1), and wherein inhibition of ELAM-1 and VCAM-1 expression results in preserving a corneal explant ex vivo.

9. The method of claim 8, wherein the explant is a human explant.

* * * * *

SEQUENCE LISTING

<160> NUMBER OF SEQ ID NOS: 92

<210> SEQ ID NO 1
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 1
tgggagccat agcgaggc                                             18

<210> SEQ ID NO 2
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 2
gaggagctca gcgtcgactg                                           20

<210> SEQ ID NO 3
<211> LENGTH: 21
<212> TYPE: DNA
<213> ORGANISM: Artificial Sequence
<220> FEATURE:
<223> OTHER INFORMATION: Antisense oligonucleotide

```
<400> SEQUENCE: 3
gacactcaat aaatagctgg t                                              21

<210> SEQ ID NO 4
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 4
gaggctgagg tgggagga                                                  18

<210> SEQ ID NO 5
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 5
cgatgggcag tgggaaag                                                  18

<210> SEQ ID NO 6
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 6
gggcgcgtga tccttatagc                                                20

<210> SEQ ID NO 7
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 7
catagcgagg ctgaggttgc                                                20

<210> SEQ ID NO 8
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 8
cgggggctgc tgggagccat                                                20

<210> SEQ ID NO 9
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 9
agagccccga gcaggaccag                                                20

<210> SEQ ID NO 10
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 10
tgcccatcag ggcagtttga                                               20

<210> SEQ ID NO 11
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 11
ggtcacactg actgaggcct                                               20

<210> SEQ ID NO 12
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 12
ctcgcgggtg acctcccctt                                               20

<210> SEQ ID NO 13
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 13
tcagggaggc gtggcttgtg                                               20

<210> SEQ ID NO 14
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 14
cctgtcccgg gataggttca                                               20

<210> SEQ ID NO 15
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 15
cccccaccac ttcccctctc                                               20

<210> SEQ ID NO 16
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 16
```

```
ttgagaaagc tttattaact                                          20

<210> SEQ ID NO 17
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 17
agccatagcg aggc                                                14

<210> SEQ ID NO 18
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 18
ccatagcgag gc                                                  12

<210> SEQ ID NO 19
<211> LENGTH: 10
<212> TYPE: DNA
<213> ORGANISM: Artificial Sequence
<220> FEATURE:
<223> OTHER INFORMATION: Antisense oligonucleotide

<400> SEQUENCE: 19
atagcgaggc                                                     10

<210> SEQ ID NO 20
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 20
tgggagccat agcgag                                              16

<210> SEQ ID NO 21
<211> LENGTH: 16
<212> TYPE: DNA
<213> ORGANISM: Artificial Sequence
<220> FEATURE:
<223> OTHER INFORMATION: Antisense oligonucleotide

<400> SEQUENCE: 21
ggagccatag cgaggc                                              16

<210> SEQ ID NO 22
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 22
gcccaagctg gcatccgtca                                          20

<210> SEQ ID NO 23
<211> LENGTH: 20
<212> TYPE: DNA
```

```
<213> ORGANISM: Artificial Sequence
<220> FEATURE:
<223> OTHER INFORMATION: Antisense oligonucleotide

<400> SEQUENCE: 23
tctgtaagtc tgtgggcctc                                                20

<210> SEQ ID NO 24
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 24
agtcttgctc cttcctcttg                                                20

<210> SEQ ID NO 25
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 25
ctcatcaggc tagactttaa                                                20

<210> SEQ ID NO 26
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 26
tgtcctcatg gtggggctat                                                20

<210> SEQ ID NO 27
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 27
tctgagtagc agaggagctc ga                                             22

<210> SEQ ID NO 28
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 28
caatcatgac ttcaagagtt ct                                             22

<210> SEQ ID NO 29
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 29
accacactgg tatttcacac                                                20
```

<210> SEQ ID NO 30
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 30
gtatggaaga ttataatata t                                              21

<210> SEQ ID NO 31
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 31
cacaatcctt aagaactctt t                                              21

<210> SEQ ID NO 32
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 32
acctctgctg ttctgatcct                                                20

<210> SEQ ID NO 33
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 33
ctgctgcctc tgtctcaggt                                                20

<210> SEQ ID NO 34
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 34
ggtatttgac acagc                                                     15

<210> SEQ ID NO 35
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 35
aatcatgact tcaagagttc t                                              21

<210> SEQ ID NO 36
<211> LENGTH: 21
<212> TYPE: DNA
<213> ORGANISM: Artificial Sequence
<220> FEATURE:

<223> OTHER INFORMATION: Antisense oligonucleotide

<400> SEQUENCE: 36
tgaagcaatc atgacttcaa g          21

<210> SEQ ID NO 37
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 37
tataggagtt ttgatgtgaa          20

<210> SEQ ID NO 38
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 38
acaatgaggg ggtaatctac a          21

<210> SEQ ID NO 39
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 39
gacaatatac aaaccttcca t          21

<210> SEQ ID NO 40
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 40
ccaggcattt taagttgctg t          21

<210> SEQ ID NO 41
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 41
cctgaagcca gtgaggcccg          20

<210> SEQ ID NO 42
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 42
gatgagaaaa tagtggaacc a          21

```
<210> SEQ ID NO 43
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 43
ctgagcaaga tatctagat                                                  19

<210> SEQ ID NO 44
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 44
ctacactttt gatttctgt                                                  19

<210> SEQ ID NO 45
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 45
ttgaacatat caagcattag ct                                              22

<210> SEQ ID NO 46
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 46
tttacatatg tacaaattat gt                                              22

<210> SEQ ID NO 47
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 47
aattatcact ttactataca aa                                              22

<210> SEQ ID NO 48
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 48
agggctgacc aagacggttg t                                               21

<210> SEQ ID NO 49
<211> LENGTH: 20
<212> TYPE: DNA
<213> ORGANISM: Artificial Sequence
<220> FEATURE:
<223> OTHER INFORMATION: Antisense oligonucleotide
```

<400> SEQUENCE: 49
ccatcttccc aggcatttta                                          20

<210> SEQ ID NO 50
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 50
aacccagtgc tccctttgct                                          20

<210> SEQ ID NO 51
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 51
aacccagtgc tccctttgct                                          20

<210> SEQ ID NO 52
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 52
gaagtcagcc aagaacagct                                          20

<210> SEQ ID NO 53
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 53
acaggatctc tcaggtgggt                                          20

<210> SEQ ID NO 54
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 54
ccaaagtgag agctgagaga                                          20

<210> SEQ ID NO 55
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 55
ctgattcaag gctttggcag                                          20

<210> SEQ ID NO 56
<211> LENGTH: 20

```
<212> TYPE: DNA
<213> ORGANISM: Artificial Sequence
<220> FEATURE:
<223> OTHER INFORMATION: Antisense oligonucleotide

<400> SEQUENCE: 56
ttccccagat gcacctgttt                                               20

<210> SEQ ID NO 57
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 57
gggccagaga cccgaggaga                                               20

<210> SEQ ID NO 58
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 58
acgtttggcc tcatggaagt                                               20

<210> SEQ ID NO 59
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 59
ggaatgcaaa gcacatccat                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 60
cgatgcagat accgcggagt                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 61
gcctgggagg gtattcagct                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 62
```

| | |
|---|---|
| cctgtgtgtg cctgggaggg | 20 |

<210> SEQ ID NO 63
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 63

| | |
|---|---|
| ggcattttaa gttgctgtcg | 20 |

<210> SEQ ID NO 64
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 64

| | |
|---|---|
| cagcctgcct tactgtgggc | 20 |

<210> SEQ ID NO 65
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 65

| | |
|---|---|
| cttgaacaat taattccacc t | 21 |

<210> SEQ ID NO 66
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 66

| | |
|---|---|
| ttaccattga cataaagtgt t | 21 |

<210> SEQ ID NO 67
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 67

| | |
|---|---|
| ctgtgtctcc tgtctccgct | 20 |

<210> SEQ ID NO 68
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 68

| | |
|---|---|
| gtctttgttg ttttctcttc c | 21 |

<210> SEQ ID NO 69
<211> LENGTH: 20
<212> TYPE: DNA
<213> ORGANISM: Artificial Sequence

```
<220> FEATURE:
<223> OTHER INFORMATION: Antisense oligonucleotide

<400> SEQUENCE: 69
tgaacatatc aagcattagc                                                    20

<210> SEQ ID NO 70
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 70
gcaatcttgc tatggcataa                                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 71
cccggcatct ttacaaaacc                                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 72
aacatctccg taccatgcca                                                    20

<210> SEQ ID NO 73
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 73
tcactgctgc ctctgtctca gg                                                 22

<210> SEQ ID NO 74
<211> LENGTH: 23
<212> TYPE: DNA
<213> ORGANISM: Artificial Sequence
<220> FEATURE:
<223> OTHER INFORMATION: Antisense oligonucleotide

<400> SEQUENCE: 74
tgattctttt gaacttaaaa gga                                                23

<210> SEQ ID NO 75
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 75
ttaaaggatg taagaaggct                                                    20
```

<210> SEQ ID NO 76
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 76
cataagcaca tttattgtc                                                19

<210> SEQ ID NO 77
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 77
ttttgggaag cagttgttca                                               20

<210> SEQ ID NO 78
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 78
aactgtgaag caatcatgac t                                             21

<210> SEQ ID NO 79
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 79
ccttgagtgg tgcattcaac ct                                            22

<210> SEQ ID NO 80
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 80
aatgcttgct cacacaggca tt                                            22

<210> SEQ ID NO 81
<211> LENGTH: 18
<212> TYPE: DNA
<213> ORGANISM: Artificial Sequence
<220> FEATURE:
<223> OTHER INFORMATION: Antisense oligonucleotide

<400> SEQUENCE: 81
gcctcgctat ggctccca                                                 18

<210> SEQ ID NO 82
<211> LENGTH: 18
<212> TYPE: DNA
<213> ORGANISM: Artificial Sequence
<220> FEATURE:
<223> OTHER INFORMATION: Antisense oligonucleotide

```
<400> SEQUENCE: 82
catggcgcgg gccgcggg                                              18

<210> SEQ ID NO 83
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 83
tgcatccccc aggccaccat                                            20

<210> SEQ ID NO 84
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 84
tctgagtagc agaggagctc                                            20

<210> SEQ ID NO 85
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 85
tatgtctccc ccaccacttc                                            20

<210> SEQ ID NO 86
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 86
agggccactg ctcgtccaca                                            20

<210> SEQ ID NO 87
<211> LENGTH: 3017
<212> TYPE: DNA
<213> ORGANISM: Homo sapiens

<400> SEQUENCE: 87
gctataagga tcacgcgccc cagtcgacgc tgagctcctc tgctactcag agttgcaacc    60
tcagcctcgc tatggctccc agcagccccc ggcccgcgct gccgcactc ctggtcctgc   120 tcggggctct gttcccagga cctggcaatg cccagacatc tgtgtccccc tcaaaagtca   180
tcctgccccg gggaggctcc gtgctggtga catgcagcac ctcctgtgac cagcccaagt   240
tgttgggcat agagaccccg ttgcctaaaa aggagttgct cctgcctggg aacaaccgga   300
aggtgtatga actgagcaat gtgcaagaag atagccaacc aatgtgctat tcaaactgcc   360
ctgatgggca gtcaacagct aaaaccttcc tcaccgtgta ctggactcca gaacgggtgg   420
aactggcacc cctcccctct tggcagccag tgggcaagaa ccttacccta cgctgccagg   480
tggagggtgg ggcaccccgg gccaacctca ccgtggtgct gctccgtggg gagaaggagc   540
```

```
tgaaacggga gccagctgtg ggggagcccg ctgaggtcac gaccacggtg ctggtgagga      600
gagatcacca tggagccaat ttctcgtgcc gcactgaact ggacctgcgg ccccaagggc      660
tggagctgtt tgagaacacc tcggcccct accagctcca gacctttgtc ctgccagcga       720
ctcccccaca acttgtcagc ccccgggtcc tagaggtgga cacgcagggg accgtggtct      780
gttccctgga cgggctgttc ccagtctcgg aggcccaggt ccacctggca ctggggacc       840 agaggttgaa ccccacagtc acctatggca acgactcctt ctcggccaag gcctcagtca      900
gtgtgaccgc agaggacgag ggcacccagc ggctgacgtg tgcagtaata ctggggaacc      960
agagccagga gacactgcag acagtgacca tctacagctt tccggcgccc aacgtgattc     1020
tgacgaagcc agaggtctca gaagggaccg aggtgacagt gaagtgtgag gcccacccta     1080
gagccaaggt gacgctgaat ggggttccag cccagccact gggcccgagg gcccagctcc     1140
tgctgaaggc cacccagag acaacgggc gcagcttctc ctgctctgca accctggagg       1200
tggccggcca gcttatacac aagaaccaga cccgggagct tcgtgtcctg tatggccccc     1260
gactggacga gagggattgt ccgggaaact ggacgtggcc agaaaattcc cagcagactc     1320
caatgtgcca ggcttggggg aacccattgc ccgagctcaa gtgtctaaag gatggcactt     1380
tcccactgcc catcggggaa tcagtgactg tcactcgaga tcttgagggc acctacctct     1440
gtcgggccag gagcactcaa ggggaggtca cccgcgaggt gaccgtgaat gtgctctccc     1500
cccggtatga gattgtcatc atcactgtgg tagcagccgc agtcataatg ggcactgcag     1560
gcctcagcac gtacctctat aaccgccagc ggaagatcaa gaaatacaga ctacaacagg     1620
cccaaaaagg gacccccatg aaaccgaaca cacaagccac gcctcctga acctatcccg      1680 ggacaggcc tcttcctcgg ccttcccata ttggtggcag tggtgccaca ctgaacagag      1740
tggaagacat atgccatgca gctacaccta ccggccctgg gacgccggag gacagggcat     1800
tgtcctcagt cagatacaac agcatttggg gccatggtac ctgcacacct aaaacactag     1860
gccacgcatc tgatctgtag tcacatgact aagccaagag gaaggagcaa gactcaagac     1920
atgattgatg gatgttaaag tctagcctga tgagagggga agtggtgggg gagacatagc     1980
cccaccatga ggacatacaa ctgggaaata ctgaaacttg ctgcctattg ggtatgctga     2040
ggccacagda cttacagaag aagtggccct catagacat gtgtagcatc aaaacacaaa     2100 gcccacact tcctgacgga tgccagcttg ggcactgctg tctactgacc caacccttg      2160 atgatatgta tttattcatt tgttatttta ccagctattt attgagtgtc tttatgtag     2220 gctaaatgaa cataggtctc tggcctcacg gagctcccag tccatgtcac attcaaggtc     2280
accaggtaca gttgtacagg ttgtacactg caggagagtg cctggcaaaa agatcaaatg     2340
gggctgggac ttctcattgg ccaacctgcc ttttccccaga aggagtgatt tttctatcgg    2400
cacaaaagca ctatatggac tggtaatggt tcacaggttc agagattacc cagtgaggcc     2460
ttattcctcc cttccccca aaactgacac ctttgttagc cacctcccca cccacataca      2520
tttctgccag tgttacaatg acactcagcg gtcatgtctg gacatgagtg cccagggaat     2580
atgcccaagc tatgccttgt cctcttgtcc tgtttgcatt tcactgggag cttgcactat     2640
tgcagctcca gtttcctgca gtgatcaggg tcctgcaagc agtggggaag ggggccaagg    2700
tattggagga ctccctccca gctttggaag ggtcatccgc gtgtgtgtgt gtgtgtatgt     2760
gtagacaagc tctcgctctg tcacccaggc tggagtgcag tggtgcaatc atggttcact     2820
gcagtcttga ccttttgggc tcaagtgatc ctcccacctc agcctcctga gtagctggga    2880
ccataggctc acaacaccac acctggcaaa tttgattttt ttttttttt tcagagacgg     2940
```

```
ggtctcgcaa cattgcccag acttcctttg tgttagttaa taaagctttc tcaactgcca    3000
aaaaaaaaaa aaaaaaa                                                   3017

<210> SEQ ID NO 88
<211> LENGTH: 532
<212> TYPE: PRT
<213> ORGANISM: Homo sapiens

<400> SEQUENCE: 88
```

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

-continued

```
Arg Ala Gln Leu Leu Lys Ala Thr Pro Glu Asp Asn Gly Arg Ser
        355                 360                 365
Phe Ser Cys Ser Ala Thr Leu Glu Val Ala Gly Gln Leu Ile His Lys
    370                 375                 380
Asn Gln Thr Arg Glu Leu Arg Val Leu Tyr Gly Pro Arg Leu Asp Glu
385                 390                 395                 400
Arg Asp Cys Pro Gly Asn Trp Thr Trp Pro Glu Asn Ser Gln Gln Thr
                405                 410                 415
Pro Met Cys Gln Ala Trp Gly Asn Pro Leu Pro Glu Leu Lys Cys Leu
            420                 425                 430
Lys Asp Gly Thr Phe Pro Leu Pro Ile Gly Glu Ser Val Thr Val Thr
        435                 440                 445
Arg Asp Leu Glu Gly Thr Tyr Leu Cys Arg Ala Arg Ser Thr Gln Gly
    450                 455                 460
Glu Val Thr Arg Glu Val Thr Val Asn Val Leu Ser Pro Arg Tyr Glu
465                 470                 475                 480
Ile Val Ile Ile Thr Val Val Ala Ala Val Ile Met Gly Thr Ala
                485                 490                 495
Gly Leu Ser Thr Tyr Leu Tyr Asn Arg Gln Arg Lys Ile Lys Lys Tyr
        500                 505                 510
Arg Leu Gln Gln Ala Gln Lys Gly Thr Pro Met Lys Pro Asn Thr Gln
    515                 520                 525
Ala Thr Pro Pro
    530
```

<210> SEQ ID NO 89
<211> LENGTH: 3858
<212> TYPE: DNA
<213> ORGANISM: Homo sapiens

<400> SEQUENCE: 89

```
ttcacatcaa aactcctata ctgacctgag acagaggcag cagtgatacc cacctgagag      60
atcctgtgtt tgaacaactg cttcccaaaa cggaaagtat ttcaagccta aacctttggg     120
tgaaaagaac tcttgaagtc atgattgctt cacagtttct ctcagctctc actttggtgc     180
ttctcattaa agagagtgga gcctggtctt cacaacacct cacggaagct atgacttatg     240
atgaggccag tgcttattgt cagcaaaggt acacacacct ggttgcaatt caaaacaaag     300
aagagattga gtacctaaac tccatattga gctattcacc aagttattac tggattggaa     360
tcagaaaagt caacaatgtg tgggtctggg taggaaccca gaaacctctg acagaagaag     420
ccaagaactg ggctccaggt gaacccaaca ataggcaaaa agatgaggac tgcgtggaga     480
tctacatcaa gagagaaaaa gatgtgggca tgtggaatga tgagaggtgc agcaagaaga     540
agcttgccct atgctacaca gctgcctgta ccaatacatc ctgcagtggc acggtgaat      600
gtgtagagac catcaataat tacacttgca agtgtgaccc tggcttcagt ggactcaagt     660
gtgagcaaat tgtgaactgt acagccctgg aatcccctga gcatggaagc ctggtttgca     720
gtcacccact gggaaacttc agctacaatt cttcctgctc tatcagctgt gataggggtt     780
acctgccaag cagcatggag accatgcagt gtatgtcctc tggagaatgg agtgctccta     840
ttccagcctg caatgtggtt gagtgtgatg ctgtgacaaa tccagccaat gggttcgtgg     900
aatgtttcca aaaccctgga agcttcccat ggaacacaac ctgtacattt gactgtgaag     960
aaggatttga actaatggga gcccagagcc ttcagtgtac ctcatctggg aattgggaca    1020
acgagaagcc aacgtgtaaa gctgtgacat gcagggccgt ccgccagcct cagaatggct    1080
```

-continued

```
ctgtgaggtg cagccattcc cctgctggag agttcacctt caaatcatcc tgcaacttca   1140
cctgtgagga aggcttcatg ttgcagggac cagcccaggt tgaatgcacc actcaagggc   1200
agtggacaca gcaaatccca gtttgtgaag cttccagtg cacagccttg tccaaccccg   1260
agcgaggcta catgaattgt cttcctagtg cttctggcag tttccgttat gggtccagct   1320
gtgagttctc ctgtgagcag ggttttgtgt tgaagggatc caaaaggctc aatgtggcc    1380
ccacagggga gtgggacaac gagaagccca catgtgaagc tgtgagatgc gatgctgtcc   1440
accagccccc gaagggtttg gtgaggtgtg ctcattcccc tattggagaa ttcacctaca   1500
agtcctcttg tgccttcagc tgtgaggagg gatttgaatt atatggatca actcaacttg   1560
agtgcacatc tcagggacaa tggacagaag aggttccttc ctgccaagtg gtaaaatgtt   1620
caagcctggc agttccggga agatcaaca tgagctgcag tggggagccc gtgtttggca    1680
ctgtgtgcaa gttcgcctgt cctgaaggat ggacgctcaa tggctctgca gctcggacat   1740
gtggagccac aggacactgg tctggcctgc tacctacctg tgaagctccc actgagtcca   1800
acattccctt ggtagctgga cttttctgct ctggactctc cctcctgaca ttagcaccat   1860
ttctcctctg gcttcggaaa tgcttacgga agcaaagaa atttgttcct gccagcagct    1920
gccaaagcct tgaatcagat ggaagctacc aaaagccttc ttacatcctt taagttcaaa   1980
agaatcagaa acaggtgcat ctggggaact agagggatac actgaagtta acagagacag   2040
ataactctcc tcgggtctct ggccttctt gcctactatg ccagatgcct ttatggctga    2100
aaccgcaaca cccatcacca cttcaataga tcaaagtcca gcaggcaagg acggccttca   2160
actgaaaaga ctcagtgttc cctttcctac tctcaggatc aagaaagtgt tggctaatga   2220
agggaaagga tattttcttc caagcaaagg tgaagagacc aagactctga atctcagaa    2280
ttcctttttct aactctccct tgctcgctgt aaaatcttgg cacagaaaca caatattttg   2340
tggctttctt tcttttgccc ttcacagtgt ttcgacagct gattacacag ttgctgtcat   2400
aagaatgaat aataattatc cagagtttag aggaaaaaaa tgactaaaaa tattataact   2460
taaaaaatg acagatgttg aatgcccaca ggcaaatgca tggagggttg ttaatggtgc    2520
aaatcctact gaatgctctg tgcgagggtt actatgcaca atttaatcac tttcatccct   2580
atgggattca gtgcttctta aagagttctt aaggattgtg atatttttac ttgcattgaa   2640
tatattataa tcttccatac ttcttcattc aatacaagtg tggtagggac ttaaaaaact   2700
tgtaaatgct gtcaactatg atatggtaaa agttacttat tctagattac ccctcattg    2760
tttattaaca aattatgtta catctgtttt aaatttattt caaaagggaa actattgtc    2820
ccctagcaag gcatgatgtt aaccagaata aagttctgag tgttttact acagttgttt    2880
tttgaaaaca tggtagaatt ggagagtaaa aactgaatgg aaggtttgta tattgtcaga   2940
tatttttca gaaatatgtg gtttccacga tgaaaaactt ccatgaggcc aaacgttttg    3000
aactaataaa agcataaatg caaacacaca aaggtataat tttatgaatg tctttgttgg   3060
aaaagaatac agaagatgg atgtgctttg cattcctaca aagatgtttg tcagatgtga    3120
tatgtaaaca taattcttgt atattatgga agattttaaa ttcacaatag aaactcacca   3180
tgtaaaagag tcatctggta gattttttaac gaatgaagat gtctaatagt tattccctat   3240
ttgttttctt ctgtatgtta gggtgctctg gaagagagga atgcctgtgt gagcaagcat   3300
ttatgtttat ttataagcag atttaacaat tccaaaggaa tctccagttt tcagttgatc   3360
actggcaatg aaaaattctc agtcagtaat tgccaaagct gctctagcct tgaggagtgt   3420
```

-continued

```
gagaatcaaa actctcctac acttccatta acttagcatg tgttgaaaaa aaaagtttca    3480
gagaagttct ggctgaacac tgcaacgac aaagccaaca gtcaaaacag agatgtgata     3540
aggatcagaa cagcgagagt tcttttaaag gggcagaaaa actctgggaa ataagagaga   3600
acaactactg tgatcaggct atgtatggaa tacagtgtta ttttctttga aattgtttaa   3660
gtgttgtaaa tatttatgta aactgcatta gaaattagct gtgtgaaata ccagtgtggt    3720
ttgtgtttga gttttattga gaattttaaa ttataactta aaatatttta taatttttaa    3780
agtatatatt tatttaagct tatgtcagac ctatttgaca taacactata aaggttgaca    3840
ataaatgtgc ttatgttt                                                   3858
```

<210> SEQ ID NO 90
<211> LENGTH: 610
<212> TYPE: PRT
<213> ORGANISM: Homo sapiens

<400> SEQUENCE: 90

```
Met Ile Ala Ser Gln Phe Leu Ser Ala Leu Thr Leu Val Leu Leu Ile
 1               5                  10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45

Ala Ile Gln Asn Lys Glu Glu Ile Glu Tyr Leu Asn Ser Ile Leu Ser
    50                  55                  60

Tyr Ser Pro Ser Tyr Tyr Trp Ile Gly Ile Arg Lys Val Asn Asn Val
65                  70                  75                  80

Trp Val Trp Val Gly Thr Gln Lys Pro Leu Thr Glu Glu Ala Lys Asn
                85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125

Arg Cys Ser Lys Lys Lys Leu Ala Leu Cys Tyr Thr Ala Ala Cys Thr
    130                 135                 140

Asn Thr Ser Cys Ser Gly His Gly Glu Cys Val Glu Thr Ile Asn Asn
145                 150                 155                 160

Tyr Thr Cys Lys Cys Asp Pro Gly Phe Ser Gly Leu Lys Cys Glu Gln
                165                 170                 175

Ile Val Asn Cys Thr Ala Leu Glu Ser Pro Glu His Gly Ser Leu Val
            180                 185                 190

Cys Ser His Pro Leu Gly Asn Phe Ser Tyr Asn Ser Ser Cys Ser Ile
        195                 200                 205

Ser Cys Asp Arg Gly Tyr Leu Pro Ser Ser Met Glu Thr Met Gln Cys
    210                 215                 220

Met Ser Ser Gly Glu Trp Ser Ala Pro Ile Pro Ala Cys Asn Val Val
225                 230                 235                 240

Glu Cys Asp Ala Val Thr Asn Pro Ala Asn Gly Phe Val Glu Cys Phe
                245                 250                 255

Gln Asn Pro Gly Ser Phe Pro Trp Asn Thr Thr Cys Thr Phe Asp Cys
            260                 265                 270

Glu Glu Gly Phe Glu Leu Met Gly Ala Gln Ser Leu Gln Cys Thr Ser
        275                 280                 285

Ser Gly Asn Trp Asp Asn Glu Lys Pro Thr Cys Lys Ala Val Thr Cys
```

```
        290                 295                 300
Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
                325                 330                 335

Glu Gly Phe Met Leu Gln Gly Pro Ala Gln Val Glu Cys Thr Thr Gln
                340                 345                 350

Gly Gln Trp Thr Gln Gln Ile Pro Val Cys Glu Ala Phe Gln Cys Thr
                355                 360                 365

Ala Leu Ser Asn Pro Glu Arg Gly Tyr Met Asn Cys Leu Pro Ser Ala
370                 375                 380

Ser Gly Ser Phe Arg Tyr Gly Ser Ser Cys Glu Phe Ser Cys Glu Gln
385                 390                 395                 400

Gly Phe Val Leu Lys Gly Ser Lys Arg Leu Gln Cys Gly Pro Thr Gly
                405                 410                 415

Glu Trp Asp Asn Glu Lys Pro Thr Cys Glu Ala Val Arg Cys Asp Ala
                420                 425                 430

Val His Gln Pro Pro Lys Gly Leu Val Arg Cys Ala His Ser Pro Ile
                435                 440                 445

Gly Glu Phe Thr Tyr Lys Ser Ser Cys Ala Phe Ser Cys Glu Glu Gly
                450                 455                 460

Phe Glu Leu Tyr Gly Ser Thr Gln Leu Glu Cys Thr Ser Gln Gly Gln
465                 470                 475                 480

Trp Thr Glu Glu Val Pro Ser Cys Gln Val Val Lys Cys Ser Ser Leu
                485                 490                 495

Ala Val Pro Gly Lys Ile Asn Met Ser Cys Ser Gly Glu Pro Val Phe
                500                 505                 510

Gly Thr Val Cys Lys Phe Ala Cys Pro Glu Gly Trp Thr Leu Asn Gly
                515                 520                 525

Ser Ala Arg Thr Cys Gly Ala Thr Gly His Trp Ser Gly Leu Leu
530                 535                 540

Pro Thr Cys Glu Ala Pro Thr Glu Ser Asn Ile Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Leu Arg Lys Ala Lys Lys Phe Val Pro Ala Ser
                580                 585                 590

Ser Cys Gln Ser Leu Glu Ser Asp Gly Ser Tyr Gln Lys Pro Ser Tyr
                595                 600                 605

Ile Leu
610

<210> SEQ ID NO 91
<211> LENGTH: 2813
<212> TYPE: DNA
<213> ORGANISM: Homo sapiens

<400> SEQUENCE: 91
cgggcctcac tggcttcagg agctgaatac cctcccaggc acacacaggt gggacacaaa      60
taagggtttt ggaaccacta ttttctcatc acgacagcaa cttaaaatgc ctggaagat     120 ggtcgtgatc cttggagcct caaatatact ttggataatg tttgcagctt ctcaagcttt    180
taaaatcgag accacccag aatctagata tcttgctcag attggtgact ccgtctcatt     240
gacttgcagc accacaggct gtgagtcccc attttctct tggagaaccc agatagatag      300
```

-continued

```
tccactgaat gggaaggtga cgaatgaggg gaccacatct acgctgacaa tgaatcctgt    360
tagttttggg aacgaacact cttacctgtg cacagcaact tgtgaatcta ggaaattgga    420
aaaaggaatc caggtggaga tctactcttt tcctaaggat ccagagattc atttgagtgg    480
ccctctggag gctgggaagc cgatcacagt caagtgttca gttgctgatg tatacccatt    540
tgacaggctg gagatagact tactgaaagg agatcatctc atgaagagtc aggaatttct    600
ggaggatgca gacaggaagt ccctggaaac caagagtttg gaagtaacct ttactcctgt    660
cattgaggat attggaaaag ttcttgtttg ccgagctaaa ttacacattg atgaaatgga    720
ttctgtgccc acagtaaggc aggctgtaaa agaattgcaa gtctacatat cacccaagaa    780
tacagttatt tctgtgaatc catccacaaa gctgcaagaa ggtggctctg tgaccatgac    840
ctgttccagc gagggtctac cagctccaga gattttctgg agtaagaaat tagataatgg    900
gaatctacag cacctttctg gaaatgcaac tctcaccttta attgctatga ggatggaaga    960
ttctggaatt tatgtgtgtg aaggagttaa tttgattggg aaaaacagaa aagaggtgga   1020
attaattgtt caagcattcc ctagagatcc agaaatcgag atgagtggtg gcctcgtgaa   1080
tgggagctct gtcactgtaa gctgcaaggt tcctagcgtg tacccccttg accggctgga   1140
gattgaatta cttaaggggg agactattct ggagaatata gagttttttgg aggatacgga   1200 tatgaaatct ctagagaaca aaagtttgga aatgaccttc atccctacca ttgaagatac   1260
tggaaaagct cttgtttgtc aggctaagtt acatattgat gacatggaat cgaacccaa   1320 acaaaggcag agtacgcaaa cactttatgt caatgttgcc cccagagata caaccgtctt   1380
ggtcagccct tcctccatcc tggaggaagg cagttctgtg aatatgacat gcttgagcca   1440
gggctttcct gctccgaaaa tcctgtggag caggcagctc cctaacgggg agctacagcc   1500
tctttctgag aatgcaactc tcaccttaat ttctacaaaa atggaagatt ctggggttta   1560
tttatgtgaa ggaattaacc aggctggaag aagcagaaag gaagtggaat taattatcca   1620
agttactcca aaagacataa aacttacagc ttttccttct gagagtgtca agaaggaga   1680 cactgtcatc atctcttgta catgtggaaa tgttccagaa acatggataa tcctgaagaa   1740
aaaagcggag acaggagaca cagtactaaa atctatagat ggcgcctata ccatccgaaa   1800
ggcccagttg aaggatgcgg gagtatatga atgtgaatct aaaaacaaag ttggctcaca   1860
attaagaagt ttaacacttg atgttcaagg aagagaaaac aacaaagact atttttctcc   1920
tgagcttctc gtgctctatt ttgcatcctc cttaataata cctgccattg gaatgataat   1980
ttactttgca agaaaagcca acatgaaggg gtcatatagt cttgtagaag cacagaaatc   2040
aaaagtgtag ctaatgcttg atatgttcaa ctggagacac tatttatctg tgcaaatcct   2100
tgatactgct catcattcct tgagaaaaac aatgagctga gaggcagact tccctgaatg   2160
tattgaactt ggaagaaat gcccatctat gtcccttgct gtgagcaaga agtcaaagta   2220
aaacttgctg cctgaagaac agtaactgcc atcaagatga gagaactgga ggagttcctt   2280
gatctgtata tacaataaca taatttgtac atatgtaaaa taaaattatg ccatagcaag   2340
attgcttaaa atagcaacac tctatattta gattgttaaa ataactagtg ttgcttggac   2400
tattataatt taatgcatgt taggaaaatt tcacattaat atttgctgac agctgacctt   2460
tgtcatcttt cttctatttt attcccttc acaaaatttt attcctatat agtttattga   2520
caataatttc aggttttgta agatgccgg gttttatatt tttatagaca ataataagc    2580 aaagggagca ctgggttgac tttcaggtac taaatacctc aacctatggt ataatggttg   2640
```

```
actgggtttc tctgtatagt actggcatgg tacggagatg tttcacgaag tttgttcatc    2700
agactcctgt gcaactttcc caatgtggcc taaaaatgca acttctttt atttctttt      2760 gtaaatgttt aggttttttt gtatagtaaa gtgataattt ctggaattaa aaa           2813
```

<210> SEQ ID NO 92
<211> LENGTH: 647
<212> TYPE: PRT
<213> ORGANISM: Homo sapiens

<400> SEQUENCE: 92

```
Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
                20                  25                  30

Ser Arg Tyr Leu Ala Gln Ile Gly Asp Ser Val Ser Leu Thr Cys Ser
            35                  40                  45

Thr Thr Gly Cys Glu Ser Pro Phe Phe Ser Trp Arg Thr Gln Ile Asp
        50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Ala Phe Pro Arg Asp Pro Glu Ile Glu Met Ser
305                 310                 315                 320

Gly Gly Leu Val Asn Gly Ser Ser Val Thr Val Ser Cys Lys Val Pro
                325                 330                 335

Ser Val Tyr Pro Leu Asp Arg Leu Glu Ile Glu Leu Leu Lys Gly Glu
            340                 345                 350
```

```
Thr Ile Leu Glu Asn Ile Glu Phe Leu Glu Asp Thr Asp Met Lys Ser
        355                 360                 365

Leu Glu Asn Lys Ser Leu Glu Met Thr Phe Ile Pro Thr Ile Glu Asp
        370                 375                 380

Thr Gly Lys Ala Leu Val Cys Gln Ala Lys Leu His Ile Asp Asp Met
385                     390                 395                 400

Glu Phe Glu Pro Lys Gln Arg Gln Ser Thr Gln Thr Leu Tyr Val Asn
                405                 410                 415

Val Ala Pro Arg Asp Thr Thr Val Leu Val Ser Pro Ser Ser Ile Leu
                420                 425                 430

Glu Glu Gly Ser Ser Val Asn Met Thr Cys Leu Ser Gln Gly Phe Pro
        435                 440                 445

Ala Pro Lys Ile Leu Trp Ser Arg Gln Leu Pro Asn Gly Glu Leu Gln
        450                 455                 460

Pro Leu Ser Glu Asn Ala Thr Leu Thr Leu Ile Ser Thr Lys Met Glu
465                 470                 475                 480

Asp Ser Gly Val Tyr Leu Cys Glu Gly Ile Asn Gln Ala Gly Arg Ser
                485                 490                 495

Arg Lys Glu Val Glu Leu Ile Ile Gln Val Thr Pro Lys Asp Ile Lys
                500                 505                 510

Leu Thr Ala Phe Pro Ser Glu Ser Val Lys Glu Gly Asp Thr Val Ile
        515                 520                 525

Ile Ser Cys Thr Cys Gly Asn Val Pro Glu Thr Trp Ile Ile Leu Lys
        530                 535                 540

Lys Lys Ala Glu Thr Gly Asp Thr Val Leu Lys Ser Ile Asp Gly Ala
545                 550                 555                 560

Tyr Thr Ile Arg Lys Ala Gln Leu Lys Asp Ala Gly Val Tyr Glu Cys
                565                 570                 575

Glu Ser Lys Asn Lys Val Gly Ser Gln Leu Arg Ser Leu Thr Leu Asp
                580                 585                 590

Val Gln Gly Arg Glu Asn Asn Lys Asp Tyr Phe Ser Pro Glu Leu Leu
        595                 600                 605

Val Leu Tyr Phe Ala Ser Ser Leu Ile Ile Pro Ala Ile Gly Met Ile
        610                 615                 620

Ile Tyr Phe Ala Arg Lys Ala Asn Met Lys Gly Ser Tyr Ser Leu Val
625                 630                 635                 640

Glu Ala Gln Lys Ser Lys Val
                645
```